(12) United States Patent
Bonutti et al.

(10) Patent No.: US 6,475,230 B1
(45) Date of Patent: Nov. 5, 2002

(54) METHOD AND APPARATUS FOR SECURING A SUTURE

(75) Inventors: Peter M. Bonutti, 15167 N. Cardinal Dr., Effingham, IL (US) 62401; Matthew J. Cremens, Effingham, IL (US); Ping Liu, Charleston, IL (US)

(73) Assignee: Peter M. Bonutti, Effingham, IL (US)

( * ) Notice: Subject to any disclaimer, the term of this patent is extended or adjusted under 35 U.S.C. 154(b) by 0 days.

(21) Appl. No.: 09/523,442

(22) Filed: Mar. 10, 2000

Related U.S. Application Data

(63) Continuation-in-part of application No. 09/348,940, filed on Jul. 7, 1999, now Pat. No. 6,159,234, which is a continuation-in-part of application No. 08/905,084, filed on Aug. 1, 1997, now Pat. No. 6,010,525.

(51) Int. Cl.[7] .............................................. A61B 17/04
(52) U.S. Cl. ..................................................... 606/232
(58) Field of Search ......................................... 606/232

(56) References Cited

U.S. PATENT DOCUMENTS

| | | | |
|---|---|---|---|
| 4,705,040 A | 11/1987 | Mueller et al. | ............. 606/232 |
| 4,750,492 A | 6/1988 | Jacobs | ......................... 606/232 |
| 5,258,015 A * | 11/1993 | Li et al. | ...................... 606/232 |
| 5,306,280 A | 4/1994 | Bregen et al. | ............... 606/232 |
| 5,383,905 A * | 1/1995 | Golds et al. | ................. 606/232 |
| 5,669,917 A * | 9/1997 | Sauer et al. | ................. 606/139 |
| 5,906,625 A | 5/1999 | Bito et al. | ................... 606/232 |
| 5,964,765 A | 10/1999 | Fenton, Jr. et al. | ......... 606/232 |
| 6,066,160 A * | 5/2000 | Colvin et al. | ............... 606/232 |
| 6,086,608 A * | 7/2000 | Ek et al. | ...................... 606/232 |
| 6,099,537 A | 8/2000 | Sugai et al. | ................. 606/232 |
| 6,174,324 B1 | 1/2001 | Egan et al. | .................. 606/232 |

FOREIGN PATENT DOCUMENTS

JP  8-140982  6/1996

* cited by examiner

Primary Examiner—Gary Jackson
(74) Attorney, Agent, or Firm—Tarolli, Sundheim, Covell, Tummino & Szabo, L.L.P.

(57) ABSTRACT

An improved method and apparatus is provided to secure a suture relative to body tissue. When a predetermined minimum force is being transmitted between a suture retainer and the body tissue, the suture is gripped with the suture retainer by plastically deforming material of the suture retainer. One or more bends may be formed in suture by the suture retainer to increase the holding action between the suture retainer and the suture. The bends in the suture may be formed by wrapping the suture around a portion of the suture retainer. During movement of the suture retainer toward the body tissue, the bends may be moved along the suture. One or more bends may be formed in the suture by bending a tubular member through which the suture extends. The tubular member may be maintained in a bent condition by a C-shaped holder member. Alternatively, the tubular member may be maintained in a bent condition by members which are latched together.

149 Claims, 19 Drawing Sheets

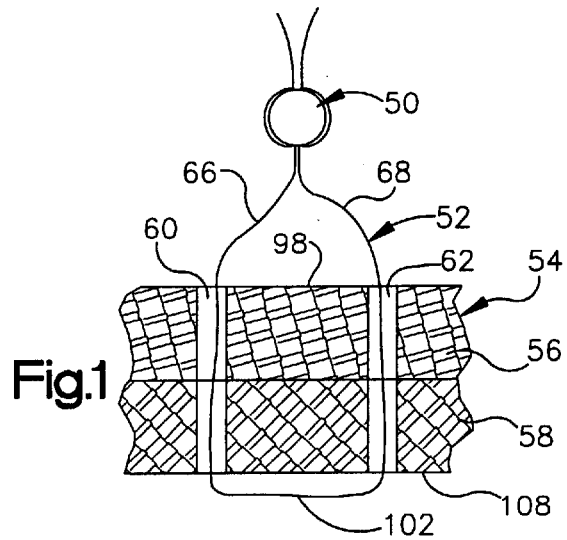
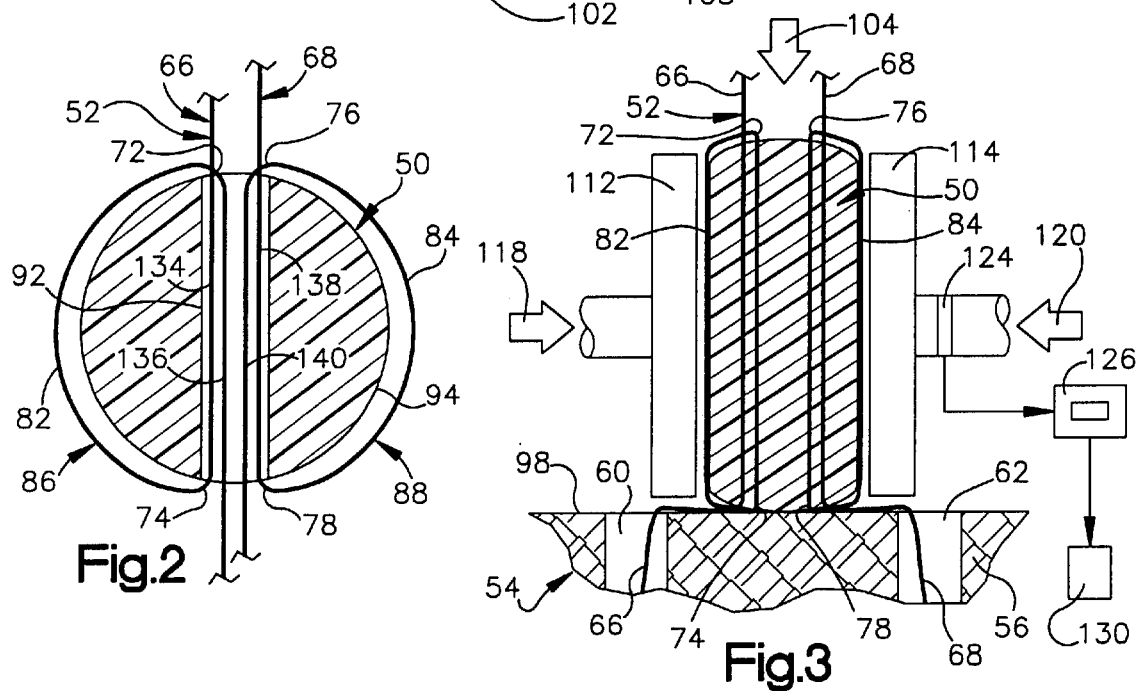
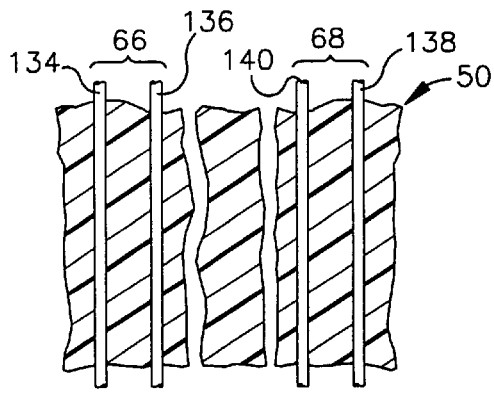
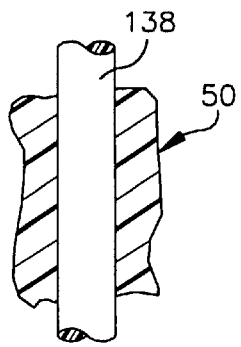
Fig.1 Fig.2 Fig.3 Fig.4 Fig.5

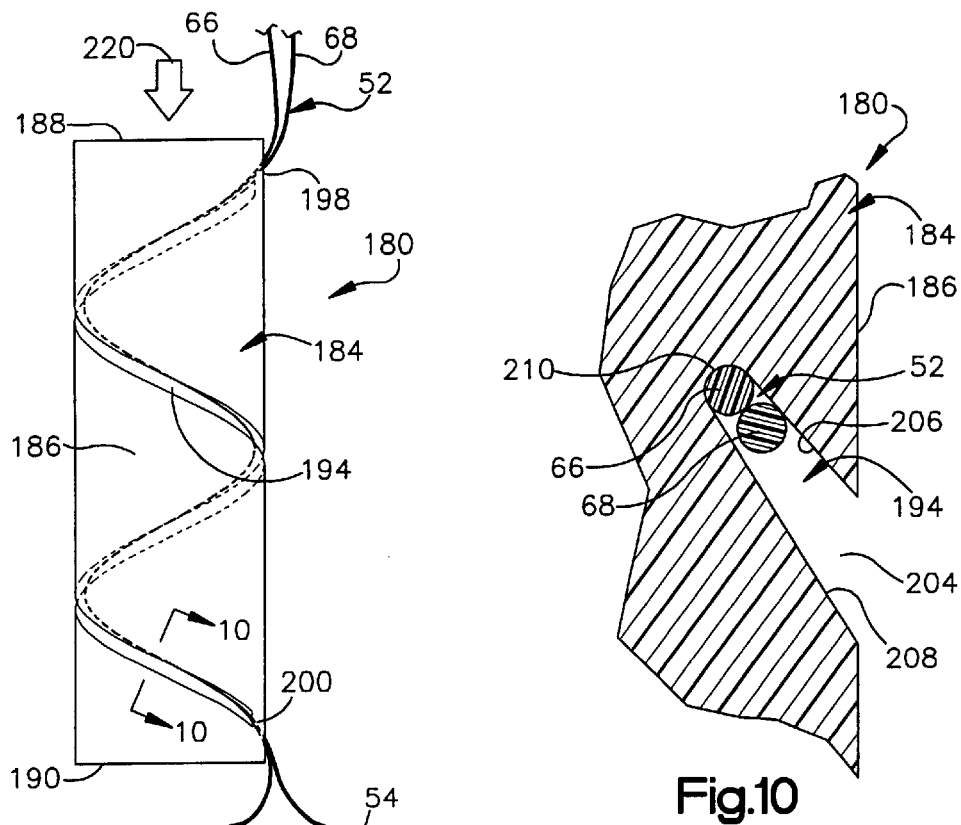
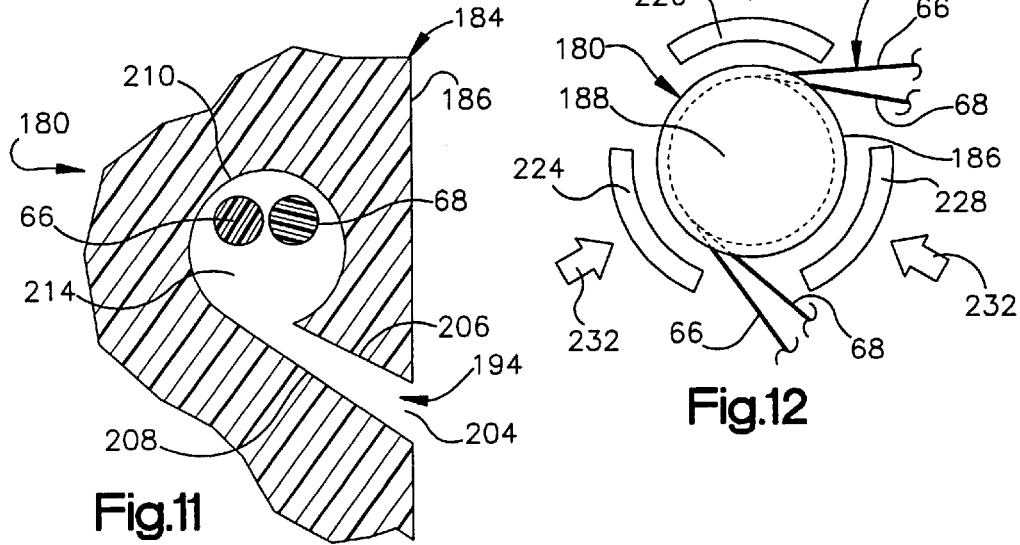

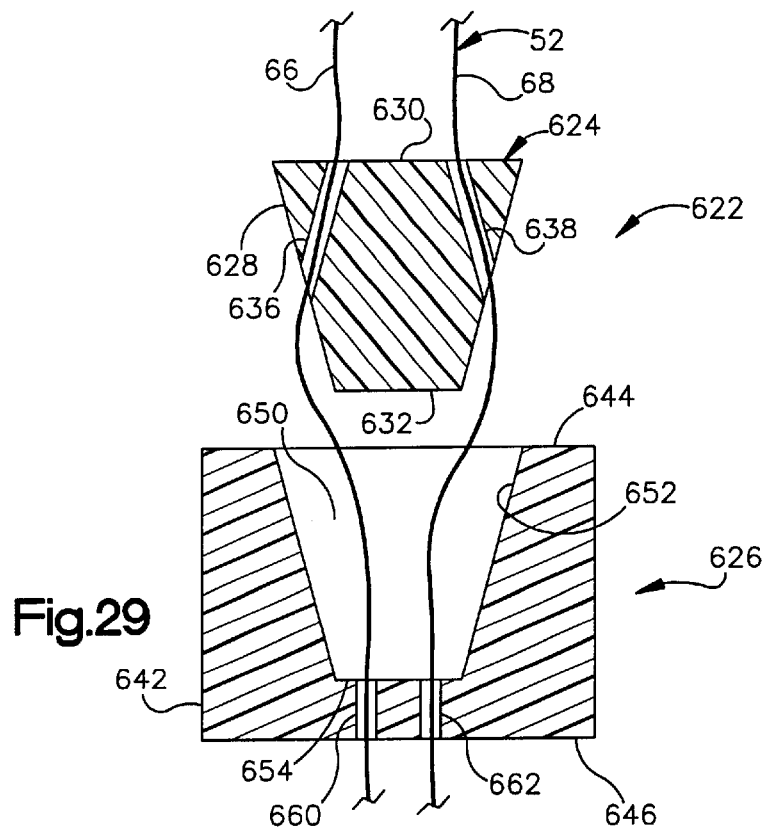
Fig.29
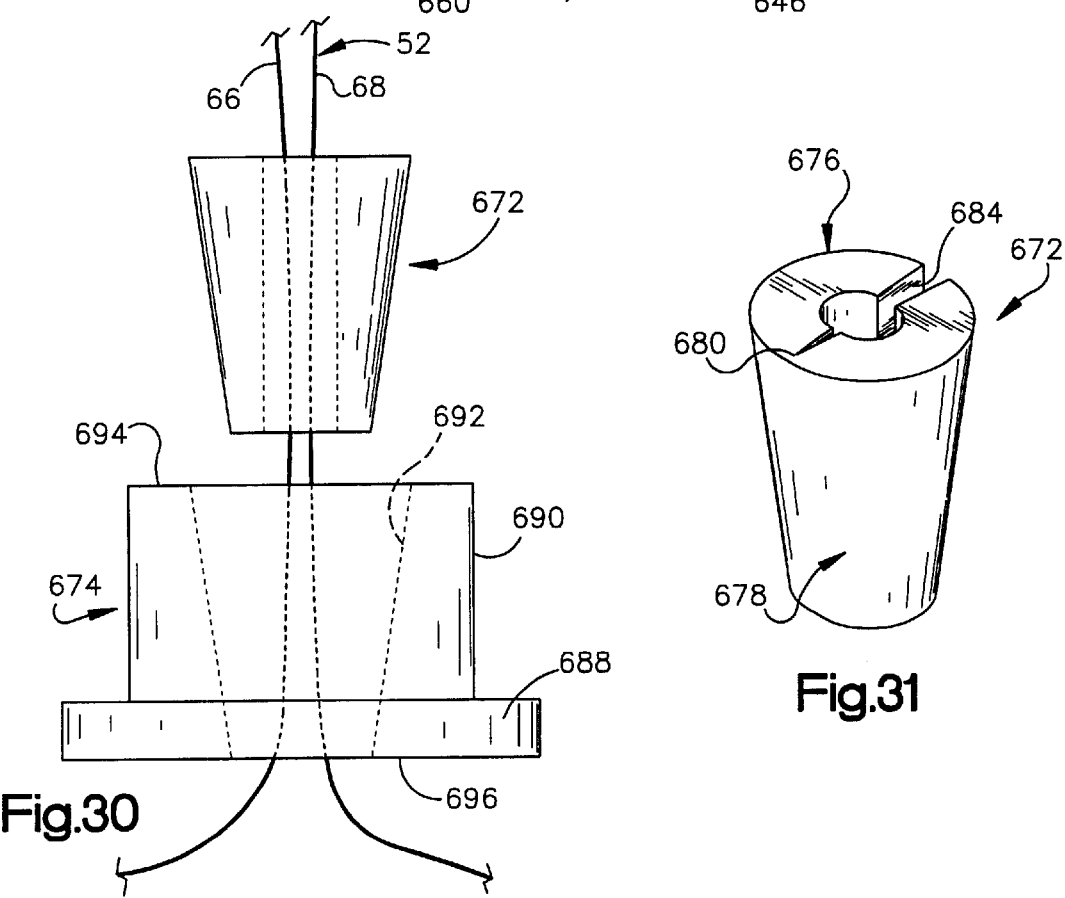
Fig.30
Fig.31

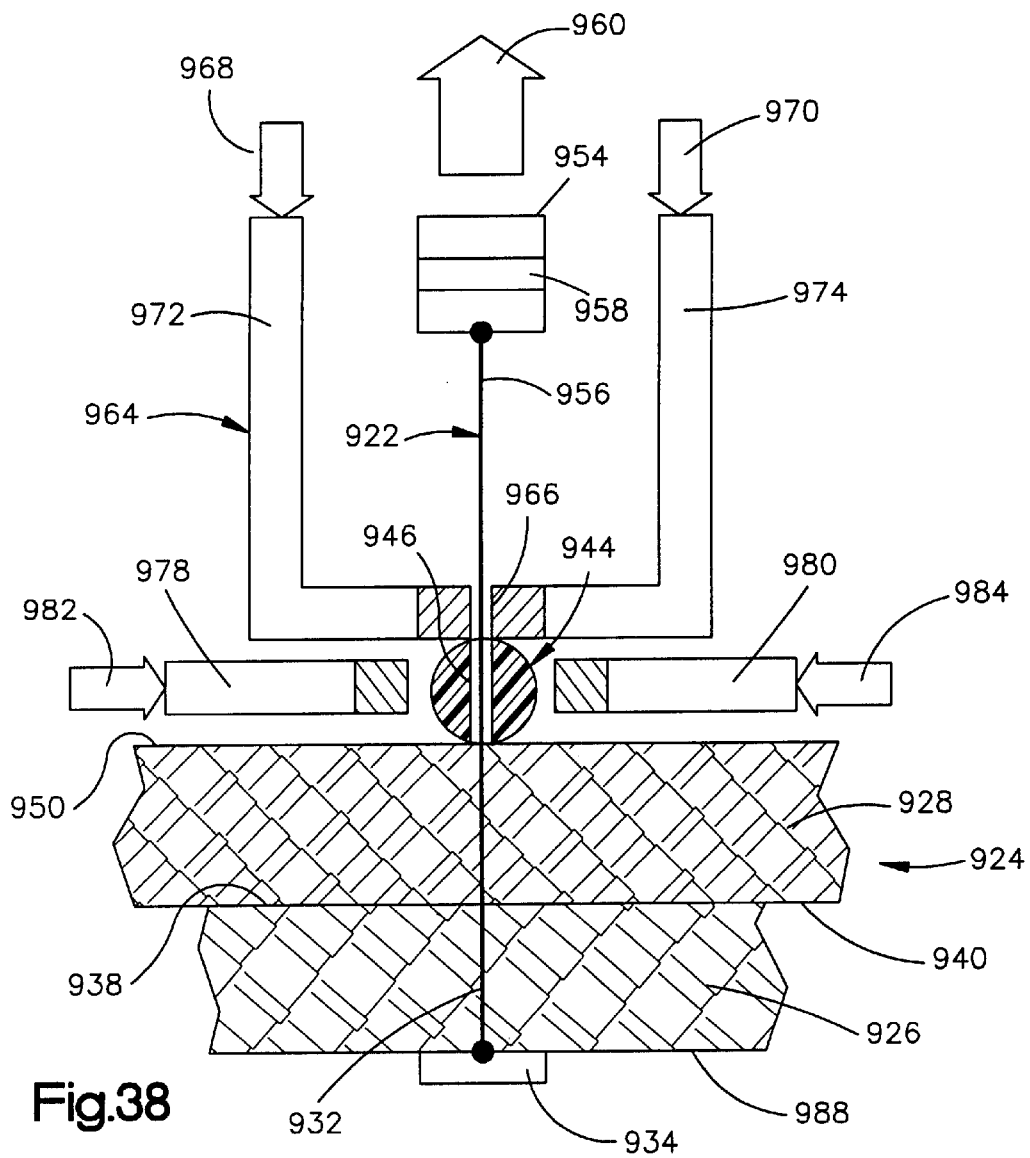

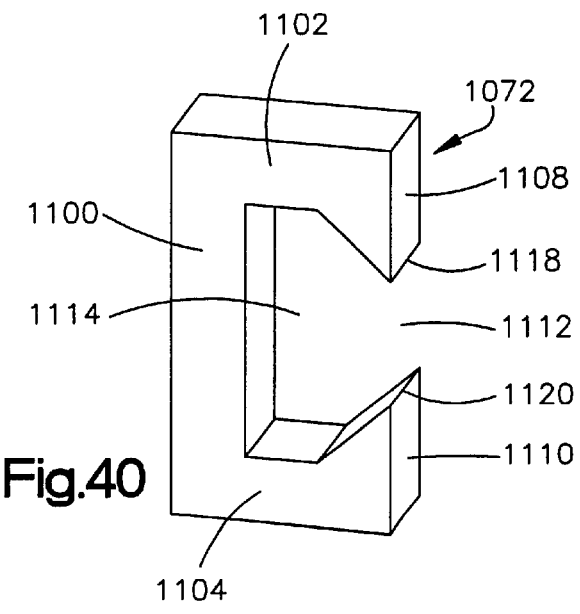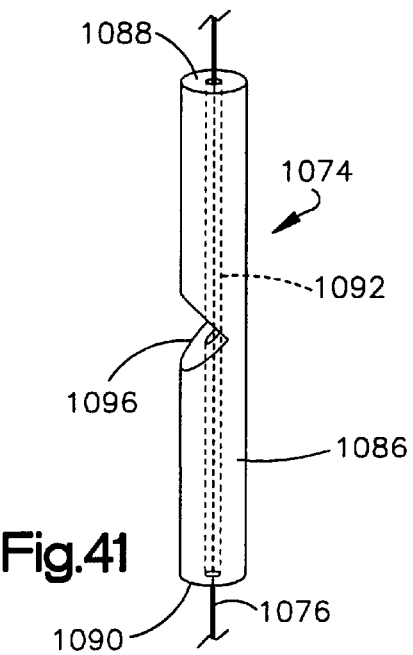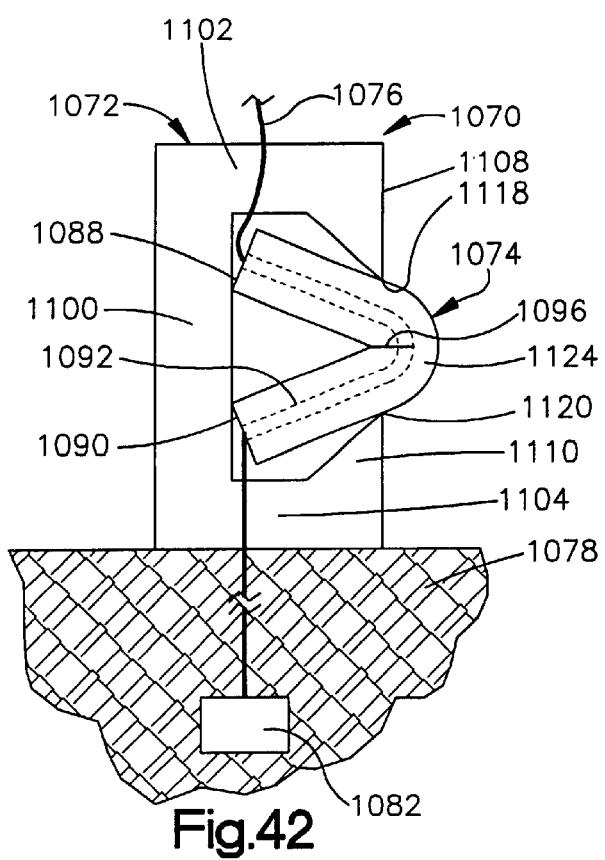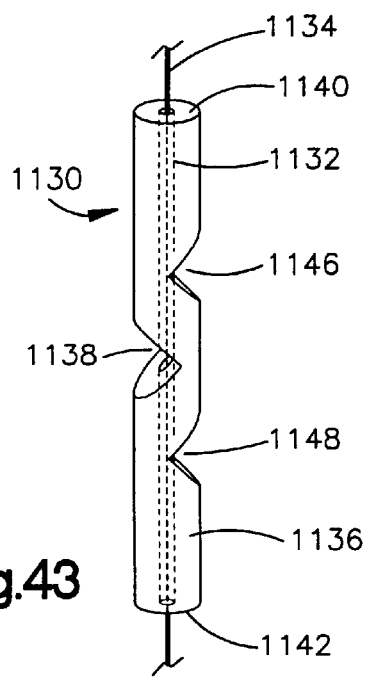

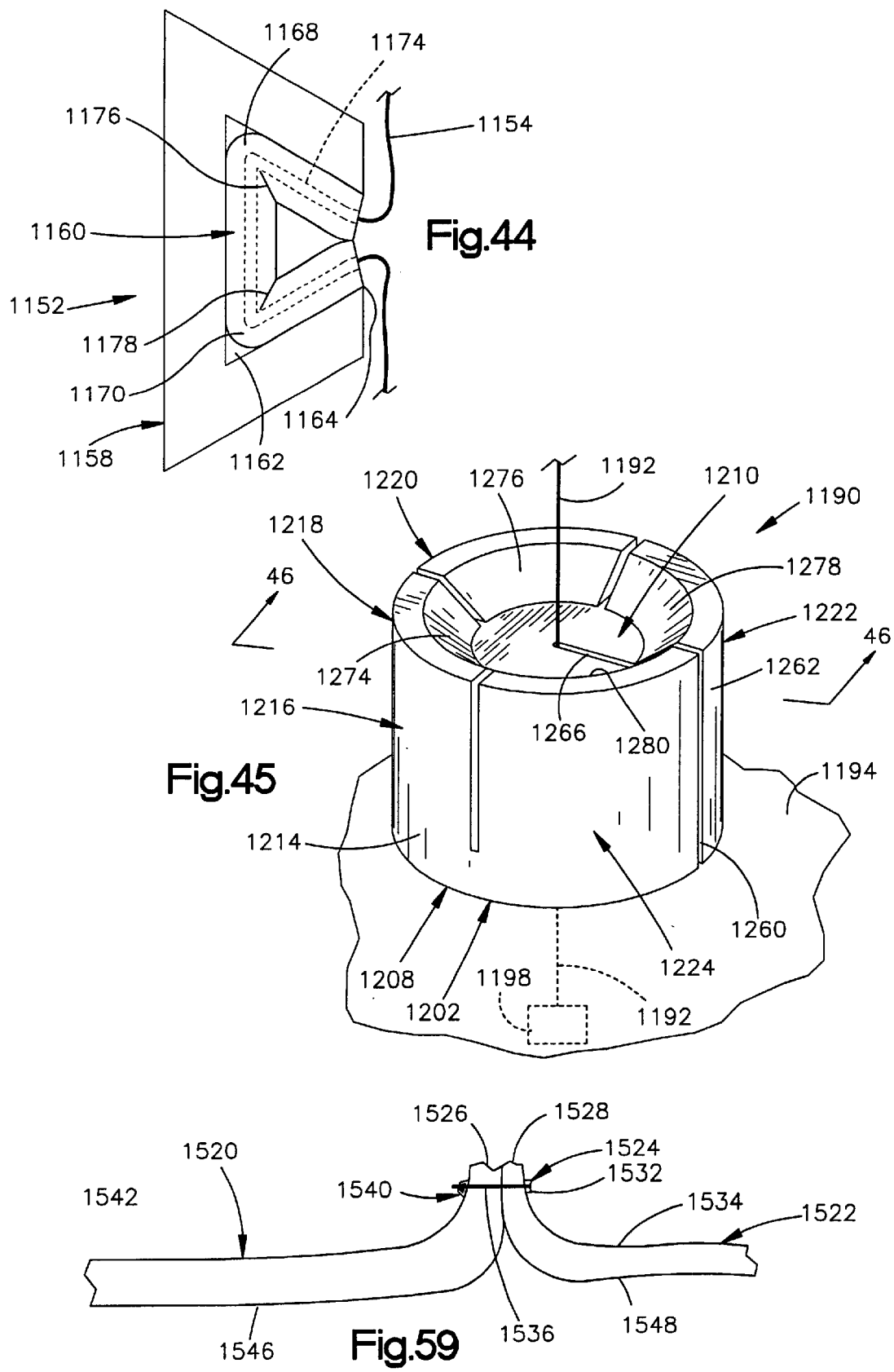

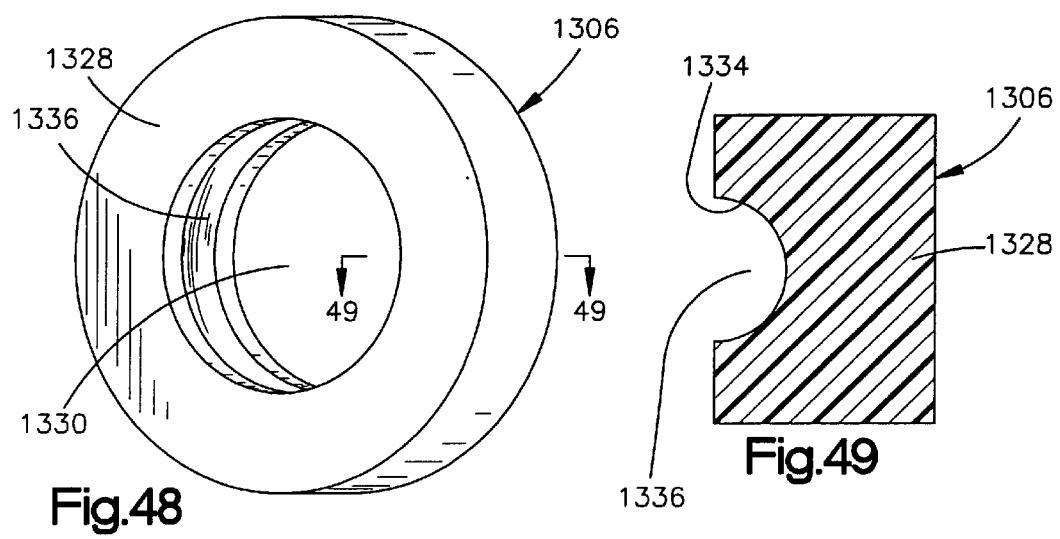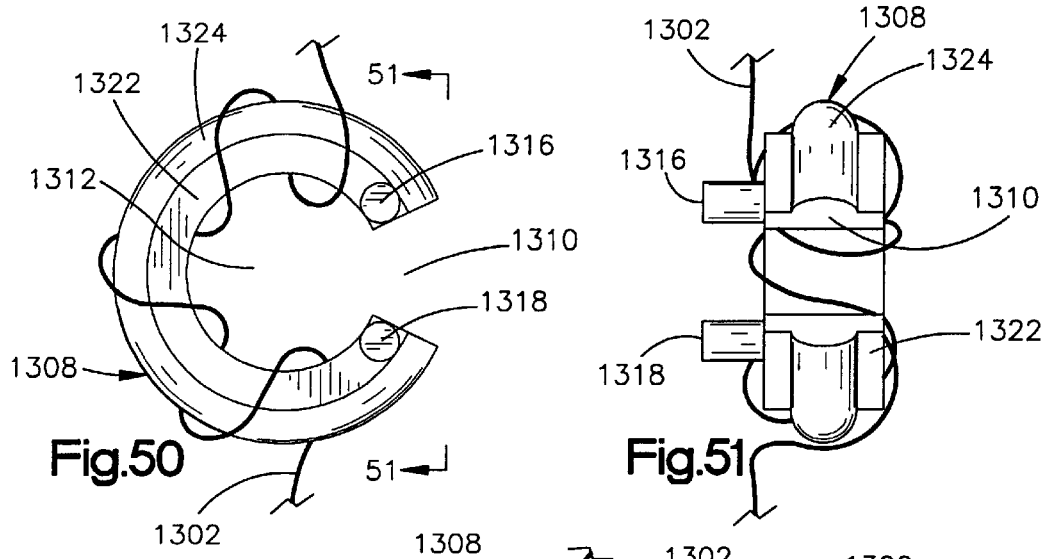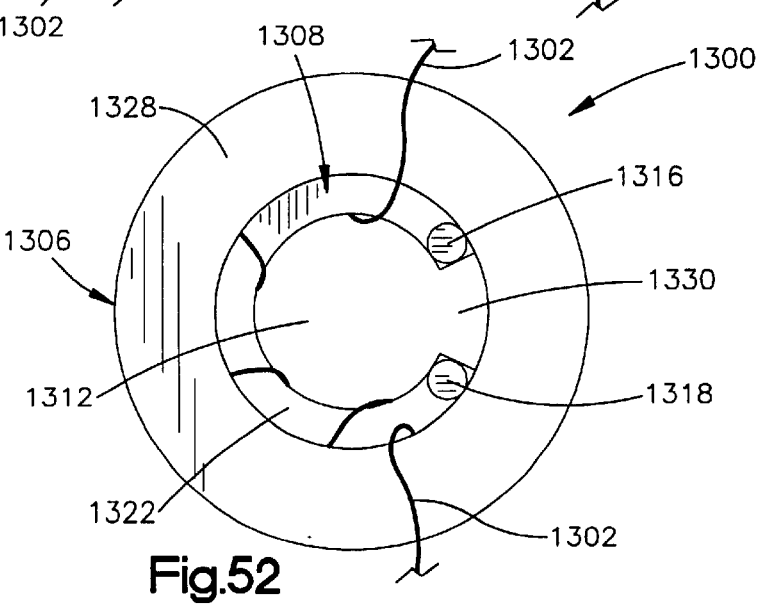

METHOD AND APPARATUS FOR SECURING A SUTURE

RELATED APPLICATION

This application is a continuation-in-part of U.S. patent application Ser. No. 09/348,940 filed Jul. 7, 1999 now U.S. Pat. No. 6,159,234, by Peter M. Bonutti, Matthew J. Cremens, and Ping Liu. The aforementioned U.S. patent application Ser. No. 09/348,940 is itself as continuation-in-part of U.S. patent application Ser. No. 08/905,084 filed Aug. 1, 1997 by Peter M. Bonutti, Matthew J. Cremens, and Ping Liu (now U.S. Pat. No. 6,010,525). The benefit of the earlier filing dates of the aforementioned Application Ser. Nos. 09/348,940 and 08/905,084 is claimed for all material common to this application and the aforementioned Application Ser. Nos. 09/348,940 and/or 08/905,084.

BACKGROUND OF THE INVENTION

The present invention relates to a new and improved method and apparatus for securing a suture against movement relative to body tissue by using a retainer to grip the suture.

Difficulty has been encountered in securing sutures against movement relative to body tissue. A knot may be tied in a suture to prevent loosening of the suture. However, the knot weakens a portion of the suture and reduces the overall force transmitting capability of the suture. In addition, a suture which is held by a knot applies force to a relatively small area of the body tissue and tends to cut or separate the body tissue. Many operations are conducted in very restricted space where the tying of a knot is difficult.

Various methods of securing a suture against movement relative to body tissue are disclosed in U.S. Pat. Nos. 3,513,848; 4,662,068; 4,935,028; 5,306,280; and 5,593,425. Although these and other known methods of securing a suture have, to a greater or lesser extent, been successful, it is desirable to simplify the securing of a suture against movement relative to body tissue. It is also desirable to be certain that the suture applies a desired amount of force to the body tissue when the suture is secured. The overall force transmitting capability of the suture should be maximized without concentrating the force at a small area on the body tissue.

SUMMARY OF THE INVENTION

The present invention provides a new improved method and apparatus for use of securing a suture relative to body tissue. A portion of the suture is enclosed with a first member. Although the first member may have many different configurations, in one embodiment of the invention, the first member has a tubular configuration. The first member is moved along the suture toward the body tissue with the suture extending through a passage in the first member. The first member is then deformed to change the configuration of the first member. The first member may be deformed by bending the first member to grip the suture which extends through the passage in the first member. The first member is retained in the bent configuration by a holder.

The holder may have many different constructions that may include either one part or a plurality of parts. In specific embodiments of the holder, the holder forms a recess. The first member is at least partially located in the recess in the holder. The holder applies force against the first member to maintain the first member in its second or bent configuration.

In one specific embodiment of the invention, the holder is formed as one piece. In another embodiment of the invention, the holder is formed by a plurality of pieces which are interconnected. The holder may be formed with a generally C-shaped configuration to form a recess in which the first member is inserted. Alternatively, the holder may be formed of a plurality of parts which are interconnected with the first member between the parts of the holder.

It is contemplated that, if desired, the suture retainer could include a first member which is deflected and subsequently released to grip a portion of the suture between the first member and a second member. The suture may be wound for one or more turns around the first member before the first member is released. The first member may be released in a recess formed in the second member to press the suture against the second member with the first member. Alternatively, the second member could be received in a recess in the first member and the suture pressed against the second member by the first member.

In still other embodiments of the invention, the retainer includes the first and second members which are movable relative to each other to grip the suture between the members. The members may have a tapered configuration and/or a thread convolution which grips the suture. Alternatively, the retainer could be formed with a plurality of fingers which extend into a plurality of recesses to grip the suture. A pair of cam members may be utilized to apply force against the suture to hold the suture.

A tissue fixation system constructed in accordance with one of the features of the present invention is used to connect thick and thin layers of tissue. The tissue fixation system is located equal distances from the ends of the thick and thin layers of tissue.

In should be understood that a suture retainer constructed in accordance with the present invention may have many different configurations. It should also be understood that a suture retainer constructed in accordance with the present invention could hold a suture in many ways. The invention should not, except as required by the claims, be limited to any specific construction of the retainer and/or manner of holding the suture.

BRIEF DESCRIPTION OF THE DRAWINGS

The foregoing and other features of the invention will become more apparent upon a consideration of the following description taken in connection with the accompanying drawings wherein:

FIG. 1 is a schematic illustration depicting the relationship of a suture retainer to a suture and body tissue prior to tightening of the suture;

FIG. 2 is an enlarged sectional view illustrating the manner in which the suture is wrapped around the suture retainer of FIG. 1 to form bends in the suture;

FIG. 3 is a schematic illustration depicting the manner in which the suture retainer of FIG. 2 is pressed against body tissue with a predetermined force and the manner in which a predetermined force is applied to an outer side surface of the suture retainer to plastically deform the suture retainer;

FIG. 4 is an enlarged fragmentary schematic illustration of a portion of FIG. 3 and depicting the manner in which the material of the suture retainer grips the suture;

FIG. 5 is an enlarged fragmentary view of a portion of FIG. 4 further illustrating the manner in which the material of the suture retainer grips the suture;

FIG. 9 is a schematic illustration depicting the manner in which a suture is wrapped around another embodiment of the suture retainer to form bends in the suture;

FIG. 10 is an enlarged fragmentary sectional view, taken generally along the line 10—10 of FIG. 9, illustrating the manner in which the suture is disposed in a groove in the suture retainer;

FIG. 11 is a fragmentary sectional view, generally similar to FIG. 10, illustrating an alternative configuration for the groove in the suture retainer of FIG. 9;

FIG. 12 is a schematic illustration depicting the manner in which force is applied against the suture retainer of FIG. 9 to plastically deform the suture retainer and grip the suture;

FIG. 29 is a schematic sectional view of another two-section embodiment of the suture retainer prior to engagement of the two sections of the suture retainer;

FIG. 30 is a schematic illustration of another two-section embodiment of the suture retainer;

FIG. 31 is a pictorial illustration of an inner member used in the suture retainer of FIG. 30;

FIG. 37 is an illustration of a chart of available suture sizes and known strengths for each suture size;

FIG. 38 is a schematic illustration depicting the manner in which a suture is tensioned, a suture retainer is pressed against body tissue, and force is applied against the suture retainer to plastically deform the suture retainer;

FIG. 40 is a schematic pictorial illustration of a holder which may be used with another embodiment of the suture retainer;

FIG. 41 is a schematic illustration depicting the relationship of a tubular member to a suture;

FIG. 42 is a schematic illustration depicting the manner which the holder of FIG. 40 engages the tubular member of FIG. 41 to retain the tubular member in a bent configuration;

FIG. 43 is a schematic illustration, generally similar to FIG. 41, of a second embodiment of the tubular member which may be used with a holder which has a construction similar to the construction of the holder of FIGS. 40 and 42;

FIG. 44 is a schematic illustration, generally similar to FIG. 42, illustrating the manner in which a holder is used to maintain a plurality of bends in a tubular member through which a suture extends;

FIG. 45 is a schematic pictorial illustration depicting the manner in which a suture retainer constructed in accordance with the present invention is pressed against body tissue and is utilized to maintain tension in a suture;

FIG. 48 is a plan view of a holder which is used in another embodiment of the suture retainer;

FIG. 49 is a sectional view taken generally along the line 49—49 of FIG. 48, further illustrating the construction of the holder;

FIG. 50 is a plan view of a resiliently deflectable member, illustrating the manner in which a suture is wound in a plurality of turns around the member;

FIG. 51 is a view taken generally along the line of 51—51 of FIG. 50, further illustrating the relationship between the resilient member and the suture;

FIG. 52 is a schematic illustration depicting the manner in which the resilient member of FIGS. 50 and 51 is held in a deflected condition by the holder of FIG. 48 to grip the suture between the holder and the resilient member;

FIG. 59 (on sheet 16 of drawings) illustrates a tissue fixation system used to interconnect thick and thin layers of tissue.

DESCRIPTION OF SPECIFIC PREFERRED EMBODIMENTS OF THE INVENTION

Embodiment of FIGS. 1–5

Figure 6:
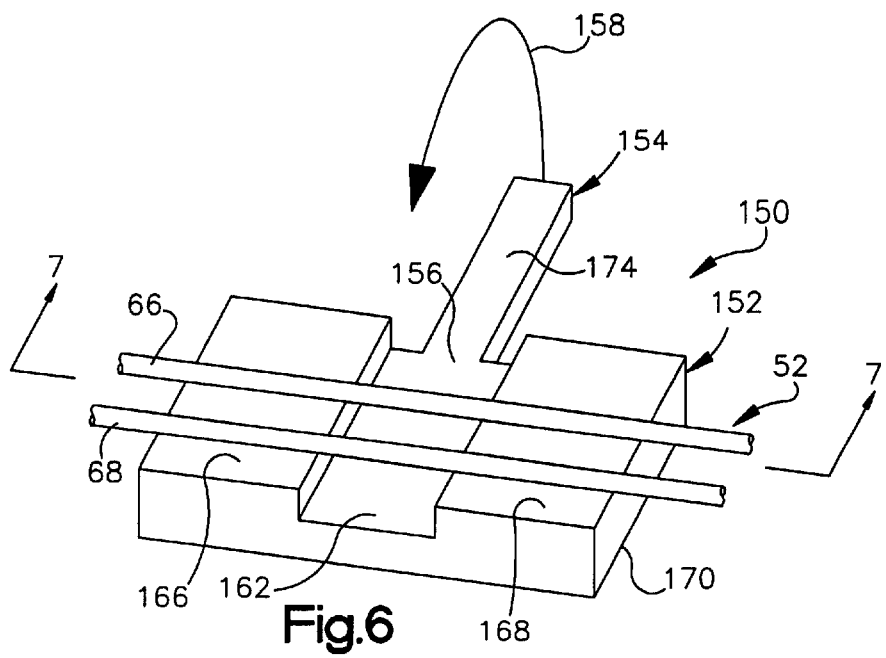
FIG. 6 is a schematic pictorial illustration depicting the manner in which a suture is positioned relative to a base of a second embodiment of the suture retainer.

A suture retainer 50 (FIG. 1) is utilized to secure a known suture 52 against movement relative to body tissue 54. The suture 52 extends through an outer layer 56 and an inner layer 58 of the body tissue. The suture 52 has been illustrated schematically in FIG. 1 as extending through passages 60 and 62 in the outer and inner layers 56 and 58 of body tissue 54. However, the suture 52 could be sewn through the body tissue without forming the passages 60 and 62 in the body tissue.

Although the suture 52 has been shown in FIG. 1 in association with soft body tissue, it is contemplated that the suture 52 could be associated with hard body tissue. It is also contemplated that the suture 52 could extend through a suture anchor in a manner similar to that disclosed in U.S. Pat. Nos. 5,584,862; 5,549,631; and/or 5,527,343.

The suture 52 has a left section 66 and a right section 68. The left and right sections 66 and 68 of the suture 62 extend through the suture retainer 50 (FIG. 2). If desired, the suture 52 could be integrally formed as one piece with the suture retainer 50. If this was done, an end of one of the sections 66 or 68 of the suture 52 would be connected with the suture retainer 50.

Although the sections 66 and 68 of the suture 52 could extend straight through the suture retainer 50, it is preferred to form a plurality of bends in the suture 52. In the illustrated embodiment of the invention, two bends 72 and 74 (FIG. 2) are formed in the left section 66 of the suture 52. Similarly, two bends 76 and 78 are formed in the right section 66 of the suture 52. If desired, a greater or lesser number of bends could be formed in each of the sections 66 and 68 of the suture 52.

The bends 72 and 74 (FIG. 2) are formed in the left section 66 of the suture 52 by wrapping a turn 82 in the left section of the suture around a portion of the suture retainer 50. Similarly, the bends 76 and 78 are formed in the right section 68 of the suture 52 by wrapping a turn 84 in the right section of the suture around a portion of the suture retainer 50. A single loop 86 is formed in the left section 66 of the suture 52 around a portion of the suture retainer. Similarly, a single loop 88 is formed in the right section 68 of the suture 52 around a portion of the suture retainer 50. A greater or lesser number of loops could be provided in the left and right sections 66 and 68 of the suture 52 if desired.

The suture retainer 50 has a spherical configuration. A cylindrical passage 92 extends through the center of the spherical suture retainer 50. If desired, the suture retainer 50 could have a different configuration. For example, the suture retainer 50 could have an oval or elliptical configuration. Although the passage 92 has a linear central axis, the passage could have a nonlinear central axis. If desired, a plurality of passages, having the same or different configurations, could be provided in the suture retainer 50.

The left and right sections 66 and 68 of the suture 52 extend through the passage 92. In addition, the left and right sections 66 and 68 of the suture 52 extend around a spherical outer side surface 94 of the suture retainer 50. Thus, the loop 86 in the left section 66 of the suture 52 extends around a left (as viewed in FIG. 2) hemispherical portion of the suture retainer 50. Similarly, the loop 88 extends around a right hemispherical portion of the suture retainer 50.

In the illustrated embodiment of the suture retainer 50, the left and right sections 66 and 68 of the suture 52 engage the smooth spherical outer side surface 94 of the suture retainer 50. However, it is contemplated that grooves could be provided in the outside of the suture retainer 50 to receive the turns 82 and 84 of the left and right sections 66 and 68 of the suture 52. Alternatively, projections could extend from the spherical outer side surface 94 of the suture retainer 50 to engage the suture 52.

After the suture 52 has been inserted through the suture retainer 50, in the manner illustrated schematically in FIG. 2, the suture retainer 50 is moved along the left and right sections 66 and 68 of the suture toward the body tissue 54 (FIG. 1). To move the suture retainer 50 along the left and right sections 66 and 68 of the suture 52, the left and right sections 66 and 68 of the suture are pulled upward (as viewed in FIGS. 1 and 2) to tension the sections of the suture. A downward (as viewed in FIG. 1) force is then applied against the suture retainer 50. This downward force causes the suture retainer 50 to slide in a downward direction along the suture 52 toward an upper side surface 98 of the body tissue 54 (FIG. 1).

As the suture retainer 50 slides downward along the left and right sections 66 and 68 of the suture 52, force is applied against the left section 66 of the suture 52 at the bend 74. This force causes loop 86 in the left section 66 of the suture 52 to move downward (as viewed in FIG. 2) along the left section of the suture. At the same time, force is applied against the right section 68 of the suture 52 at the bend 78. This force causes the loop 88 in the right section 68 of the suture 52 to move downward along the right section of the suture.

The suture retainer 50 is formed as one piece of a polymeric material having a relatively low coefficient of friction. Therefore, the two sections 66 and 68 of the suture 52 can readily slide along the outer side surface 94 and through the passage 92 in the suture retainer 50 as the suture retainer is moved downward toward the upper side surface 98 (FIG. 1) of the body tissue 54.

While a predetermined tension is maintained in the left and right sections 66 and 68 of the suture 52, the suture retainer 50 is pressed against the upper side surface 98 of the body tissue 54 (FIG. 3). This results in a connector section 102 (FIG. 1) of the suture 52 being pulled tightly against the inner layer 58 of body tissue. In order to obtain a desired tension in the left and right sections 66 and 68 and connector section 102 of the suture 52, the suture retainer 50 is pressed against the upper side surface 98 of the body tissue with a predetermined force, indicated schematically by an arrow 104 in the FIG. 3. The suture retainer 50 increases the surface area on the body tissue 54 against which force is applied.

Thus, while pulling on upper end portions of the left and right sections 66 and 68 of the suture 52 with a predetermined force, the suture retainer 50 is slid downward (as viewed in FIG. 1) along the left and right sections of the suture. The suture retainer 50 is pressed against the body tissue 54 with a predetermined force 104 (FIG. 3) which is sufficient to obtain a desired tension in the left and right sections 66 and 68 and connector section 102 of the suture 52. In this manner, a desired force, which has been preselected, is applied against the body tissue 54 by the suture 52 and suture retainer 50.

Although the suture retainer 50 applies force against a is far greater surface area on the body tissue 54 than would be engaged by a know in the suture 52, a force distribution member or button may be placed between the suture retainer and the upper surface 98 of the body tissue. A second force distribution member or button may be placed between the connector section 102 of the suture and a lower side surface 108 (FIG. 1) of the body tissue 54. If this is done, the main area of engagement of the suture 52 with the body tissue 54 would be at the passages 60 and 62.

In accordance with a feature of the present invention, once the suture retainer 50 has been moved along the suture 52 and is being pressed against the body tissue 54 with a predetermined force 104 (FIG. 3), the suture retainer is plastically deformed to grip the left and right sections 66 and 68 of the suture. While the suture retainer 50 is being pressed against the body tissue 54 with the predetermined force 104 and the left and right sections 66 and 68 of the suture are being tensioned, a pair of force application members 112 and 114 are pressed against opposite sides of the suture retainer 50. The force applied against the suture retainer 50 by the force application members 112 and 114 plastically deforms the material of the suture retainer.

The plastic deformation of the suture retainer 50 is effective to cause cold flowing of material of the suture retainer. Force indicated by arrows 118 and 120 in FIG. 3, is applied against the suture retainer 50 by the force application members 112 and 114. This force is effective to cause flowing of the material of the suture retainer 50 at a temperature below a transition temperature range for the material of the suture retainer. Although the illustrated force application members 112 and 114 have flat force transmitting surfaces, each of the force application members could have force transmitting surfaces with a configuration corresponding to the configuration of a portion of a sphere.

The cold flowing of the material of the suture retainer 50 results in a collapsing of the passage 92 (FIG. 2) and in flowing of the material of the suture retainer 50 around the sections 66 and 68 of the suture 52. This enables the material of the suture retainer 50 to bond to and obtain a firm grip on the suture 52. The cold flowing of the material of the suture retainer 50 occurs at a temperature which is below the transition temperature of the material forming the suture retainer.

In the illustrated embodiment of the suture retainer 50, the material of the suture retainer flows around and grips the portion of the suture which was disposed in the passage 92. In addition, the force applied against the turns 82 and 84 by the force application members 112 and 114 is sufficient to embed the turns 82 and 84 of the suture 52 in the material of the suture retainer 50 to further grip the suture. If the turns 82 and 84 are disposed in grooves in the outside of the suture retainer, the material of the suture retainer would more firmly grip the portion of the suture 52 forming the turns 82 and 84. If desired, grooves could be formed in the cylindrical side surface of the passage 92 to receive the sections 66 and 68 of the suture 52.

A transducer or load cell 114 (FIG. 3) is connected with the force application member 112 to measure the amount of force, indicated by the arrows 118 and 120, which is applied against the suture retainer 50. A display unit 126 is connected with the load cell 124 and provides an output indicative of the force being applied against opposite sides of the suture retainer 50 by the force application members 112 and 114. After a predetermined minimum force has been applied against the suture retainer 50 for a predetermined minimum time by the force application members 112 and 114, an output from the display unit 126 activates an indicator 130 to indicate to a surgeon that the desired plastic deformation of the suture retainer 50 has occurred. The force application members 112 and 114 can then be withdrawn from the suture retainer 50.

During the time in which the force application members 112 and 114 are applying the clamping forces 118 and 120 against opposite sides of the suture retainer 50, the suture retainer is pressed against the upper side surface 98 of the body tissue 54 with a predetermined force, indicated at 104 in FIG. 3. In addition, a predetermined tension is maintained in sections 66 and 68 of the suture 52 extending upward from the suture retainer 50. Upon disengagement of the force application members 112 and 114 from the suture retainer 50, the application of the downward (as viewed in FIG. 3) force 104 against the suture retainer 50 is interrupted. The upward tensioning of the sections 66 and 68 of the suture 52 is also interrupted.

The application of the clamping forces 118 and 120 against opposite sides of the suture retainer 50 causes cold flowing of the material of the suture retainer. As this occurs, the material of the suture retainer 50 moves between and extends around the portions of the left and right sections 66 and 68 of the suture 52 disposed in the passage 92 (FIG. 2). Thus, a portion 134 (FIGS. 2 and 4) and a portion 136 of the left section 66 of the suture 52 are fully enclosed by the material of the suture retainer 50. A cold bonding of the material of the suture retainer 50 with the exterior surfaces of the portions 134 136 of the left section 66 of the suture retainer securely interconnects the material of the suture retainer and the suture 52.

Similarly, the portions 138 and 140 of the right section 68 of the suture 52 disposed in the passage 92 (FIG. 2) are surrounded by and bonded with the material of the suture retainer 50 (FIG. 4). The manner in which the material of the suture retainer 50 extends completely around and is connected with the length or portion 138 of the right section 68 of the suture 52 is illustrated schematically in FIG. 5. It should be understood that the permanent deformation of the material of the suture retainer 50 occurs as a result of compression of the material of the suture retainer while the material is at a temperature close to the temperature of the body tissue 54. This temperature is below the transition temperature for the material of the suture retainer 50.

Once the suture retainer 50 has been plastically deformed to securely grip the suture 52, the suture may be knotted if desired. Thus, a knot may be formed between the portions of the sections 66 and 68 of the suture 52 which extend upward (as viewed in FIGS. 1–3) from the retainer 50. Such a knot would provide additional protection against the suture working loose under the influence of varying loads over an extended period of time. Since the suture retainer 50 is disposed between the knot and the body tissue 54, the knot will not reduce the overall force transmitting capability of the suture 52. However, it is believed that forming a knot in the sections 66 and 68 of the suture 52 adjacent to the upper end of the suture retainer 50 will not be necessary.

The suture retainer 50 may be formed of many different materials. However, it is believed that it will be preferred to form the suture retainer 50 of a biodegradable polymer. One biodegradable polymer which may be utilized is polycaperlactone. Alternatively, the suture retainer 50 could be formed of polyethylene oxide terephthalate or polybutylene terephthalate. It is also contemplated that other biodegradable or bioerodible copolymers could be utilized if desired.

Although it is preferred to form the suture retainer 50 of a biodegradable material, the suture retainer could be formed of a material which is not biodegradable. For example, the suture retainer could be formed of an acetyl resin, such as "Delrin" (trademark). Alternatively, the suture retainer 50 could be formed of a para-dimethylamino-benzenediazo sodium sulfonate, such as "Dexon" (trademark).

It is preferred to effect the cold flowing of the material of the suture retainer 50 without the addition of heat. However, it is contemplated that the suture retainer 50 could be heated to a temperature which is somewhat above the temperature of the body tissue 54. If desired, heat could be transmitted to the suture retainer 50 through the force application members 112 and 114 (FIG. 3). Although the suture retainer 50 may be heated, the suture retainer would be maintained at a temperature below the transition temperature for the material of the suture retainer.

In the illustrated embodiment of the invention, the suture 52 is separate from the suture retainer 50. However, one of the sections 66 or 68 of the suture 52 could be fixedly connected with the suture retainer 50. This could be accomplished with a suitable fastener or by forming the suture 52 integrally as one piece with the suture retainer. This would result in the suture retainer 50 sliding along only one of the sections 66 or 68 of the suture 52.

The suture 52 may be formed of natural or synthetic materials. The suture 52 may be a monofilament or may be formed of a plurality of interconnected filaments. The suture 52 may be biodegradable or nonbiodegradable. It may be preferred to form the suture 52 of the same material as the suture retainer 50. However, the suture 52 could be formed of a material which is different than the material of the suture retainer.

The use of the suture retainer 50 eliminates the necessity of forming a knot in the suture 52. By eliminating the formation of a knot in the suture 52, the overall force transmitting capability of the suture is increased. In addition to increasing the overall force transmitting capability of the suture 52, the suture retainer 50 increases the surface area on the body tissue 54 (FIG. 1) against which force is applied by the suture. This tends to minimize any tendency for the suture 52 to cut or separate the body tissue.

It is believed that it may be preferred to position the left and right sections 66 and 68 of the suture 52 relative to the body tissue 54 (FIG. 1) before winding the two sections of the suture around the suture retainer 50. However, one of the sections 66 or 68 of the suture 52 may be wound around the suture retainer 50 before the suture is positioned in the passages 60 and 62 in the body tissue 54. For example, the left section 66 of the suture 52 may e wound around the suture retainer 52 to form the bends 72 and 74 and the loop 86 (FIG. 2) while the suture is spaced from the body tissue 54. The right section 68 of the suture is then inserted through the passages 60 and 62 (FIG. 1) in the body tissue 54. The right section 68 of the suture 52 is then wound around the suture retainer 50 to form the bends 76 and 78 and loop 88 (FIG. 2).

Figure 7:
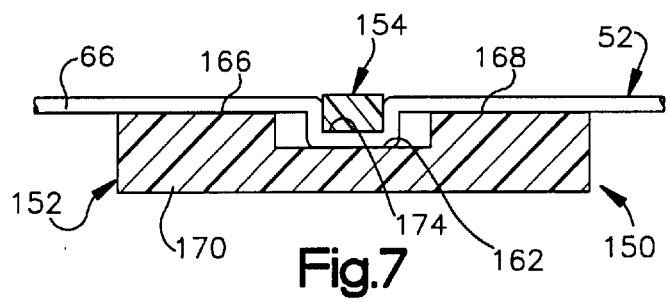
FIG. 7 is a schematic illustration, taken along the line 7—7 of FIG. 6, depicting the manner in which a movable arm presses a portion of the suture into a groove formed in the base of the suture retainer to form bends in the suture.
Figure 8:
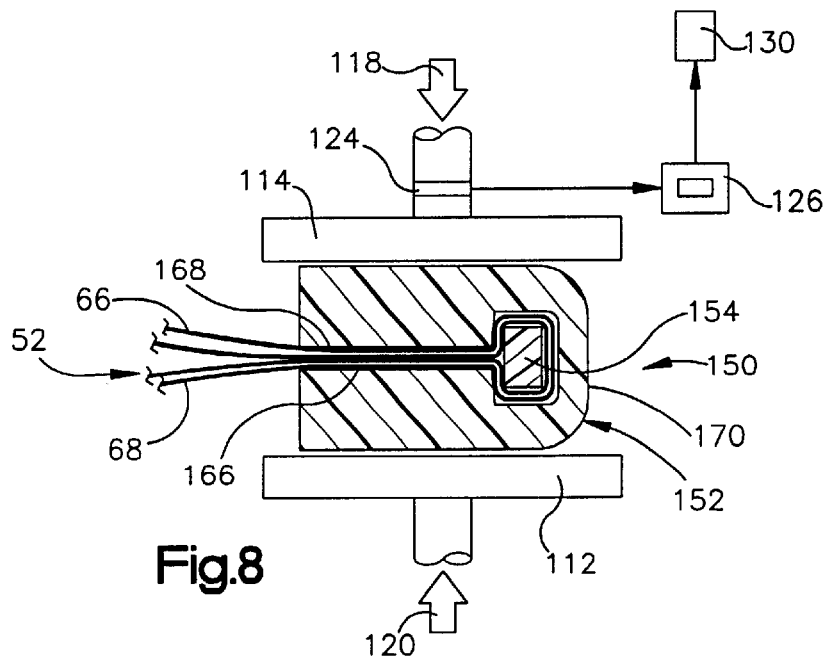
FIG. 8 is a schematic illustration depicting the manner in which force is applied against the suture retainer of FIGS. 6 and 7 to plastically deform the suture retainer.

Embodiment of FIGS. 6–8

In the embodiment of the invention illustrated in FIGS. 1–5, complete loops 86 and 88 are formed in the sections 66 and 68 of the suture 52. In the embodiment of the invention illustrated in FIGS. 6–8, partial loops are formed in each of the sections of the suture. Since the embodiment of the invention illustrated in FIGS. 6–8 is similar to the embodiment of the invention illustrated in FIGS. 1–5, similar terminology will be utilized to identify similar components. It should be understood that one or more features of the embodiment of the invention illustrated in FIGS. 1–5 may be used with the embodiment of the invention illustrated in FIGS. 6–8.

A suture retainer 150 is utilized to secure a suture 52 against movement relative to body tissue. The suture 52 has sections 66 and 68 which engage body tissue in the same manner as previously described in conjunction with the embodiment of the invention illustrated in FIGS. 1–5. Although the suture 52 is illustrated in FIG. 1 in association with soft body tissue, it is contemplated that the suture 52 could be utilized in association with hard body tissue and/or one or more suture anchors.

The suture retainer 150 includes a rectangular base or body section 152 and a movable post or locking section 154. The post or locking section 154 is integrally formed as one piece with the base 152. The post or locking section is hingedly connected with the base 152 at a connection 156. The post 154 is pivotal relative to the base at the connection 156 in the manner indicated schematically by the arrow 158 in FIG. 6.

The base 152 has a central groove 162 which is aligned with the post 154. The groove 162 has a rectangular cross sectional configuration. The groove 162 has a cross sectional area which is greater than the cross sectional area of the post 154. In the illustrated embodiment of the suture retainer 150, the post 154 and groove 162 both have a rectangular cross sectional configuration. However, the post and groove could have a different cross sectional configuration if desired. For example, the post 154 and groove 162 could have a semicircular cross sectional configuration.

The base 152 has a pair of flat rectangular upper (as viewed in FIGS. 6 and 7) side surfaces 166 and 168. The flat side surfaces 166 and 168 extend in opposite directions from the groove 162 and extend parallel to a flat rectangular bottom surface 170. The suture retainer 150 is formed from a single piece of a biodegradable polymer, such as polycaperlactone. Of course, other biodegradable or bioerodible copolymers could be utilized to form the suture retainer 150. It is contemplated that the suture retainer 150 may be formed of materials which are not biodegradable.

When the suture retainer 150 is to be utilized to hold the sections 66 and 68 of the suture 52 against movement relative to body tissue, the post 154 is pivoted from its initial or extended position, shown in FIG. 6, to its engaged or locking position, shown in FIG. 7. As the post 154 is pivoted to the engaged position of FIG. 7, a flat side surface 174 of the post is pressed against the sections 66 and 68 of the suture to force the sections into the groove 162. The post is effective to clamp or hold the sections 66 and 68 of the suture 52 against movement relative to the base 152 upon movement of the post to the engaged position shown in FIG. 7.

Once the post 154 has been moved to the engaged position shown in FIG. 7, the base 152 is bent from the flat orientation of FIGS. 6 and 7 to the folded orientation of FIG. 8. Once the base 152 has been folded, a pair of force application members 112 and 114 engage opposite sides of the bottom or outer surface 170 of the base. The force application members 112 and 114 are then pressed toward each other, in the manner indicated schematically by the arrows 118 and 120 in FIG. 8, to apply pressure against the suture retainer 150.

At this time, the suture retainer 150 is at a temperature below the transition temperature of the material forming the suture retainer. Thus, the suture retainer 150 is at a temperature which is approximately the same as the temperature of the body tissue relative to which the suture retainer 150 is being utilized to secure the suture 52. The force applied against the suture retainer 150 by the force application members 112 and 114 plastically deforms the material of the suture retainer. This results in a cold flowing of the material of the suture retainer 150 under the influence of the force applied against the suture retainer by the force application members 112 and 114.

A transducer or load cell 124 measures the force 118 and 120 applied against the base 152 of the suture retainer 150. The load cell 124 provides an output signal to a display unit 126. The output signal provided by the transducer 124 corresponds to the magnitude of the force applied against opposite sides of the suture retainer 150 by the members 112 and 114.

After a predetermined minimum force has been applied against opposite sides of the suture retainer 150 for a sufficient period of time to effect a cold flowing of the material of the suture retainer, an output signal from the display unit 126 activates an indicator 130. The output from the indicator 130 indicates to a surgeon and/or other medical personnel that the force has been applied against opposite sides of the suture retainer 150 by the force application members 112 and 114 for a period of time sufficient to cause cold flowing of the material of the suture retainer. The cold flowing of the material of the suture retainer 150 results in a secure interconnection between the material of the suture retainer 150 and the sections 66 and 68 of the suture 52.

In the embodiment of the invention illustrated in FIGS. 6–8, the suture 52 is separate from the suture retainer 150. However, the suture 52 could be fixedly connected to or integrally formed as one piece with the suture retainer 150. For example, the base 152 could be integrally formed with the section 66 of the suture 52 if desired.

Embodiment of FIGS. 9–12

In the embodiment of the invention illustrated in FIGS. 1–5, the sections 66 and 68 of the suture 52 extend through a passage formed in a spherical suture retainer 50. In the embodiment of the invention illustrated in FIGS. 9–12, the sections of the suture extend along a groove formed in the outside of a suture retainer. Since the embodiment of the invention illustrated in FIGS. 9–12 is similar to the embodiment of the invention illustrated in FIGS. 1–5, similar terminology will be utilized to identify similar components. It should be understood that one or more features of the embodiments of the invention illustrated in FIGS. 1–8 may be used with the embodiment of the invention illustrated in FIGS. 9–12.

A suture retainer 180 (FIG. 9) is utilized to secure a suture 52 against movement relative to body tissue 54. Although the body tissue 54 is soft body tissue, it is contemplated that the suture retainer 180 could be utilized to secure the suture 52 against movement relative to hard body tissue, such as bone. The suture retainer 180 may be used either with or without a suture anchor.

The suture retainer 180 has a cylindrical main section or body 184. The body 184 has a cylindrical outer side surface 186. Flat circular end surfaces 188 and 190 extend perpendicular to a longitudinal central axis of the cylindrical side surface 186. In the illustrated embodiment of the suture retainer 180, the body 184 is cylindrical and has a linear longitudinal central axis. If desired, the body 184 could be rectangular and/or have a nonlinear longitudinal central axis.

A helical groove 194 is formed in the body 184. The helical groove 194 has a constant pitch. Therefore, turns of the groove 194 are equally spaced. However, if desired, the pitch of the turns of the groove 194 could vary along the length of the body 184.

The helical groove 194 has a central axis which is coincident with the central axis of the body 184 and cylindrical outer side surface 186 of the suture retainer 180. A radially inner portion of the helical groove 194 defines a right circular cylinder which is coaxial with the outer side surface 186 of the body 184. However, the radially inner portion of the helical groove 194 could define a right circular cone or other configuration if desired.

The left and right sections 66 and 68 of the suture 52 extend through the groove 194 and around body tissue 54. It is believed that it will be advantageous to provide the helical groove 194 with retainers or bridge sections 198 and 200 which extend across the open ends of the helical groove. The bridge sections 198 and 200 are integrally formed as one piece with the body 184. The bridge sections 198 and 200 prevent the sections 66 and 68 of the suture 52 from pulling out of the helical groove 194 during positioning of the suture retainer 180 in a human patient's body. However, the bridge sections 198 and 200 may be omitted if desired.

The helical groove 194 has a generally U-shaped cross sectional configuration (FIG. 10). Thus, the helical groove 194 has an open mouth or entrance 204. A pair of side surfaces 206 and 208 slope radially inward and axially upward (as viewed in FIGS. 9 and 10) from the entrance 204. An arcuate bottom surface 210 of the groove 194 extends between the side surfaces 206 and 208.

The section 66 of the suture 52 is disposed in engagement with the bottom surface 210 of the helical groove 194. The section 68 of the suture 52 is disposed in engagement with the section 66 of the suture (FIG. 10). If desired, the size of the arcuate bottom surface 210 of the groove 194 could be increased to enable both sections 66 and 68 of the suture 52 to engage the bottom surface.

The groove 194 may be provided with a configuration similar to the configuration shown in FIG. 11. Thus, in FIG. 11, the side surfaces 206 and 208 of the helical groove 194 extend inward from the open entrance 204 to an arcuate bottom surface 210 which forms a major portion of a circle. The bottom surface 210 of FIG. 11 defines a recess 214 in which the two sections 66 and 68 of the suture are disposed. It is believed that the bridge sections 198 and 200 will probably be omitted with the embodiment of the groove 194 illustrated in FIG. 11.

The cylindrical body 184 of the suture retainer 180 is molded from a single piece of a biodegradable polymer. For example, the body 184 of the suture retainer 180 may be molded from polycaperlactone. Alternatively, the body 184 of the suture retainer 180 could be molded of polyethylene oxide terephthalate or polybutylene terephthalate. Of course, the body 184 of the suture retainer 180 could be molded as one piece of other biodegradable or bioerodible copolymers if desired. Although it is preferred to form the body 184 of biodegradable materials, the body could be formed of materials which are not biodegradable. For example, the body 184 could be formed of "Delrin" (trademark).

The left and right sections 66 and 68 (FIG. 9) of the suture 52 are inserted into the helical groove 194 in the body 184 of the suture retainer 180. At this time, the body 184 of the suture retainer 180 is spaced from the body tissue 54. It is believed that insertion of the left and right sections 66 and 68 of the suture 52 into the helical groove 194 will be facilitated if the bridge sections 198 and 200 are omitted. However, if the bridge sections 198 and 200 are omitted, difficulty may be encountered in maintaining the sections 66 and 68 of the suture 52 in the helical groove 194.

As the left and right sections 66 and 68 of the suture 52 are inserted into the helical groove 194 (FIG. 9), the sections of the suture are wrapped around the body 184 of the suture retainer 180. As this occurs, a plurality of helical loops are formed in the left and right sections 66 and 68 of the suture 52. Once the suture 52 has been inserted into the helical groove 194, a plurality of circular turns are maintained in the left and right sections 66 and 68 of the suture 52 by the helical groove 194. Therefore, a continuous series of smooth arcuate bends, which are free of stress inducing discontinuities, is maintained in the suture 52 by the helical groove 194.

After the suture 52 has been inserted into the helical groove 194, the suture retainer 180 is moved along the suture toward the body tissue 54 (FIG. 9). During this movement of the suture retainer 180 along the suture 52, the left and right sections 66 and 68 of the suture are tensioned. The radially inward and axially upward sloping configuration of the helical groove 194 (FIGS. 10 and 11) results in the left and right sections 66 and 68 of the suture being pulled toward the arcuate bottom surface 210 of the groove. This results in the body 184 of the suture retainer 180 maintaining the helical loops in the left and right sections 66 and 68 of the suture 52 as the suture retainer 180 moves toward the body tissue 54.

As the suture retainer 180 moves toward the body tissue 54 (FIG. 9), the left and/or right sections 66 and 68 of the suture 52 slide along the arcuate bottom surface 210 (FIG. 10) of the groove 194. The groove 194 imparts a helical configuration to the portion of the suture 52 disposed in the groove. As the body 184 of the suture retainer 180 moves downward toward the body tissue 54, the portion of the suture 52 having a helical configuration moves downward toward the body tissue.

As the suture retainer 180 is slid along the tensioned sections 66 and 68 of the suture 52, the tensioning force in the suture pulls the suture toward the bottom surface 210 of the helical groove 194. The biodegradable copolymer forming the body 184 of the suture retainer 180 has a low coefficient of friction. This minimizes the force 220 required to move the suture retainer along the left and right sections 66 and 68 of the suture 52 toward the body tissue 54.

The suture retainer 180 is moved along the taut left and right sections 66 and 68 of the suture 52 until the leading end surface 190 of the body 184 of the suture retainer 180 engages the body tissue 54 (FIG. 9). The force 220 is then increased to a predetermined magnitude while maintaining a predetermined tension in the left and right sections 66 and 68 of the suture 52. This results in the suture 52 being pulled tightly around the body tissue and exerting a predetermined force against the body tissue.

It is contemplated that the magnitude of the force 220 (FIG. 9) with which the suture retainer 190 is pressed against the body tissue 54 will be measured to be certain that the force has a desired magnitude. The force 220 may be measured with a suitable transducer, such as a load cell or a force measuring device having a spring which is compressed to a predetermined extent by the application of the desired force against the body tissue 54. Rather than engaging the body tissue 54 directly with the leading end surface 190 of the suture retainer 180, a suitable force transmitting member, such a button, could be provided between the suture retainer and the body tissue.

While the suture retainer 180 is being pressed against the body tissue 54 with the predetermined force 220 and the sections 66 and 68 of the suture 52 are being tensioned with a predetermined force, the left and right sections 66 and 68 of the suture 52 are gripped by plastically deforming the material of the suture retainer. To plastically deform the material of the suture retainer, a plurality of force application members 224, 226 and 228 (FIG. 12) are pressed against the cylindrical outer side surface 186 of the suture retainer 180. Since the outer side surface 186 of the suture retainer 180 has a cylindrical configuration, the force application members 224, 226 and 228 have an arcuate configuration and are formed as portions of a circle. However, the force application members 224, 226 and 228 could have the flat configuration of the force application members 112 and 114 of FIG. 3.

The force application members 224, 226 and 228 are pressed against the outer side surface 186 of the suture retainer 180 with a predetermined force, indicated by the arrows 232 in FIG. 12. This force has a magnitude and is applied for a length of time sufficient to cause cold flowing of the material of the body 184 of the suture retainer 180. The plastic deformation of the material of the body 194 of the suture retainer 180 results in the helical groove 194 being collapsed and the material of the suture retainer being pressed against the left and right sections 66 and 68 of the suture 52. The resulting cold bonding of the material of the suture retainer 180 with the left and right sections 66 and 68 of the suture 52 secures in the suture retainer against movement relative to the suture.

The cold flowing of the material of the body 184 of the suture retainer 180 occurs with the body of the suture retainer at substantially the same temperature as the temperature of the body tissue 54 (FIG. 9). Thus, the cold flowing of the material of the body 184 of the suture retainer 180 occurs at a temperature below the transition temperature of the material forming the body 184 of the suture retainer 180. However, if desired, some heat may be added to the body 184 to facilitate plastic deformation of the body of the suture retainer 180.

The suture retainer 180 eliminates the necessity of forming a knot in the suture 52. The formation of a knot in the suture 52 would cause a stress concentration in the suture and would decrease the overall force transmitting capability of the suture. By eliminating the knot, the overall force transmitting capability of the suture 52 is increased. However, if desired, a knot could be formed in the sections 66 and 68 of the suture 52 at a location above (as viewed in FIG. 1) the suture retainer 180. Since the suture retainer 180 would be disposed between this knot and the body tissue 54, the knot would not decrease the overall force transmitting capability of the suture 52.

In the embodiment of the invention illustrated in FIGS. 9–12, a single helical groove 194 is formed in the body 184 of the suture retainer 180. It is contemplated that a pair of spaced apart helical grooves could be formed in the body 184 of the suture retainer 180. If this was done, the two helical grooves would be wrapped in the same direction around the body 184 of the suture retainer 180 and would be offset from each other by 180N about the circumference of the cylindrical body of the suture retainer. The left section 66 of the suture 52 would be disposed in one of the helical grooves and the right section 68 of the suture would be disposed in the other helical groove.

By having a pair of spaced apart helical grooves in the body 184 of the suture retainer 180, in the manner set forth in the preceding paragraph, the left and right sections 66 and 68 of the suture 52 would exit from the lower (as viewed in FIG. 9 end of the suture retainer at diametrically opposite locations on the circular end surface 190. This embodiment of the suture retainer 180 would have the advantage of having a relatively large area of engagement with the body tissue 54. Thus, the tension in the suture would press the flat circular end surface 190 on the suture retainer against the body tissue.

In the illustrated embodiment of the invention, the suture 52 is separate from the suture retainer 180. However, if desired, the suture 52 could be fixedly connected with or integrally formed as one piece with the suture retainer. For example, the left section 66 of the suture 52 could be fixedly connected with the body 184 of the suture retainer 180 by a suitable fastener. If this was done, only the right section 68 of the suture 52 would be received in the groove 194.

Embodiment of FIGS. 13–16

In the embodiment of the invention illustrated in FIGS. 9–12, the left and right sections 66 and 68 of the suture 52 are wrapped in the same direction around the cylindrical body 184 of the suture retainer 180. In the embodiment of the invention illustrated in FIGS. 13–16, the sections of the suture are wrapped in opposite directions around a conical body of a suture retainer. Since the embodiment of the invention illustrated in FIGS. 13–16 is similar to the embodiment of the invention illustrated in FIGS. 9–12, similar terminology will be utilized to identify similar components. It should be understood that one or more features of the embodiments of the invention illustrated in FIGS. 1–12 may be used with the embodiments of the invention illustrated in FIGS. 13–16.

A suture 52 (FIG. 13) has left and right sections 66 and 68 which are wrapped in opposite directions around a conical body 242 of a suture retainer 244. Thus, as viewed from above, the left section 66 of the suture 52 is wrapped in a counterclockwise direction around the body 242 of the suture retainer 244. The right section 68 of the suture 52 is wrapped in a clockwise direction around the body 242 of the suture retainer 244.

The left and right sections 66 and 68 of the suture 52 are wrapped for approximately 1½ turns around the body 242 of the suture retainer 244. Therefore, the left section 66 of the suture 52 moves from the left side of the upper end (as viewed in FIG. 13) of the body 242 of the suture retainer 244 to the right side of the lower end of the body of the suture retainer. Similarly, the right section 68 of the suture 52 moves from the upper right side of the body 242 of the suture retainer 244 to the lower left side of the body of the suture retainer.

If the two sections 66 and 68 of the suture 52 were wrapped around the body 242 of the suture retainer 244 for complete turns, the sections of the suture would be on the same side of the body 242 at the top and bottom of the suture retainer. For example, if the suture 52 was wrapped two complete turns around the body 242, the left section 66 of the suture 52 would be disposed at the left side of both the upper and lower ends of the body 242. Similarly, the right section 68 of the suture 52 could be disposed at the right side of both the upper and lower ends of the body 242 of the suture retainer.

The body 242 of the suture retainer 244 is formed as a portion of a right circular cone. The body 242 of the suture retainer 244 has an outer side surface 248 with an axially downward (as viewed in FIG. 13) and radially inward tapering configuration. The conical body 242 of the suture retainer 244 has parallel circular end surfaces 252 and 254 which extend perpendicular to a longitudinal central axis of the conical body. The circular end surfaces 252 and 254 are disposed in a coaxial relationship. The upper end surface 252 has a larger diameter than the lower end surface 254.

A pair of helical grooves 258 and 260 (FIGS. 13–16) are formed in the conical body 242. The helical grooves 258 and 260 have a spiral configuration with a central axis which is coincident with the central axis of the conical body 242. Thus, the diameter of the turns of the grooves 258 and 260 progressively decreases as the grooves extend downward (as viewed in FIG. 13) from the upper end surface 252 to the lower end surface 254. The helical grooves 258 and 260 have the same pitch.

The helical grooves 258 and 260 are wrapped in opposite directions around the conical body 242 of the suture retainer 244. Thus, as viewed from above, the helical groove 258 is wrapped in a counterclockwise direction around the body 242 of the suture retainer 244. The helical groove 260 is wrapped in a clockwise direction around the body 242 of the suture retainer 244.

The helical grooves 258 and 260 are offset by 180N. Thus, the helical groove 258 beings at the upper left (as viewed in FIG. 13) side of the body 242 and the helical groove 260 begins at the upper right side of the body 242. The entrances to the helical grooves 258 and 260 are disposed at diametrically offset locations on the circular upper end surface 252 of the body 242. The helical groove 258 ends at the lower right (as viewed in FIG. 13) side of the body 242. The helical groove 260 ends at the lower left side of the body 242. The exits from the helical grooves 258 and 260 are disposed at diametrically offset locations on the circular lower end surface 254 of the body 242. This results in the relatively large lower end surface 254 of the body 242 being disposed between the left and right sections 66 and 68 of the suture 52 and exposed to body tissue.

Figure 14:
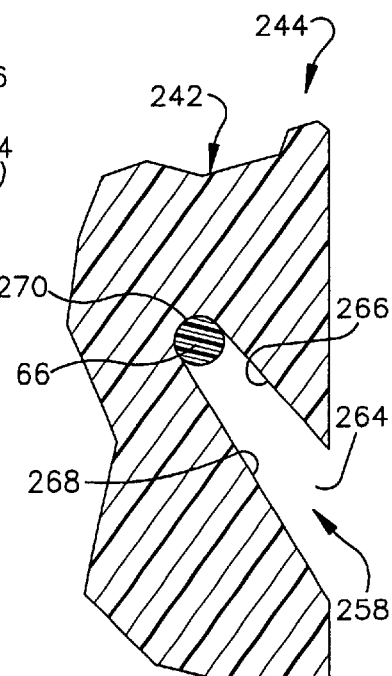
FIG. 14 is a sectional view, taken generally along the line 14—14 of FIG. 13, illustrating the manner in which the suture is disposed in a groove in the suture retainer.

The groove 258 has an axially upward and radially inward sloping configuration (FIG. 14). The groove 258 has a helical open mouth or entrance 264. The groove 258 has a pair of axially upward and radially inward sloping side surfaces 266 and 268. The side surfaces 266 and 268 are interconnected by an arcuate bottom surface 270. The groove 258 has the same depth and cross sectional configuration throughout the extent of the groove.

Although only the groove 258 is illustrated in FIG. 14, it should be understood that the groove 260 has the same cross sectional configuration as the groove 258. The two grooves 258 and 260 extend between the opposite end surfaces 252 and 254 of the conical body 242. It is contemplated that the grooves 258 and 260 could have a different cross sectional configuration if desired. For example, the grooves 258 and 260 could have the cross sectional configuration shown in FIG. 11 if desired.

Figure 15:
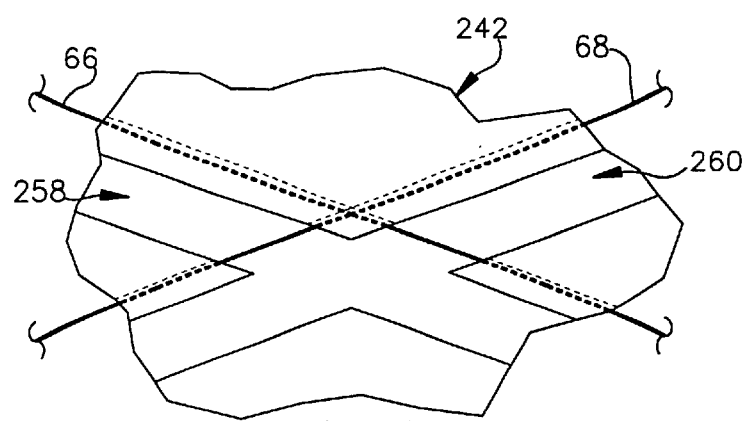
FIG. 15 is an enlarged fragmentary schematic illustration of a portion of FIG. 13, further illustrating the manner in which the suture is disposed in grooves formed in the suture retainer.
Figure 16:
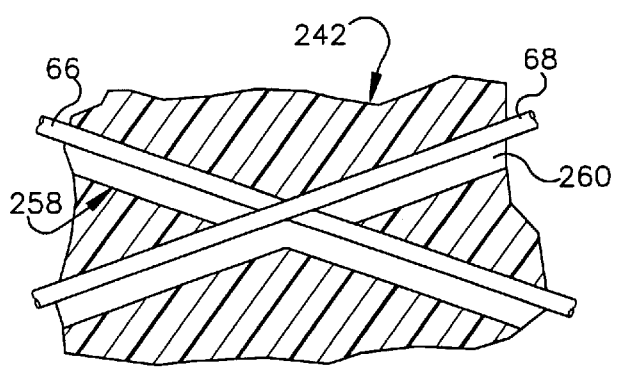
FIG. 16 is a fragmentary schematic sectional illustration of the manner in which the grooves and sections of the suture of FIG. 15 cross.

The grooves 258 and 260 intersect on opposite sides of the conical body 242 in the manner illustrated in FIGS. 15 and 16. At the intersections between the grooves 258 and 260, the left and right sections 66 and 68 of the suture 52 overlap (FIG. 16). The number of intersections of grooves 258 and 260 will vary as a direct function of the number of turns of the grooves 258 and 260 around the body 242.

Bridge sections 274 and 276 (FIG. 13) are provided across opposite ends of the groove 258 to facilitate in retaining the suture section 66 in the groove. Similarly, bridge sections 278 and 280 are provided across opposite ends of the groove 260 to facilitate in retaining the suture section 68 in the groove 260. If desired, the bridge sections 274, 276, 278 and 280 could be omitted.

Figure 13:
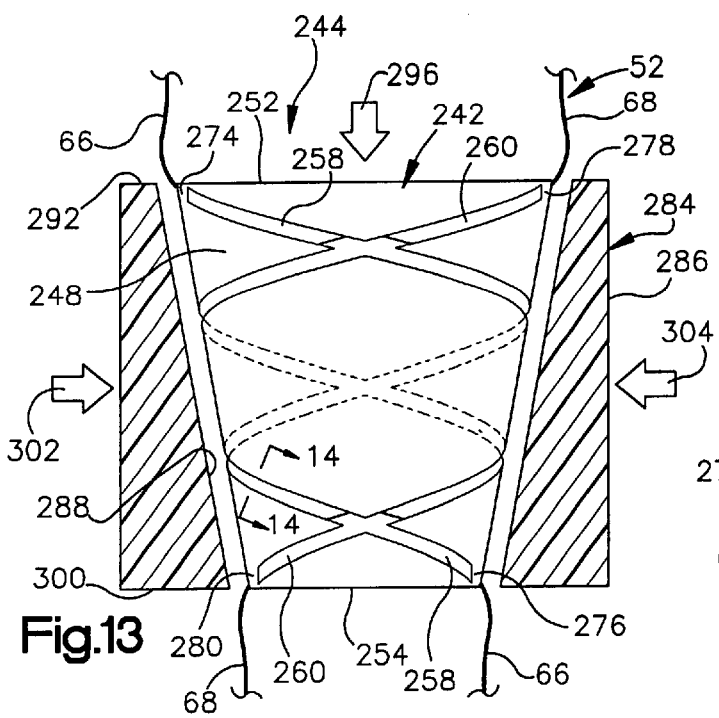
FIG. 13 is a schematic illustration depicting another embodiment of the suture retainer and the manner in which sections of a suture are wrapped in opposite directions to form bends in the suture.

In addition to the conical body 242, the suture retainer 244 includes a cylindrical sleeve 284 (FIG. 13). The tubular sleeve 284 has a cylindrical outer side surface 286 and a conical inner side surface 288. The inner and outer side surfaces 286 and 288 are disposed in coaxial relationship. The conical inner side surface 288 of the sleeve 284 tapers axially inward and downward (as viewed in FIG. 13) at the same angle as does the conical outer side surface 248 of the body 242.

Although the conical inner side surface 288 of the sleeve 284 has been schematically illustrated in FIG. 13 as having an inside diameter which is greater than the outside diameter of the conical body 242, it is contemplated that the conical body 242 will have substantially the same diameter as the inner side surface 288 of the sleeve 284. Therefore, when the circular end surface 252 on the conical body 242 is axially aligned with an annular end surface 292 on the sleeve 284 (as shown in FIG. 13), the outer side surface 248 on the conical body 242 will be disposed in abutting engagement with the inner side surface 288 on the sleeve 286. Of course, if the conical inner side surface 288 of the sleeve 284 has a larger diameter than the conical outer side surface 248 of the body 242, axially downward (as viewed in FIG. 13) movement of the conical body 242 relative to the sleeve 284 will result in abutting engagement between the inner side surface 288 of the sleeve and the outer side surface 248 of the conical body.

The conical body 242 and the sleeve 284 are both formed of a biodegradable polymer, such as polycaperlactone. However, the conical body 242 and the sleeve 284 could be formed of polyethylene oxide terephthalate or polybutylene terephthalate if desired. Other biodegradable or bioerodible copolymers could be utilized if desired. It is contemplated that it may be desired to form the conical body 242 and sleeve 284 of a polymer which is not biodegradable. The conical body 242 and sleeve 284 could be formed of two different materials if desired.

When the suture retainer 244 is to be positioned in a human patient's body, the left and right sections 66 and 68 of the suture are first inserted through the open center of the sleeve 284. The sections 66 and 68 of the suture 52 are then wrapped around the conical body 242 in the grooves 258 and 260. The sleeve 284 may then be moved along the suture 252 to the desired position in a patient's body.

It is believed that it will be preferred to position the left and right sections 66 and 68 of the suture 52 relative to the body tissue before winding the two sections of the suture around the body 242. However, one of the sections 66 or 68 of the suture 52 may be wound around the body 242 and inserted through the sleeve 284 before the suture is positioned relative to the body tissue. After the suture 52 has been positioned relative to the body tissue, the other section of the suture would be inserted through the sleeve 284 and wound around the body 242.

When the suture 52 has been positioned relative to the body tissue and suture retainer 244, the sections 66 and 68 of the suture 52 are tensioned as a force 296 (FIG. 13) is applied to the conical body 242. The force 296 is sufficient to cause the conical body 242 of the suture retainer 244 to slide axially along the sections 66 and 68 of the suture toward the sleeve 284. As this occurs, the outer side surface 248 on the conical body 242 moves into engagement with the inner side surface 288 on the sleeve 284. The force 296 is then effective to press the outer side surface 248 on the conical body 242 firmly against the inner side surface 288 of the sleeve.

The force 296 is also effective to press both the end surface 254 of the conical body 242 and an annular end surface 300 of the sleeve 284 against the body tissue. While the let and right sections 66 and 68 of the suture are tensioned, the force 296 is increased. After the suture retainer 244 has been pressed against the body tissue with a predetermined force 296 sufficient to cause the suture 52 to grip the body tissue with a desired tension, force applicator members, similar to the force applicator members 224, 226 and 228 of FIG. 12, compress the sleeve 284. The manner in which force is applied against the sleeve 284 is indicated schematically by arrows 302 and 304 in FIG. 13. If desired, one or more axial slot may be provided through a portion of the sleeve 284 to facilitate compression of the sleeve.

The force applied against the sleeve 284, indicated schematically at 302 and 304, causes radially inward plastic deformation of the sleeve. This force is transmitted through the sleeve to the conical body 242. The force transmitted to the conical body 242 causes a collapsing of the grooves 258 and 260. As the grooves 258 and 260 collapse, the material of the conical body 242 is plastically deformed and firmly grips or bonds to the outer side surfaces of the left and right sections 66 and 68 of the suture 52. The sleeve 284 bonds to the material of the conical body 242.

The sleeve 284 and conical body 242 of the suture retainer 244 are at a temperature below the transition temperature of the material forming the sleeve and conical body when they are compressed by the force indicated schematically at 302 and 304 in FIG. 13. This results in cold flowing of the material of both the sleeve 284 and the suture retainer 244 under the influence of the force 302 and 304. The force 302 and 304 is maintained at a predetermined magnitude for a time sufficient to result in cold plastic deformation of the material of the sleeve 284 and conical body 242. This plastic deformation or cold flow of the material of the sleeve 284 and conical body 242 occurs at a temperature which is substantially the same as the temperature of the body tissue with which the suture 52 is connected.

If desired, cold flowing of the material of the sleeve 284 and conical body 244 could be promoted by the addition of heat. Thus, the sleeve 284 and conical body 244 may be preheated before being moved into engagement with the body tissue. If desired, heat could be transmitted to the sleeve 284 and conical body 242 during application of he force 302 and 304. During the application of the force 302 and 304 to the sleeve 284, both the conical body 242 and sleeve 284 are at a temperature below the transition temperature of the material of the conical body and sleeve.

Once the suture retainer 284 has been plastically deformed to securely grip the suture 52, the suture may be knotted. Thus, a knot may be formed in the upper (as viewed in FIG. 13) end portions 66 and 68 of suture 52. The knot would pull the sections 66 and 68 of the suture firmly against the upper side surface 252 of the conical body 242. This knot would not decrease the overall force transmitting capability of the suture 52 since the suture retainer 244 would be disposed between the knot and the body tissue. Although such a knot would provide additional assurance that the suture will not work loose, it is believed that the knot is not necessary.

The tension in the suture 52 will press the annular end surface 300 on the sleeve 284 and the circular end surface 254 on the conical body 242 against the body tissue. Due to the relative large combined area of the end surfaces 254 and 300, the tension forces in the suture 52 will be applied to a relatively large area on the body tissue by the suture retainer 244. Since the suture retainer 244 applies force to a relatively large surface area on the body tissue and since the overall strength of the suture 52 is not impaired by the suture retainer 244, relatively large forces can be transmitted through the suture to the body tissue.

In the embodiment of the invention illustrated in FIGS. 13–16, the helical grooves 258 and 260 cross. This results in the left and right sections 66 and 68 of the suture 52 being disposed in overlapping engagement at the intersections between the grooves 258 and 260. The overlapping engagement of the left and right sections 66 and 68 of the suture 52 increases the resistance of the suture retainer 244 to slipping of one section of the suture relative to the other section of the suture.

Figures 17, 19:
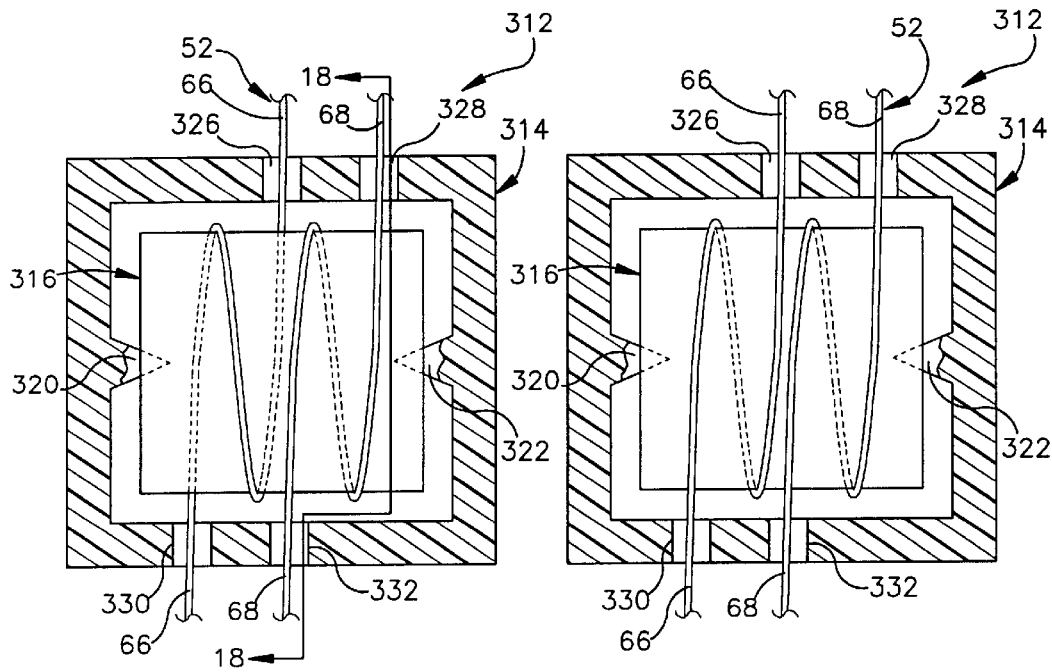
FIG. 17 is a schematic sectional view illustrating the manner in which a suture is wrapped around a roller in another embodiment of the suture retainer.
FIG. 19 is a fragmentary schematic illustration, generally similar to FIG. 17, depicting an alternative manner of wrapping the suture around the roller.
Figure 18:
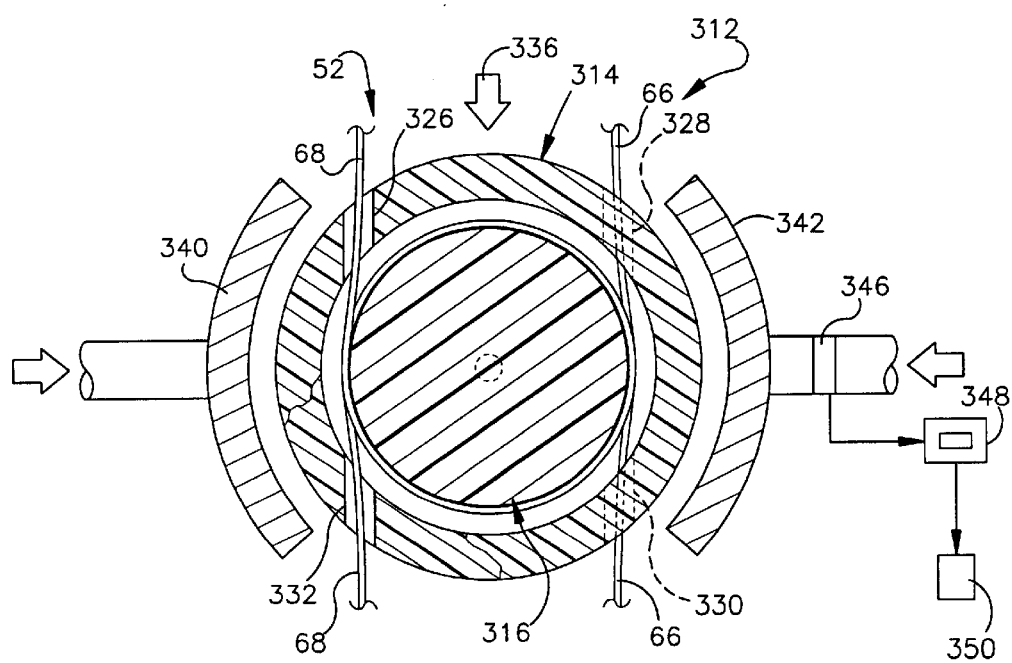
FIG. 18 is a schematic illustration depicting the manner in which the suture retainer of FIG. 17 is urged toward body tissue and the manner in which force is applied against the suture retainer to plastically deform the suture retainer.

Embodiments of FIGS. 17–19

In the embodiment of the invention illustrated in FIGS. 13–16, the central axis of the conical body 242 of the suture retainer 244 extends along the sections 66 and 68 of the suture 52. In the embodiments of the invention illustrated in FIGS. 17–19, a central axis of a circular body of the suture retainer extends transverse to the longitudinal axis of the suture during movement of the suture retainer toward the body tissue. Since the suture retainer of the embodiments of the invention illustrated in FIGS. 17–19 is similar to the suture retainer of the embodiment of the invention illustrated in FIGS. 13–16, similar terminology will be utilized to identify similar components. It should be understood that one or more features of the embodiments of the invention illustrated in FIGS. 1–16 may be used with the embodiments of the invention illustrated in FIGS. 17–19.

A suture retainer 312 (FIGS. 17 and 18) includes a cylindrical housing 314 and a rotatable cylinder 316. The housing 314 encloses the rotatable cylinder 316. The rotatable cylinder 316 has a central axis which is coincident with the central axis of the cylindrical housing 314.

The cylinder 316 is supported for rotation relative to the housing 314 by bearing sections 320 and 322 (FIG. 17). The bearing sections 320 and 322 are integrally formed as one piece with the housing 314. The bearing sections 320 and 322 have a conical configuration and engage conical recesses formed in opposite ends of the rotatable cylinder 316. The bearing sections 320 and 322 support the cylinder 316 in a coaxial relationship with the housing 314.

Left and right sections 66 and 68 of the suture 52 extend into the housing 314 through cylindrical openings 326 and 328. The sections 66 and 68 of the suture 52 extend from the housing 314 through openings 330 and 332. The openings 326, 328, 330 and 332 have parallel central axes which extend tangentially to the cylinder 316.

The left section 66 of the suture 52 extends through the opening 326 into the housing 314. The left section 66 of the suture 52 is wrapped in a clockwise direction (as viewed in FIG. 18) around the cylinder 316 and extends from the housing 314 through the opening 330. Similarly, the right section 68 (FIG. 17) of the suture 52 extends into the housing 314 through the opening 328. The right section 68 of the suture 52 is wrapped in a counterclockwise direction, as viewed in FIG. 18, around the cylinder 316. The turns in the left and right sections 66 and 68 in the suture 52 are axially spaced apart along the cylindrical outer side surface of the cylinder 316. If desired, helical grooves may be provided in the cylinder 316 to receive the turns of the left and right sections 66 and 68 of the suture.

The cylindrical housing 314 is formed of a biodegradable polymeric material. The cylinder 316 is also formed of a biodegradable polymeric material. However, the material of the cylinder 316 is harder than the material of the housing 314. The material of the cylinder 316 has a lower coefficient of friction than the material of the housing 314. The material of the housing 314 is easier to plastically deform than the material of the cylinder 316. Of course, the housing and cylinder 314 and 316 may be formed of the same material which may be biodegradable (polycaperlactone) or may not be biodegradable.

When the suture retainer 312 is to be positioned relative to body tissue (not shown), the left and right sections 66 and 68 of the suture are tensioned. The housing 312 is then pushed downward (as viewed in FIGS. 17 and 18) in the manner indicated schematically by an arrow 336 in FIG. 18. As this occurs, the turns or wraps of the sections 66 and 68 of the suture slide along a cylindrical outer side surface of the rotatable cylinder 316. The oppositely wound loops in the sections 66 and 68 of the suture 52 move downward along the suture toward the body tissue as the retainer 312 moves downward along the suture toward the body tissue.

Although there will be some rotational movement of the cylinder 316 relative to the housing 314, the position of the cylinder 316 relative to the housing 314 remains substantially constant during a major portion of the movement of the suture retainer 312 along the suture 52 toward the body tissue. This is because the left and right sections 66 and 68 of the suture are wrapped in opposite directions around the cylinder 316. This results in the portion of the loop in the left section 66 of the suture tending to rotate the cylinder 316 in a counterclockwise direction (as viewed in FIG. 18). At the same time, the loop formed in the right section 68 of the suture 52 tends to rotate the cylinder 316 in a clockwise direction (as viewed in FIG. 18).

Since the two sections 66 and 68 of the suture 52 tend to urge the cylinder 316 to rotate in opposite directions, the cylinder tends to remain more or less stationary relative to the housing 314. The loops in the left and right sections 66 and 68 of the suture 52 slide along the cylindrical outer side surface of the cylinder 316. However, it should be understood that there will be some rotational movement of the cylinder 316 relative to the housing 314 as the suture retainer 312 is moved toward the body tissue.

Once the housing 314 of the suture retainer 312 is moved into engagement with the body tissue, the tension is maintained in the sections 66 and 68 of the suture 52. The force 336 (FIG. 18) pressing the suture retainer 312 against the body tissue is increased. The suture retainer 312 is pressed against the body tissue with a force, indicated schematically by the arrow 336 in FIG. 18, which is sufficient to provide a desired tension in the portion of the suture 52 engaging the body tissue.

The material of the suture retainer 312 is then plastically deformed. The plastic deformation of the suture retainer 312 is accomplished by applying force against opposite sides of the housing 314 with a pair of force application members 340 and 342 (FIG. 18). The force applied against the suture retainer 312 by the force application members 340 and 342 presses the material of the housing 314 against the sections 66 and 68 of the suture and the cylinder 316 by cold flowing material of the housing.

A large gap has been shown between the cylindrical outer side surface of the cylinder 316 and a cylindrical inner side surface of the housing 314 in FIG. 18. However, it should be understood that this annular gap will be relatively small so that the material of the housing 314 can readily cold flow into engagement with the turns of the sections 66 and 68 of the suture 52 and cylinder 316. The force applied against the housing 314 also plastically deforms and causes cold flowing of the material of the cylinder 316 to provide a secure bond or grip between the material of the cylinder 316 and the suture 52.

A transducer or load cell 346 is associated with the force application member 342 and provides an output to a display unit 348. After a predetermined minimum force has been applied to the suture retainer 312 by the force application members 340 and 342 for a predetermined minimum length of time, an output from the display unit 348 to an indicator 350 activates the indicator to provide a signal that the desired plastic deformation of the suture retainer 312 has been obtained.

If desired, a knot may be tied between the left and right sections 66 and 68 of the suture 52 adjacent to a side of the housing 314 opposite from a side of the housing which is pressed against the body tissue by the suture. The knot would be pulled tight against the housing at a location between the openings 326 and 328. Since the suture retainer 312 is between the knot and the body tissue, the knot would not impair the force transmitting capability of the suture 52.

In FIGS. 17 and 18, the sections 66 and 68 of the suture 52 are wrapped in opposite directions around the cylinder 316. This results in offsetting forces being applied to the cylinder 316 by the turns in the sections 66 and 68 of the suture 52 during movement of the suture retainer 312 along the suture toward the body tissue. In FIG. 19, the left and right sections 66 and 68 of the suture 52 are wrapped in the same direction around the cylinder 316. This results in the turns or loops in the sections 66 and 68 of the suture 52 applying force to the cylinder 316 urging the cylinder to rotate in the same direction during movement of the suture retainer 312 along the sections 66 and 68 of the suture toward body tissue. Therefore, when the sections 66 and 68 of the suture 52 are wrapped in the same direction around the cylinder 316, the cylinder will freely rotate relative to the housing 314 as the suture retainer 312 is moved along the suture 52 toward the body tissue.

The overall force transmitting capability of the suture 52 is not impaired by the suture retainer 312. This is because the turns of the loops formed in the left and right sections of the suture 52 around the cylinder 316 do not form stress concentrations in the suture. If a knot had been used to interconnect the left and right sections 66 and 68 of the suture 52, in the manner taught by the prior art, the resulting stress concentration would reduce the overall force transmitting capability of the suture 52.

The cylindrical housing 314 increases the surface area on body tissue against which force is applied by tension in the suture 52 after the suture retainer 312 has been plastically deformed to grip the suture. This increases the amount of force which may be transmitted through the suture 52 without damaging the body tissue.

Figure 20:
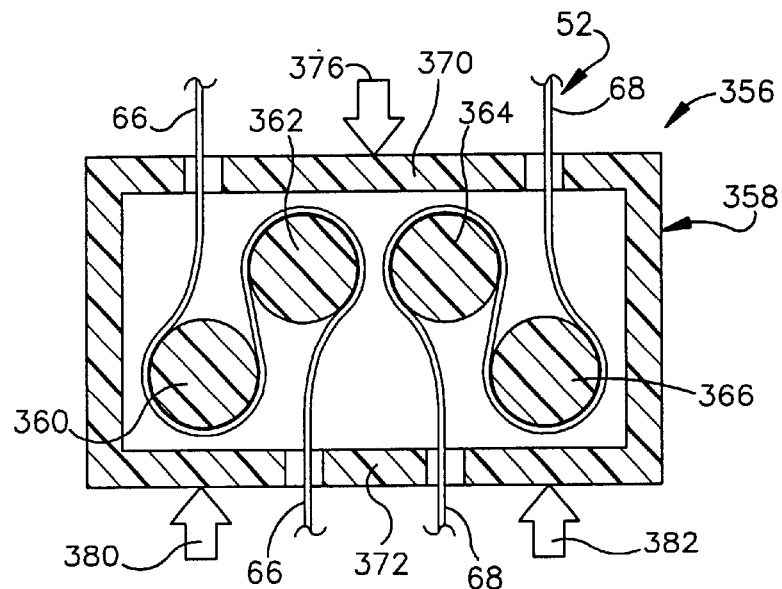
FIG. 20 is a fragmentary schematic illustration of another embodiment of the suture retainer in which a housing encloses a plurality of cylinders around which the suture is wrapped.

Embodiment of FIG. 20

In the embodiment of the invention illustrated in FIGS. 17–19, the cylinder 316 is rotatable relative to the housing 314. In the embodiment of the invention illustrated in FIG. 20, cylinders are fixedly connected with the housing. Since the embodiment of the invention illustrated in FIG. 20 is similar to the embodiment of the invention illustrated in FIGS. 17–19, similar terminology will be utilized to identify similar components. It should be understood that one or more features of the embodiments of the invention illustrated in, FIGS. 1–19 may be used with the embodiment of the invention illustrated in FIG. 20.

A suture retainer 356 includes a rectangular housing 358 which encloses a plurality of cylinders 360, 362, 364 and 366. The cylinders 360–366 have parallel central axes which extend parallel to flat rectangular upper and lower side walls 370 and 372 of the housing 358. Opposite end portions of the cylinders 360–366 are fixedly connected with rectangular end walls (not shown) of the housing 358. The central axes of the cylinders 360–366 extend perpendicular to the housing end walls to which the cylinders are fixedly connected.

In the embodiment of the invention illustrated in FIG. 20, the cylinders 360–366 are formed of a biodegradable material which is relatively hard. The housing 358 is formed of a biodegradable material which is relatively soft. By forming the housing 358 of a biodegradable material which is relatively soft, plastic deformation of the housing is facilitated. The relatively hard biodegradable material forming the cylinders 360–366 has a low coefficient of friction. Although it is preferred to form the cylinders 360–66 and housing 358 of biodegradable materials having different hardnesses, the cylinders and housing could be formed of biodegradable or nonbiodegradable materials having the same hardness if desired.

A suture 52 has left and right sections 66 and 68 which are wrapped around the cylinders 360–366 in a zig-zag fashion. Thus, the left section 66 of the suture 52 is looped around the cylinders 360 and 362. The right section 68 of the suture 52 is looped around the cylinders 364 and 366. The cylinders 360 and 362 maintain a pair of smooth, continuous bends in the left section 66 of the suture 52. Similarly, the cylinders 364 and 366 maintain a pair of smooth, continuous bends in the right section 68 of the suture 52. The smooth, continuous bends in the sections 66 and 68 of the suture 52 are free of stress inducing discontinuities. If desired., a greater or lesser number of bends could be maintained in the sections 66 and 68 of the suture 52 by a greater or lesser number of cylinders.

In the embodiment of the invention illustrated in FIG. 20, there is a single partial turn of the left section 66 of the suture around each of the cylinders 360 and 362. Similarly, there is a single partial turn of the right section 68 of the suture 52 around each of the cylinders 364 and 366. If desired, a plurality of turns or loops could be provided around each of the cylinders 360–366 by the sections 66 and 68 of the suture 52. For example, the left section 66 of the suture 52 could be wrapped for one complete revolution around the cylinder 360 and then wrapped for a partial revolution around the cylinder 360 before extending to the cylinder 362. Similarly, the right section 68 of the suture 52 could be wrapped for one complete revolution around the cylinder 366 and then wrapped for a partial revolution around the cylinder 364 before exiting from the housing 358.

After the suture 52 has been wrapped around the cylinders 360–366 in the manner illustrated schematically in FIG. 20, the suture retainer 356 is moved along the sections 66 and 68 of the suture 52 toward body tissue. As the housing 358 is moved downward (as viewed in FIG. 20), toward the body tissue, the left and right sections 66 and 68 of the suture 52 slide along the outer side surfaces of the cylinders 360–366. As this occurs, the cylinders 360–366 cooperate to maintain a plurality of bends in each of the sections 66 and 68 of the suture 52.

Once the housing 358 has been pressed against the body tissue with a predetermined force 376 while a predetermined tension is maintained in the left and right sections 66 and 68 of the suture 52, the housing 358 is plastically deformed to grip the suture 52. Thus, force, indicated by arrows 380 and 382 in FIG. 20 supplied against a side of the housing 358 opposite from the force 376. This force is effective to plastically deform the material of the housing and to press the material of the housing against the cylinders 360–366 and against the sections 66 and 68 of the suture 52.

As the forces indicated by the arrows 376, 380 and 382 plastically deform the housing 358, the material of the housing cold flows under the influence of the force. This cold flow of the material of the housing results in the left and right sections 66 and 68 of the suture being firmly pressed against the cylinders 360–366 to form a solid bond with the left and right sections 66 and 68 of the suture 52. Since the material forming the cylinders 360–366 is relatively hard, compared to the material forming the housing 358, the housing will deform to a greater extent than the cylinders during cold flow of the material of the housing. However, there will be some plastic deformation of the cylinders 360–366.

The force transmitting capability of the suture 52 is enhanced by minimizing stress concentrations in the suture and by transmitting force from the housing 358 to a large area on the body tissue. The bends formed in the suture 52 around the cylinders 360–366 are free of abrupt stress inducing discontinuities. The housing 358 transmits force to the body tissue located between the opposite sides of the left and right sections 66 and 68 of the suture 52. Therefore, stress concentrations in both the body tissue and the suture 52 tend to be minimized. If desired, a knot may be tied between the upper (as viewed in FIG. 20) end portions of the left and right sections 66 and 68 of the suture 52. Although such a knot would provide additional assurance that the suture 52 will not work loose, it is believed that the knot will not be necessary.

One of the ends of the suture could be fixedly connected with the housing 358. This could be done by forming the suture 52 as one piece with the housing 358 or by using a fastener. If one end of the suture is fixedly connected with the housing 358, one of the sets of cylinders, for example, the cylinders 360 and 362, could be eliminated.

Figure 21:
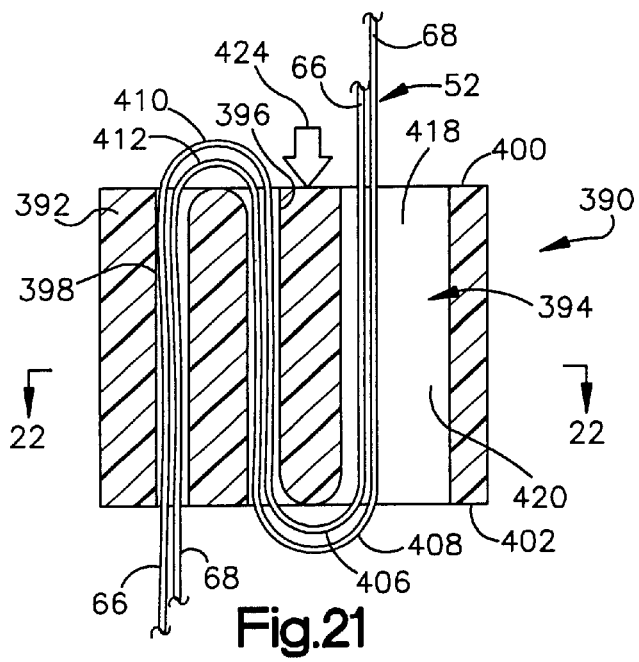
FIG. 21 is a schematic illustration depicting the manner in which the suture zigzags through passages in another embodiment of the suture retainer.
Figure 22:
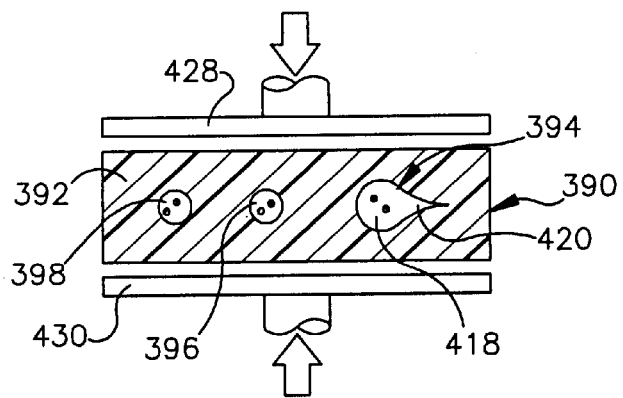
FIG. 22 is a schematic sectional view, taken generally along the line 22—22 of FIG. 21, further illustrating the manner in which the suture extends through the suture retainer.

Embodiment of FIGS. 21–22

In the embodiments of the invention illustrated in FIGS. 9–20, bends are formed in the left and right sections 66 and 68 of the suture 52 by circular surfaces. In the embodiment of the invention illustrated in FIGS. 21 and 22, the bends are formed in the suture by passages through a rectangular member. Since the embodiment of the invention illustrated in FIGS. 21 and 22 is similar to the embodiment of the invention illustrated in FIGS. 9–20, similar terminology will be utilized to identify similar components. It should be understood that one or more of the features of the embodiments of the invention illustrated in FIGS. 1–20 may be used with the embodiment of the invention illustrated in FIGS. 21–22.

A suture retainer 390 is formed in a single rectangular piece of biodegradable material. The suture retainer 390 includes a rectangular body 392 formed of a suitable biodegradable material. However, the rectangular body 392 could be formed of a non-biodegradable material if desired.

A plurality of parallel passages 394, 396 and 398 extend between opposite parallel rectangular end surfaces 400 and 402 of the body 392. The left and right sections 66 and 68 of the suture 52 zig-zag through the passages 394, 396 and 398 in a side-by-side relationship. The sections 66 and 68 of the suture 52 zig-zag through the passages 394, 396 and 398 to form a series of bends in the suture.

The passages 394, 396 and 398 in the body 392 of the suture retainer 390 cooperate to form smooth, continuous bends 406, 408, 410 and 412 (FIG. 21) in the sections 66 and 68 of the suture 52. Thus, the left and right sections 66 and 68 of the suture 52 extend through the straight passage 394. Bends 406 and 408 are formed in the portions of the sections 66 and 68 of the suture disposed between the passage 394 and the passage 396. Similarly, bends 410 and 412 are formed in the sections 66 and 68 of the suture 52 disposed between the passages 396 and 398. Of course, if there were additional passages formed in the rectangular body 392, additional bends would be formed in the suture 52.

The bends 406–412 in the sections 66 and 68 of the suture 52 are smooth and free of stress inducing discontinuities. By keeping the suture 52 free of stress inducing discontinuities, the force which can be transmitted through the suture tends to be maximized. If a knot was substituted for the suture retainer 390, stress concentrations would be formed and the force transmitting capability of the suture reduced.

The passage 394 has a main section 418 and a gripping section 420. The gripping section 420 has a tapered configuration (FIG. 22) and extends sideward from the main section 418. The left and right sections 66 and 68 of the suture 52 may be pulled from the main section 418 of the passage 394 into the gripping section 420 of the passage. As this occurs, the side surfaces of the passage 394 grip opposite sides of the left and right sections 66 and 68 of the suture 52 to hold the left and right sections of the suture against axial movement relative to the rectangular body 392 of the suture retainer 390.

The suture retainer 390 is formed of a single piece of biodegradable material, such as polycaperlactone. Of course, other suitable biodegradable or bioerodible materials could be utilized if desired. It is contemplated that the suture retainer 390 could be formed of materials which do not biodegrade.

After the suture 52 has been inserted into the suture retainer 390, in the manner illustrated schematically in FIG. 21, the suture retainer is moved along the suture toward body tissue (not shown). As the suture retainer 390 is moved along the suture 52, the side-by-side sections 66 and 68 of the suture slide in the same direction on surfaces of the suture retainer 390.

To effect movement of the suture retainer 390 along the suture 52, force is applied against the body 392, in the manner indicated schematically by an arrow 424 in FIG. 21. This causes the body 392 of the suture retainer 390 to slide along the sections 66 and 68 of the suture 52. At this time, the left and right sections 66 and 68 of the suture are tensioned. Therefore, the left and right sections of the suture slide along surfaces of the passages 394, 396 and 398 as the rectangular body 392 of the suture retainer 390 is moved toward the body tissue. As this occurs, the bends 406–412 move along the sections 66 and 68 of the suture 52 toward the body tissue.

When the leading end surface 402 on the rectangular body 392 of the suture retainer 390 engages the body tissue, the force indicated schematically by the arrow 424 is increased to a predetermined force. As this occurs, a predetermined tensioning force is applied to the left and right sections 66 and 68 of the suture 52. This results in the suture 52 being pulled tight to grip the body tissue with a desired force. The rectangular end surface 402 on the body 392 of the suture retainer 390 distributes the tension force in the suture 52 over a relatively large area on the body tissue.

While the retainer body 392 is being pressed against the body tissue with the predetermined force and the left and right sections 66 and 68 of the suture 52 are pulled taut with a predetermined tensioning force, the left and right sections 66 and 68 of the suture may be pulled towards the right (as viewed in FIGS. 21 and 22). As this occurs, the left and right sections 66 and 68 of the suture 52 will move from the main section 418 of the passage 394 into the gripping section 420 of the passage. This results in a frictional grip between the retainer body 392 and the suture 52 to hold the suture against movement relative to the retainer body and to maintain the desired tension in the suture.

While the body 392 of the suture retainer 390 is being pressed against the body tissue with the predetermined force 424 and while the predetermined tension is maintained in the left and right sections 66 and 68 of the suture 52, the material of the suture retainer 390 is plastically deformed. To plastically deform the material of the suture retainer 390, force applying members 428 and 430 (FIG. 22) apply a predetermined force against opposite sides of the body 392 of the suture retainer. This force causes cold flowing of the material of the body 392 of the suture retainer.

As the plastic deformation of the body 392 of the suture retainer 390 occurs, the passages 394, 396 and 398 are collapsed and the material of the body 392 of the suture retainer 390 cold flows around and grips the left and right sections 66 and 68 of the suture 52. The plastic deformation of the body 392 of the suture retainer 390 occurs at a temperature below the transition temperature of the material forming the suture retainer. If desired, the suture retainer 390 could be heated to promote cold flow of the material of the suture retainer.

In the embodiment of the invention illustrated in FIGS. 21 and 22, the gripping section 420 mechanically grips a portion of the suture 52. If desired, the gripping section 420 could be eliminated and the suture moved into engagement with a projection from the body 392. The upper (as viewed in FIG. 21) portions of the suture 52 could be wrapped around a projection from the body 392. Alternatively, the upper (as viewed in FIG. 21) portions of the suture could be moved into engagement with one or more hook-shaped locking notches on the body 392 of the suture retainer 390. Embodiments of FIGS. 23–25

Figure 23:
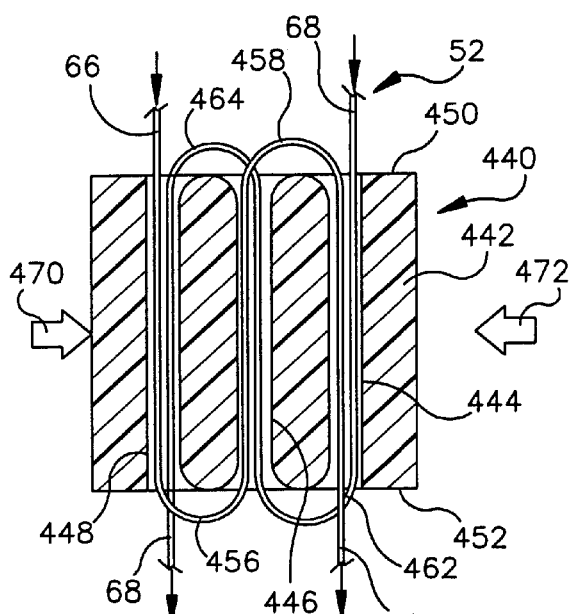
FIG. 23 is a schematic sectional view depicting the manner in which the suture zigzags through passages in another embodiment of the suture retainer.
Figure 24:
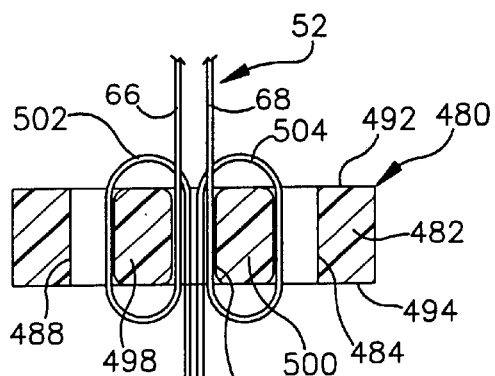
FIG. 24 is a schematic sectional view illustrating the manner in which turns of a suture are wrapped in looped around another embodiment of the suture retainer.
Figure 25:
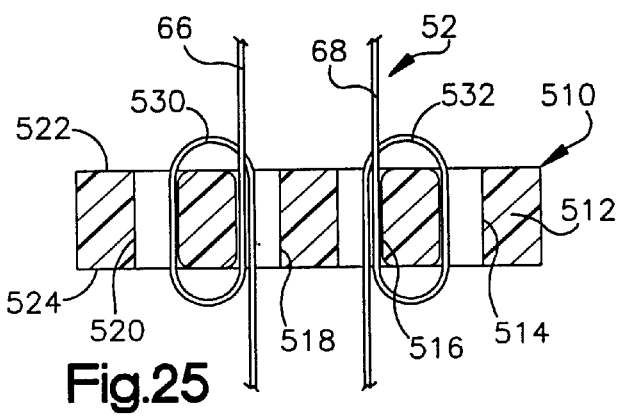
FIG. 25 is a schematic sectional view illustrating the manner in which turns of a suture are wrapped in looped around another embodiment of the suture retainer.

In the embodiment of the invention illustrated in FIGS. 21 and 22, the left and right sections 66 and 68 of the suture 52 extend through the passages 394, 396 and 398 in a side-by-side relationship. In the embodiments of the invention illustrated in FIGS. 23–25, loops are formed in the left and right sections of the suture around portions of the suture retainer. Since the embodiments of the invention illustrated in FIGS. 23–25 is similar to the embodiment of the invention illustrated in FIGS. 21–22, similar terminology will be utilized to identify similar components. It should be understood that one or more features of the embodiments of the invention illustrated in FIGS. 1–22 could be used with the embodiments of the invention illustrated in FIGS. 23–25.

A suture retainer 440 (FIG. 23) has a rectangular body 442. A plurality of straight parallel cylindrical passages 444, 446 and 448 extend between flat parallel rectangular end surfaces 450 and 452 of the rectangular body 442 of the suture retainer 440. The left and right sections 66 and 68 of the suture 52 extend through the passages 444, 446 and 448 in a zig-zag manner.

The left section 66 of the suture 52 zigzags through the passages 444, 446 and 448 in the rectangular body 442 of the suture retainer 440. When the left section 66 of the suture 52 is inserted into the suture retainer 440, the left section 66 of the suture is first moved downward (as viewed in FIG. 23) through passage 448. A smooth, continuous first bend 456 is then formed in the left section 66 of the suture 52 and the left section is moved upward through the passage 446. A smooth, continuous second bend 458 is then formed in the left section 66 of the suture 52. The left section 66 of the suture 52 is then moved downward through the passage 444.

The right section 68 of the suture 52 is also inserted into the suture retainer 440 in a zig-zag fashion. Thus, the right section 68 of the suture 52 is moved downward through the passage 444. A smooth, continuous first bend 462 is formed in the right section 68 of the suture 52. The right section 68 of the suture 52 is then moved upward through the passage 446. A smooth, continuous second bend 464 is then formed in the right section 68 of the suture 52. The right section 68 of the suture 52 is then moved downward through the passage 448.

In the embodiment of the invention illustrated in FIG. 23, the left and right sections 66 and 68 of the suture 52 are not aligned or in a side-by-side relationship with each other. Thus, the bends 456 and 458 in the left section 66 of the suture 52 are offset from the bends 462 and 464 in the right section 68 of the suture 52. The bends 456, 458, 462, and 464 are free of stress inducing discontinuities which would tend to weaken the suture 52.

After the suture 52 has been inserted into the suture retainer 440, in the manner illustrated schematically in FIG. 23, the left and right sections 66 and 68 of the suture are tensioned and force is applied to the rectangular body 442 of the suture retainer 440 to move the suture retainer along the suture 52 toward the body tissue. As this occurs, the left and right sections 66 and 68 of the suture 52 slide in opposite directions along the surfaces of the passages 444, 446 and 448. As this occurs, the zig-zag portion of the suture 52 is moved along the suture toward the body tissue.

When the rectangular leading end surface 452 of the body 442 of the suture retainer 440 moves into engagement with the body tissue, the suture retainer is pressed against the body tissue with a predetermined force while maintaining a predetermined tension in the left and right sections 66 and 68 of the suture. The suture retainer 440 is then plastically deformed to grip the left and right sections 66 and 68 of the suture 52. To plastically deform the material of the suture retainer 440, force is applied against opposite sides of the suture retainer 440, in the manner indicated by arrows 470 and 472 in FIG. 23.

The force indicated by the arrows 470 and 472 causes cold flow of the material of the suture retainer 440. The suture retainer 440 is formed from a single piece of biodegradable polymeric material, such as polycaperlactone. The plastic deformation of the suture retainer 440 occurs while the material of the suture is a temperature which is below the transition temperature of the material and is at a temperature close to the temperature of the body tissue. If desired, the suture retainer 440 could be heated to a temperature above the temperature of the body tissue and below the transition temperature of the material of the suture retainer to promote cold flow of the material of the suture retainer.

In the embodiment of the invention illustrated in FIG. 24, the sections of the suture 52 are wrapped around portions of the suture retainer in smooth, continuous loops. Thus, in the embodiment of the invention illustrated in FIG. 24, a suture retainer 480 includes a rectangular body 482 formed of a biodegradable polymeric material. A plurality of straight cylindrical passages 484, 486 and 488 extend between and are perpendicular to flat parallel end surfaces 492 and 494 on the rectangular body 482 of the suture retainer 480.

The suture 52 includes left and right sections 66 and 68. The left and right sections 66 and 68 are wrapped, in zig-zag fashion, around portions 498 and 500 of the rectangular body 482. This results in the formation of left and right loops 502 and 504 in the left and right sections 66 and 68 of the suture 52. The loops 502 and 504 are free of stress inducing discontinuities.

When the suture retainer 480 is to be positioned relative to the body tissue of a human patient, the left and right sections 66 and 68 of the suture 52 are tensioned with a predetermined force. Force is then applied to the rectangular body 482 of the suture retainer to move the suture retainer downward (as viewed in FIG. 24) along the suture 52. As this occurs, the left and right sections 66 and 68 slide along surfaces of the passages 484, 486 and 488. In addition, the loops 502 and 504 move downward (as viewed in FIG. 4) along the suture 52.

The leading end surface 494 of the rectangular body 482 is pressed against the body tissue with a predetermined force while a predetermined tension is maintained in the left and right sections 66 and 68 of the suture 52. The material of the suture retainer 480 is then plastically deformed to grip the left and right sections 66 and 68 of the suture 52. When the material of the suture retainer 480 is plastically deformed, the material of the suture retainer is below its transition temperature and is at a temperature close to the temperature of the body tissue. Therefore, the material of the suture retainer 480 cold flows under the influence of force applied against the suture retainer to collapse the passages 484, 486 and 488 and grip the left and right sections 66 and 68 of the suture 52.

The flat rectangular end surfaces of the suture retainer 480 applies force over a relatively large surface area on the body tissue. This reduces any tendency for the suture 52 to cut or separate the body tissue. The force which can be transmitted through the suture 52 is maximized by eliminating sharp bends in the suture. If the suture retainer 480 was eliminated and the suture was secured with a knot, the suture would be weakened by stress concentrations formed at sharp bends in the knot.

In the embodiment of the invention illustrated in FIG. 25, a suture retainer 510 includes a rectangular body 512 formed of a biodegradable polymeric material. A plurality of straight parallel cylindrical passages 514, 516, 518, and 520 extend between flat rectangular end surfaces 522 and 524 of the body 512.

The suture 52 includes left and right sections 66 and 68. Separate left and right loops 530 and 532 (FIG. 25) are formed in the sections 66 and 68 of the suture 52. Thus, the left loop 530 in the left section 66 of the suture 52 extends through the passages 518 and 520 in the rectangular body 512 of the suture retainer 510. Similarly, the right loop 532 extends through the passages 514 and 516 in the rectangular body 512 of the suture retainer 510.

When the suture retainer 510 is to be positioned relative to body tissue, the left and right sections 66 and 68 of the suture 52 are tensioned. Force is then applied to the suture retainer 510 to move the suture retainer downward (as viewed in FIG. 25) along the suture 52 into engagement with the body tissue. After the lower end surface 524 of the rectangular body 512 of the suture retainer 510 has been pressed against the body tissue with a predetermined force, the biodegradable polymeric material of the suture retainer 510 is plastically deformed by applying force against the suture retainer and cold flowing the material of the suture retainer. Cold flow of the material of the body 512 collapses the passages 514–520. The material of the body 512 then firmly grips the suture 52.

After plastic deformation of the material of the body 512, the suture retainer 510 at a temperature below the transition temperature of the material, a knot may be tied between the upper portions of the suture. This knot would be pressed tightly against the upper end surface 522 of the rectangular body 512 of the suture retainer 510. This know would be disposed at a location between the locations of the passages 516 and 518 before plastic deformation of the body 512 of the suture retainer 510. It is believed that such a knot may not be necessary.

In the embodiment of the invention illustrated in FIGS. 24 and 25, the passages through the rectangular bodies of the suture retainer are shorter than the passages through the rectangular body of the suture retainer illustrated in FIG. 23. However, it should be understood that the passages through the rectangular bodies of the suture retainers illustrated in FIGS. 24 and 25 could have a longer length if desired.

In the embodiments of the invention illustrated in FIGS. 23–25, the suture 52 is separate from the suture retainers 440, 480 and 510. However, one end of the suture 52 could be connected with any one of he suture retainers 440, 480 and 510. If this was done only one of the sections 66 or 68 would be zigzagged through passages in a suture retainer. For example, an end of the left section 66 of the suture 52 may be fixedly connected with one of the suture retainers 440, 480 or 510. Only the right section 68 of the suture 52 would have to be inserted through the passages in the one suture retainer 440, 480 or 510. The end of the suture 52 could be fixedly connected with a suture retainer 440, 480 or 5110 by a suitable fastener or by forming the suture as one piece with the suture retainer.

Figure 26:
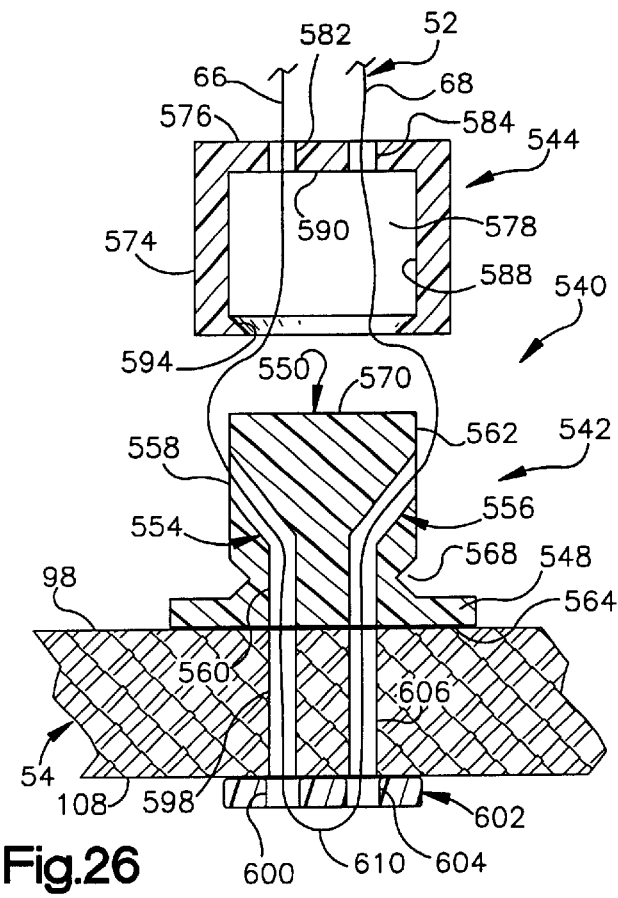
FIG. 26 is a schematic sectional view illustrating the manner in which a two-section embodiment of the suture retainer is positioned relative to body tissue prior to engagement of the two sections of the suture retainer.
Figure 27:
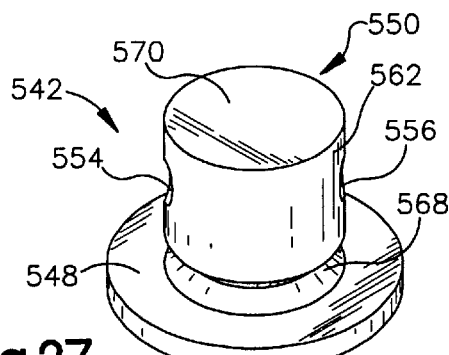
FIG. 27 is a pictorial illustration of an inner or lower section of the suture retainer of FIG. 26.
Figure 28:
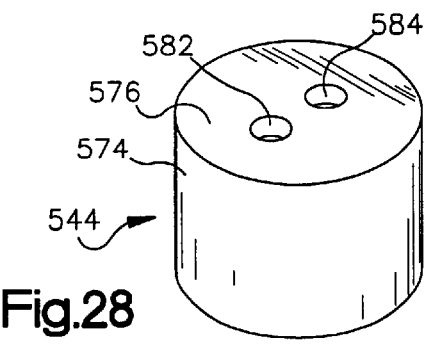
FIG. 28 is a pictorial illustration of an outer or upper section of the suture retainer of FIG. 26.

Embodiment of the Invention Illustrated in FIGS. 26, 27 and 28

In the embodiment of the invention illustrated in FIGS. 21–25, the suture retainer is formed form a single piece of biodegradable polymeric material. In the embodiment of the invention illustrated in FIGS. 26–28, the suture retainer is formed from a plurality of pieces of biodegradable polymeric material. Since the embodiment of the invention illustrated in FIGS. 26–28 is similar to the embodiment of the invention illustrated in FIGS. 21–25, similar terminology will be utilized to identify similar components. It should be understood that one or more of the features of the embodiments of the invention illustrated in FIGS. 1–25 could be used with the embodiment of the invention illustrated in FIGS. 26–28.

A suture retainer 540 (FIG. 26) includes a base 542 (FIGS. 26 and 27) and a sleeve or cap 544 (FIGS. 26 and 28). The base 542 has a circular flange 548 which extends radially outward from an upstanding central or post portion 550

(FIGS. 26 and 27). The post portion 550 has a generally cylindrical configuration and is disposed in a coaxial relationship with the circular flange 548. The flange 548 and post portion 550 are integrally formed from one piece of a biodegradable material, such as polycaperlactone. However, the base 542 and/or the cap 544 could be formed of a material which is not biodegradable.

A pair of passages 554 and 556 are provided in the post portion 550. The passage 554 includes a radially inward and downward sloping entrance portion 558 and a main portion 560. The main portion 560 extends parallel to the longitudinal central axis of the post portion 550. The entrance portion 558 of the passage 554 extends inwardly from a cylindrical outer side surface 562 of the post portion 550. The main portion 560 of the passage 554 extends perpendicular to a flat circular bottom side surface 564 of the flange 548.

The passage 556 has the same configuration as the passage 554. The passage 556 is disposed diametrically opposite to the passage 554. The passages 554 and 556 have a nonlinear configuration and form bends in he left and right sections 66 and 68 of the suture 52. The passages 554 and 556 are circumscribed by an annular recess 568 which extends around the lower end of the post portion 550 adjacent to the flange 548.

The upper end of the post portion 550 has a flat circular side surface 570 (FIG. 27). The flat side surface 570 on the post portion 550 extends parallel to and is coaxial with the flat bottom side surface 564 (FIG. 26) on the flange 548. The annular recess 568 is coaxial with the flange 548. The base portion 542 is formed of a biodegradable material, such as polycaperlactone. Other polymers which are biodegradable or bioerodible may be used. It is also contemplated that the base portion 542 could be formed of a polymer which does not biodegrade, such as an acetyl resin.

In addition to the base portion 542, the suture retainer 540 includes the one piece, cylindrical cap or sleeve 544 (FIG. 28). The cap 544 has a cylindrical outer side surface 574. A circular end surface 576 extends radially inwardly from the side surface 547. The cap 544 has a cylindrical cavity 578 (FIG. 26) which is disposed in a coaxial relationship with the cylindrical outer side surface 574 and end surface 576.

A pair of cylindrical passages 582 and 584 extend between the cavity 578 and the circular end surface 576 of the cap 544 (FIG. 26). The cavity 578 has a cylindrical side surface 588 which is disposed in a coaxial relationship with the outer side surface 574 on the cap 544. In addition, the cavity 578 has a circular end surface 590 which extends parallel to and is coaxial with the outer end surface 576 on the cap 544 (FIG. 26). An annular rib 594 (FIG. 26) projects radially inward from the cylindrical inner side surface 588 of the cavity 578. The cap 544 is integrally formed as one piece of a suitable biodegradable polymeric material, such as polycaperlactone. However, the cap 544 may be formed of a material which is not biodegradable.

When the suture 52 is to be connected with body tissue 54 (FIG. 26), one of the sections of the suture, for example, the right section 68, is threaded through the passage 582 into the cavity 578 in the cap 544. At this time, the suture 52 extends away from the cap 544 so that the left section 66 of the suture is disposed at a remote location. The right section 68 of the suture is then threaded through the passage 554 in the base portion 542. The right section 68 of the suture 52 is then threaded through a passage 598 in the body tissue 54.

In addition, the right section 68 of the suture 52 is threaded through a passage 600 in a force distribution member or button 602 which engages a lower side of the body tissue 54. The suture 52 is then threaded through a second passage 604 in the button 602 and a passage 606 in the body tissue 54. The button 602 distributes tension forces in the suture 52 over a relatively large area on the lower (as viewed in FIG. 26) side 108 of the body tissue. However, the button 602 could be omitted if desired.

The right section 68 of the suture is then threaded upward (as viewed in FIG. 26) through the passage 556 in the base portion 542 and into the cavity 578 in the cap 544. The right section 68 of the suture 52 is threaded out of the cavity 568 through the passage 584. As this occurs, the left section 66 of the suture 52 is pulled into the cap 544 and base portion 542.

Once the suture 52 has been threaded through the base portion 542 and cap 544 in the manner previously explained, the sections 66 and 68 of the suture are tensioned and the base portion 542 is slid along the suture 52. As this occurs, the bends formed in the left and right sections 66 and 68 of the suture 52 by the passages 554 and 556 in the base portion 542 are moved along the suture toward the body tissue 54. The bottom side surface 564 of the base portion 542 is then pressed against an upper side surface 98 of the body tissue 54 in the manner illustrated in FIG. 26.

The flat circular bottom side surface 564 of the flange 548 transmits force from the suture 52 to a relatively large area on the surface 98 of the body tissue 54. At this time, the tension in a connector portion 610 of the suture 52 will pull the force distribution member or button 602 firmly upward against a lower side surface 108 of the body tissue 54. This results in the body tissue 54 being clamped between the relatively large bottom surface area on the flange 548 and the button 602.

While the tension is maintained in the left and right sections 66 and 68 of the suture 52, the cap 544 is slid downward along the suture 52 into engagement with the base portion 542. Further downward movement of the sleeve or cap 544 resiliently deflects the rib 594 radially outward. Continued downward movement (as viewed in FIG. 26) of the sleeve or cap 544 moves the rib 594 along the outer side surface 562 of the post portion 542 into alignment with the recess 568. As this occurs, the rib 594 snaps into the recess 568.

Once the rib 594 is snapped into the recess 568, the left and right sections of the suture 52 are firmly gripped between the cylindrical inner side surface 588 of the cavity 578 in the cap 544 and the cylindrical outer side surface 562 of the post portion 550. In addition, the left and right sections 66 and 68 of the suture 52 are gripped between the circular end surface 590 of the cavity 578 and the circular end surface 570 of the post portion 550. The cap 544 and post portion 550 cooperate to form bends in the left and right sections 66 and 68 of the suture.

Under certain circumstances, it is believed that the mechanical gripping action provided between the cap 544 and base portion 542 of the suture retainer 540 may be sufficient to hold the suture 52 against movement relative to the body tissue. However, it is believed that it will be preferred to enhance the grip of the suture retainer 540 on the suture 52 by plastically deforming the material of the suture retainer. The plastic deformation of the suture retainer 540 occurs with the suture retainer at a temperature which is below the transition temperature of the biodegradable polymeric material forming the base portion 542 and cap 544 of the suture retainer.

Plastic deformation of the base portion 542 and cap portion 544 of the suture retainer 540 is accomplished by applying force against the cylindrical outer side surface 574 of the cap 544 in the same manner as illustrated schematically in FIG. 12. The force applied against the cylindrical outer side surface 574 (FIG. 26) of the cap 544 causes the material of the cap to cold flow and press against the left and right sections 66 and 68 of the suture 52. As this occurs, the passages 554 and 556 in the base portion 542 collapse. Due to the bends provided in the left and right sections 66 and 68 of the suture 52 in passing through the passages 554 and 556, and around the outside of the post portion 550 of the base portion 542, there is an extremely secure gripping action of the suture 52 upon plastic deformation of material of the cap 544 and base portion 542.

The force applied against the outer side surface 574 of the cap 544 is sufficient to cause cold flow of the material of the cap 544 and post portion 550. Cold flow of the material of the cap 544 firmly clamps the sections 66 and 68 of the suture 52 between the cap and post portion 550. Cold flow of the material of the post portion 550 collapses the passages 554 and 556. This results in a cold bonding of the material of the post portion 550 with the suture 52. The suture 52 is then securely gripped by the post portion 554.

It is preferred to form the base portion 542 and the cap 544 of the suture retainer 540 of the same biodegradable polymeric material. However, the base portion 542 could be formed of a biodegradable material which is somewhat harder than the biodegradable material forming the cap 544. This would facilitate plastic deformation of the cap 544 under the influence of force applied against the outer side surface 574 of the cap. If desired, the base portion 542 and/or cap 544 could be formed of a material which does not biodegrade.

After the suture retainer 540 has been plastically deformed by cold flowing the material of the suture retainer, the suture 52 may be knotted. Thus, a knot may be tied to interconnect the left and right sections 66 and 68 of the suture 52 in a known manner. During the tying of this knot, the suture 52 is pulled taut against the end surfaces 576 on the cap 544. The knot will be disposed between the passages 582 and 584 in the cap 544. The knot will not reduce the overall force transmitting capability of the suture 52 since the suture retainer 540 will be disposed between the knot and the body tissue 54. Although such a knot may be provided to be certain that the suture 52 does not work loose under the influence of varying loads, it is believed that the suture retainer 540 will be very capable of holding the suture 52 without the additional protection provided by the knot.

Embodiment of FIG. 29

In the embodiment of the invention illustrated in FIGS. 13–16, the suture 52 is wrapped around a conical body 242 which is moved into a sleeve 284 of a suture retainer 244. In the embodiment of the invention illustrated in FIG. 29, the suture extends through passages formed in a conical body and a sleeve. Since the embodiment of the invention illustrated in FIG. 29 is similar to the embodiment of the invention illustrated in FIGS. 13–16, similar terminology will be utilized to identify similar components. It should be understood that one or more of the features of the embodiments of the invention illustrated in FIGS. 1–28 could be used with the embodiment of the invention illustrated in FIG. 29.

A suture retainer 622 includes a conical body 624 and a cylindrical sleeve or base 626. The conical body 624 has an outer side surface 628 which is formed as a portion of a right circular cone. The outer side surface 628 of the conical body 624 extends between flat parallel circular end surfaces 630 and 632. The end surfaces 630 and 632 are disposed in a coaxial relationship with each other and with the outer side surface 628 of the conical body 624. The end surface 632 of the conical body 624 has a diameter which is smaller than the diameter of the end surface 630 of the conical body.

A pair of cylindrical passages 636 and 638 are disposed in the conical body 624. The passages 636 and 638 have straight central axes which are skewed at an acute angle to the central axis of the conical body 624. If desired, the passages 636 and 638 could have nonlinear central axes to promote the forming of bends in the suture 52. For example, the passages 636 and 638 could have a helical configuration. The conical body 624 is formed from a single piece of a biodegradable polymeric material, such as polycaperlactone.

The cylindrical sleeve 626 has a cylindrical outer side surface 642. The side surface 642 extends between a flat annular end surface 644 and a circular end surface 646. The end surfaces 644 and 646 extend parallel to each other and are disposed in a coaxial relationship.

A recess 650 is formed in the cylindrical sleeve 626. The recess 650 is of the same size and configuration as the conical body 624. The recess 650 has a side wall 652 which is formed as a portion of a cone. In addition, the recess 650 has a circular end surface 654 which extends parallel to the outer end surface 646 on the sleeve 626. The side wall 652 of the recess 650 has the same angle of taper as the outer side surface 628 of the conical body 624. However, if desired, the taper in the side wall 652 of the recess 650 could be slightly less than the taper in the outer side surface 628 of the conical body 624 to promote a wedging action between the conical body and the sleeve 626.

A pair of parallel cylindrical passages 660 and 662 extend between and are perpendicular to the end wall 654 of the recess 650 and the end surface 646 on the sleeve 626. The passages 660 and 662 have a linear configuration. However, the passages 660 and 662 could have a nonlinear configuration if desired.

When the suture retainer 622 is to be positioned relative to body tissue, the left section 66 of the suture 52 is inserted through the passage 660 in the sleeve 626. The left section 66 of the suture 52 is then inserted through the passage 636 in the conical body 624. Similarly, the right section 68 of the suture 52 is inserted through the passage 662 in the sleeve 626 and the passage 638 in the conical body 624.

The left and right sections 66 and 68 of the suture 52 are then tensioned and the sleeve 626 is moved along the suture 52 into engagement with the body tissue. When the end surface 646 of the sleeve has engaged the body tissue, the force applied against the sleeve and tension in the sections 66 and 68 of the suture 52 are increased. While a predetermined force is applied against the sleeve 626, the conical body 624 is moved along the left and right sections 66 and 68 of the suture 52 into the recess 650 in the sleeve. As this occurs, the left and right sections 66 and 68 of the suture are clamped between the outer side surface 628 of the conical body 624 and the conical side wall 652 of the recess 650.

To enhance the gripping action between the conical body 624 and the sleeve 626, force is applied against the cylindrical outer side surface 642 of the sleeve in the same manner as indicated schematically in FIG. 12. This force causes plastic deformation of the material of the sleeve 626 to firmly grip the conical body 624 and the left and right sections 66 and 68 of the suture 52. The force applied against the outer side surface 642 of the sleeve 626 causes a cold flowing of the material of the sleeve 626. The cold flowing of the material of the sleeve 626 will collapse the passages 660 and 662 to firmly grip the portion of the left and right sections 66 and 68 of the suture 52 extending through the passages.

In addition, the force applied against the sleeve 626 will be sufficient to cause plastic deformation, that is, cold flowing, of the material of the conical body 624 to collapse the passages 636 and 638. This results in the portions of the left and right sections 66 and 68 of the suture 52 disposed in the passages 636 and 638 being firmly gripped by material of the conical body 624.

It is contemplated that one end of the suture 52 could be fixedly connected with the suture retainer 622. Thus, one end of the suture 52 could be fixedly connected with the conical body 624. Alternatively, one end of the suture 52 could be fixedly connected with the sleeve 626.

It is also contemplated that a knot could be tied between the left and right sections 66 and 68 of the suture 52 at a location above (as viewed in FIG. 92) the suture retainer. The knot would be tied adjacent to the end surface 650 on the conical body 624. The knot would be tied immediately after plastically deforming the material of the suture retainer. It should be understood that the suture retainer 622 should be more than adequate to hold the suture 52 and the knot may be omitted.

The use of the suture retainer 622, rather than forming a knot to interconnect the two sections 66 and 68 of the suture 52, increases the force transmitting capability of the suture 52. This is because the stress concentrations induced by the forming of a knot are avoided.

In addition, the use of the suture retainer 62, rather than forming a knot to interconnect the two sections 66 and 68 of the suture 52, reduces stress concentrations in the body tissue. The flat end surface 646 distributes tension forces in the suture 52 over a relatively large surface area on the body tissue. This minimizes stress concentrations in the body tissue and minimizes any tendency for the body tissue to be cut or separated by the force applied against the body tissue.

Embodiment of FIGS. 30 and 31

In the embodiment of the invention illustrated in FIG. 29, the left and right sections 66 and 68 of the suture 52 are inserted into passages formed in the conical body 624. In the embodiment of the invention illustrated in FIGS. 30 and 31, the conical body 34 has a hinge section which is pivotal to open the conical body and facilitate insertion of the left and right sections of the suture. Since the embodiment of the invention illustrated in FIGS. 30 and 31 is similar to the embodiment of the invention illustrated in FIG. 29, similar terminology will be utilized to identify similar components. It should be understood that one or more of the features of the embodiments of the invention illustrated in FIGS. 1–92 could be used with the embodiment of the invention illustrated in FIGS. 30 and 31.

A suture retainer 670 (FIG. 30) includes a conical body 672 and a sleeve 674. The conical body 672 is formed as two sections 676 and 678 (FIG. 31). The sections 676 and 678 of the conical body are pivotally interconnected at a hinge 680. The hinge 680 is integrally formed as one piece with the sections 676 and 678 of the conical body 672. The hinge 680 enables the left and right sections 66 and 68 (FIG. 30) of the suture 52 to be inserted through an opening 684. The opening 684 extends between axially opposite ends of the conical body 672.

The sleeve 674 includes a circular flange 688 which extends radially outward from a cylindrical outer side surface 690 of the sleeve 674. A conical recess 692 has a relatively large open end in an upper annular end surface 694 of the sleeve 674 and a relatively small open end in a flat annular end surface 696 disposed on the bottom of the flange 688. The left and right sections 66 and 68 of the suture are inserted through the open ended conical recess 692 in the sleeve 674. The left and right sections 66 and 68 of the suture 52 are then inserted through the opening 684 (FIG. 31) into the conical body 672.

While tension is maintained in the left and right sections 66 and 68 of the suture 52, the sleeve 674 is moved along the suture until the leading end surface 696 on the bottom of the flange 688 engages the body tissue. The sleeve 674 is then pressed against the body tissue with a predetermined force while a predetermined tension is maintained in the left and right sections 66 and 68 of the suture 52. The conical body 672 is then moved along the left and right sections 66 and 68 of the suture 52 into the open ended recess 692 in the sleeve 674.

Force is then applied against the outer side surface 690 of the sleeve 674 to plastically deform the sleeve. As this occurs, the material of the sleeve 674 cold flows radially inward and applies force against the conical body 672. This force is sufficient to cause cold flowing of the material of the conical body and gripping of the left and right sections 66 and 68 of the suture 52 with the material of the conical body 672.

The conical body 672 and sleeve 674 are formed of a biodegradable material. However, the conical body 672 and/or sleeve 674 could be formed of a different material if desired.

Figures 32, 33:
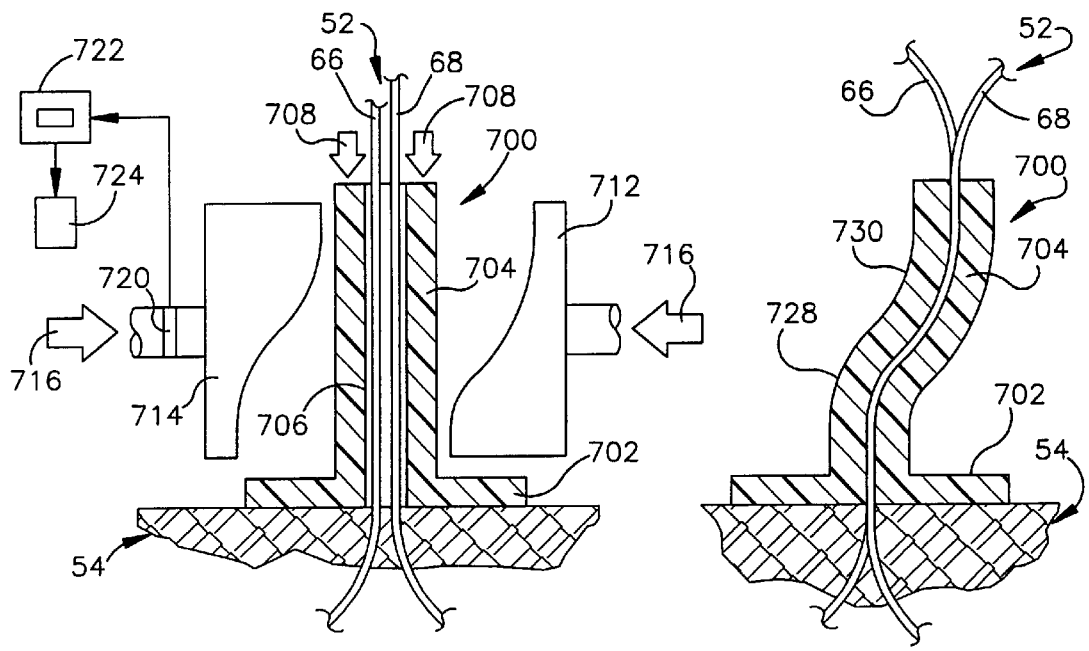
FIG. 32 is a schematic sectional illustration depicting the manner in which another embodiment of the suture retainer is pressed against a large area on body tissue with a predetermined force.
FIG. 33 is a schematic view of the suture retainer of FIG. 32 after the suture retainer has been plastically deformed to grip the suture.

Embodiment of FIGS. 32 and 33

In the embodiment of the invention illustrated in FIGS. 29, 30 and 31, two-piece suture retainers are utilized to grip the left and right sections of the suture 52. In the embodiment of the invention illustrated in FIGS. 32 and 33, a one-piece tubular suture retainer is utilized to grip the left and right sections of the suture. Since the embodiment of the invention illustrated in FIGS. 32 and 33 is similar to the embodiment of the invention illustrated in FIGS. 29–31, similar terminology will be utilized to identify similar components. It should be understood that one or more of the features of the embodiments of the invention illustrated in FIGS. 1–31 could be used with the embodiment of the invention illustrated in FIG. 32.

In the embodiment of the invention illustrated in FIG. 32, a suture retainer 700 is formed from a single piece of a biodegradable polymeric material, such as polycaperlactone. The suture retainer 700 includes an annular flange or base 702 and an upright tubular cylindrical main section 704. The tubular cylindrical main section 704 is disposed in a coaxial relationship with the base 702. A straight cylindrical passage 706 extends through the tubular main section 704 and base 702 of the suture retainer 700. If desired, the passage 706 could have a nonlinear configuration.

Left and right sections 66 and 68 of the suture 52 are inserted through the passage 706 in the suture retainer 700. While a predetermined tension is maintained in the left and right sections 66 and 68 of the suture 52, a predetermined force, indicated schematically by the arrows 708 in FIG. 32, is applied to the main section 704 of the suture retainer. The force 708 is distributed over a relatively large surface area on the body tissue 54 by the base 702.

The suture retainer 700 is then plastically deformed to grip the left and right sections 66 and 68 of the suture 52. To plastically deform the suture retainer 700, force application members 712 and 714 are pressed against opposite sides of the main section 704 of the suture retainer 700 with a predetermined force, indicated schematically by the arrows 716 in FIG. 32. When the force 716 is applied to the suture retainer 700, the suture retainer is at a temperature below the transition temperature of the material forming the suture retainer. Therefore, the force 716 is effective to cause cold flow of the material of the suture retainer 700.

The force applied against the suture retainer 700 by the force applying members 712 and 714 is measured by a transducer or load cell 720. The magnitude of the force 716 is transmitted from the load cell 720 to a display unit 722. When a predetermined minimum force 716 has been applied to the suture retainer 700 for a predetermined minimum period of time by the force applying members 712 and 714, the display unit 722 activates an indicator 724.

The force applying members 712 and 714 are configured to form a plurality of bends 728 and 730 in the tubular main section 704 of the suture retainer 700 (FIG. 33). Thus, the force applying members 712 and 714 deform the main section 704 of the suture retainer 700 from a straight cylindrical configuration (FIG. 32) to a nonlinear configuration (FIG. 33). The bends 728 and 730, in combination with the cold plastic deformation of the material of the suture retainer 700, result in the suture retainer 700 having a firm grip on the left and right sections 66 and 68 of the suture 52. It should be understood that the force application members 712 and 714 could be configured to form a greater number of bends in the main section 704 of the suture retainer.

In the illustrated embodiment of the suture retainer 700, a single passage 706 (FIG. 32) extends through the suture retainer. If desired, a plurality of passages could be provided in the suture retainer 700. If this was done, the left section 66 of the suture would be inserted through one of the passages and the right section 68 would be inserted through another passage.

The bends 728 and 730 (FIG. 33) in the suture retainer 700 form smooth, continuous bends in the suture 52. This avoids the formation of stress concentrations in the suture 52. If a knot had been utilized in place of the suture retainer 700 to interconnect the sections 66 and 68 of he suture 52, stress concentrations would have been formed in the suture and the overall force transmitting capability of the suture would have been impaired.

The annular base 702 projects radially outward from the cylindrical main section. Since the tension force transmitted to the suture retainer 700 by the suture 52 is transmitted to the body tissue 54 by the base 702, the suture tension force is transmitted to a relatively large surface area on the body tissue. This minimizes the possibility of the suture 52 and suture retainer 700 being pulled downward (as viewed in FIG. 33) into the body tissue 54 by the tension force in the suture. In addition, the large base 702 minimizes the possibility of damage to the body tissue 54.

If desired, a knot could be tied between the upper end portions of the sections 66 and 68 of the suture. This knot would be disposed above and would press against an upper (as viewed in FIG. 33) end of the suture retainer. Although stress concentrations would be formed in the suture 52 at the knot, the knot would not impair the force transmitting capability of the portion of the suture engaging the body tissue 54. This is because the suture retainer 700 would be disposed between the body tissue 54 and the knot.

Figure 34:
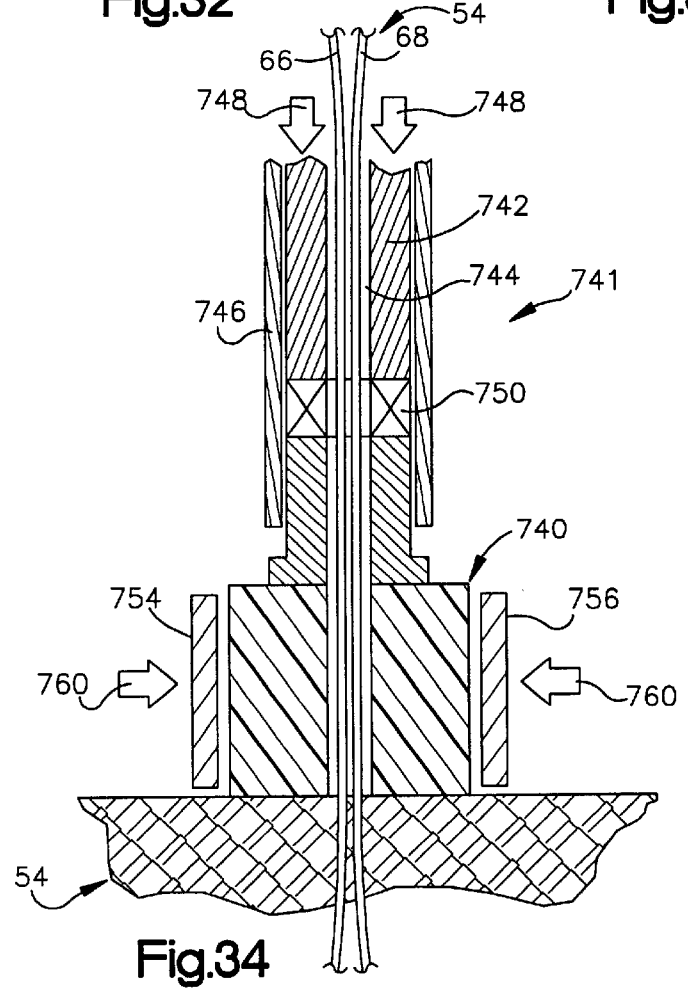
FIG. 34 is a schematic illustration depicting the manner in which another embodiment of the suture retainer is pressed against body tissue and the manner in which force is applied against the suture retainer to effect plastic deformation of the suture retainer.

Embodiment of FIG. 34

In the embodiment of the invention illustrated in FIG. 34, the suture retainer has a tubular configuration. Since the embodiment of the invention illustrated in FIG. 34 is similar to the embodiments of the invention illustrated in FIGS. 1–33, similar terminology will be utilized to identify similar components. It should be understood that one or more of the features of the embodiments of the invention illustrated in FIGS. 1–33 could be used with the embodiment of the invention illustrated in FIG. 34.

A suture 52 (FIG. 34) has left and right sections 66 and 68 which extend through a tubular cylindrical suture retainer 740 into body tissue 54. An apparatus 741 for pressing the suture retainer 740 against the body tissue 54 includes a tubular cylindrical plunger 742 having a cylindrical central passage 744 through which the left and right sections 66 and 68 of the suture 54 extends. The plunger 742 is enclosed in a tubular cylindrical housing 746.

The plunger 742 is pressed downward, relative to the housing 746 against the suture retainer 740 with a predetermined force, indicated by arrows 748 in FIG. 34. An annular transducer or load cell 750 provides an output indicative of the magnitude of the force 748 with which the suture retainer 740 is pressed against the body tissue 54 by the plunger 742.

While the left and right sections 66 and 68 of the suture 54 are being tensioned with a predetermined force and while the plunger 742 is being pressed against the suture retainer 740 with a predetermined force, the suture retainer 740 is plastically deformed. To plastically deform the suture retainer 740, a plurality of force applying or clamp members 754 and 756 are pressed against the suture retainer with a predetermined minimum force, indicated schematically by arrows 760 in FIG. 34. The force application members 754 and 756 may have an arcuate configuration to conform to the cylindrical configuration of the suture retainer 740 or may have a flat configuration. The force applied against the suture retainer 740 by the force 760 applying members 754 and 756 is sufficient to cause plastic deformation of the material of the suture retainer.

The force 760 is applied against the suture retainer while the suture retainer is at a temperature which is below the transition temperature of the biodegradable polymer which forms the suture retainer. Thus, the suture retainer is at approximately the same temperature as the body tissue 54 when the force 760 is applied against the suture retainer. The force 760 causes the material of the suture retainer to cold flow and grip the left and right sections 66 and 68 of the suture 54 in the manner previously explained.

Although the apparatus 741 has been illustrated in FIG. 34 in association with the suture retainer 740, it is contemplated that the apparatus 741 could be used with any one of the suture retainers of FIGS. 1–33. Although the force applying members 754 and 756 have an arcuate configuration to grip the arcuate outer side surface of the suture retainer 740. It is contemplated that the force applying members could have a different configuration to grip a suture retainer having a noncylindrical configuration.

Figure 35:
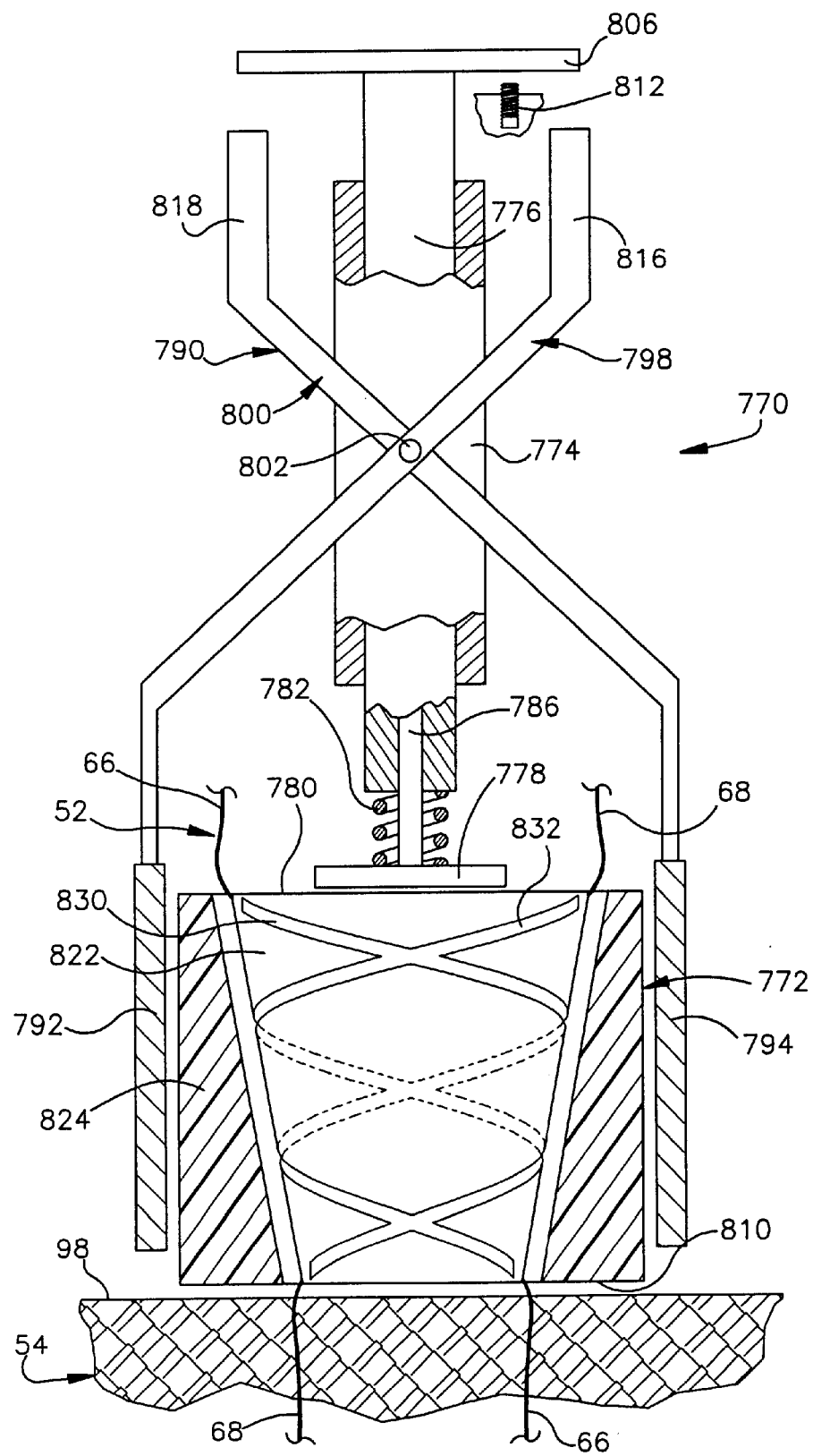
FIG. 35 is a schematic illustration of a tool which may be used to press the suture retainer of FIG. 13 against body tissue and to plastically deform the material of the suture retainer.

Embodiment of FIG. 35

In the embodiment of the invention illustrated in FIG. 35, an apparatus similar to the apparatus illustrated in FIG. 34 is utilized to install a suture retainer having the same construction as the suture retainer of FIGS. 13–16. Since the embodiment of the invention illustrated in FIG. 35 is similar to the embodiment of the invention illustrated in FIG. 34, similar terminology will be utilized to identify similar components.

An apparatus or tool 770 (FIG. 35) is utilized to position a suture retainer 772 relative to body tissue 54. The apparatus 770 includes a tubular housing or base 774 through which a cylindrical plunger 776 extends. A force application member 778 extends from the plunger 776 and is engageable with an upper or trailing end surface 780 of the suture retainer 772. A biasing spring 782 urges the force application member 778 to the extended position illustrated in FIG. 35.

Upon application of a predetermined force to the trailing end surface 780 of the suture retainer 772 by the force application member 778, an indicator connected with a shaft 786 indicates to an operator of the apparatus 770 that a desired force has been applied against the suture retainer 772. The indicator may be either a direct reading of the position of the shaft 786 relative to the plunger 776 or an output from a transducer, such as a load cell.

The apparatus 770 includes a gripper assembly 790 which is operable to grip and to deform the suture retainer 772. The gripper assembly 790 includes a left force application member 792 and a right force application member 794. The force application members 792 and 794 engage opposite sides of the suture retainer 772. The force application members 792 and 794 are configured to correspond to the shape of an outer side surface of the suture retainer 772.

An actuator member 798 is connected with the left force application member 792. A second actuator member 800 is connected with the right force application member 794. The actuator members 798 and 800 are pivotally mounted on the housing 774 at a pivot connection indicated schematically at 802 in FIG. 35.

Downward force is manually applied to an upper input end portion 806 of the plunger 776 while a predetermined tension is maintained in the left and right sections 66 and 68 of the suture 52. The downward (as viewed in FIG. 35) force applied against the plunger 776 is transmitted through the spring 782 to the force application member 778. The force application member 778 applies force to the trailing end surface 780 of the suture retainer 772 to press a leading end surface 810 on the suture retainer 772 against the side surface 98 of the body tissue 54.

An adjustable stop member 812 is connected with the housing 774. The stop member 812 is adjustable to limit the extent of downward movement of the input end portion 806 of the plunger 776 relative to the housing 774. This enables the stop member 812 to limit the amount of force transmitted through the spring 782 to the suture retainer 772 to a predetermined force.

Manual force is applied against upper (as viewed in FIG. 35) end portions 816 and 818 of the actuator members 798 and 800. During the application of the manual force to the upper end portions 816 and 818 of the actuator members 798 and 880, the predetermined tension is maintained in the left and right sections 66 and 68 of the suture 52. In addition, the predetermined downward force is transmitted from the plunger 776 through the spring 782 and force application member 778 to the suture retainer 772.

The manual force applied to the end portions 816 and 818 of the actuator members 798 and 800 is transmitted to the force application members 792 and 794. The force application members 792 and 794 are pressed against the suture retainer 792 with sufficient force too plastically deform the suture retainer by cold flowing the material of the suture retainer.

Although the suture retainer 772 may have any one of the constructions illustrated in FIGS. 1–34, the suture retainer 772 has the same construction as the suture retainer 244 of FIG. 13. Thus, the suture retainer 772 includes a conical body 822 and a cylindrical sleeve 824. The suture 52 has a left section 66 which is wrapped for a plurality of turns around the conical body 822 and is disposed in a helical groove 830 formed in the conical body 822. Similarly, a right section 68 of the suture 52 is wrapped for a plurality of turns around the conical body 822 and is disposed in a helical groove 832 formed in the conical body 822.

When the suture retainer 772 is to be positioned relative to the body tissue 54, the suture 52 is inserted through the sleeve 824. The left section 66 of the suture is then positioned in the helical groove 830 in the conical body 822 of the suture retainer 772. The right section 68 of the suture 52 is positioned in the helical groove 832 in the conical body 822 of the suture retainer 772.

The apparatus or tool 770 is then operated to hold the suture retainer 772 in the manner illustrated schematically in FIG. 35. Thus, the force application member 778 is positioned in abutting engagement with the trailing end surface 780 of the suture retainer 772. At the same time, the left and right force application members 792 and 794 grip the sleeve 824 of the suture retainer 772. This results in the conical body 822 of the suture retainer 772 being telescopically pressed into the sleeve 824 while the sleeve is held by the force application members 792 and 794.

While the predetermined tension is maintained in the left and right sections 66 and 68 of the suture 52, the tool 770 and the suture retainer 772 are moved along the suture 52 toward the body tissue 54. The tool 770 is moved along a path which extends parallel to the taut portions of the left and right sections 66 and 68 of the suture 52 which extend upward (as viewed in FIG. 35) from the suture retainer 772. As the suture retainer 772 is moved along the suture 52 toward the body tissue 54, the left and right sections 66 and 68 of the suture slide along the grooves 830 and 832. The grooves 830 and 832 are effective to maintain the helical turns or loops in the left and right sections 66 and 68 of the suture 52 as the suture retainer 772 moves along the suture 52 toward the body tissue 54.

The force required to slide the suture retainer 772 along the suture 52 is transmitted from the tool 700 to the suture retainer. Thus, force is transmitted from the force application member 778 to the trailing end surface 780 of the conical body 822. At the same time, a clamping force is transmitted from the force application members 792 and 794 to the sleeve 824. The sleeve 824 is securely held by the force application members 792 and 794 while the conical body 822 is pressed axially against the sleeve by the force application member 778. During movement of the suture retainer 772 along the suture 52, the force applied against the suture retainer by the tool 700 is ineffective to cause significant deformation of the suture retainer.

At this time, the tool 770 extends along the portions of the left and right sections 66 and 68 of the suture 52 extending upward (as viewed in FIG. 35) from the suture retainer 772. Since the tool 770 extends from the suture retainer 772 in the same direction as the left and right sections 66 and 68 of the suture 52, the tool can be used to position the suture retainer relative to body tissue 54 in very restricted space commonly present in operating environments.

When the leading end surface 810 on the suture retainer 772 engages the upper (as viewed in FIG. 35) side surface 98 of the body tissue 54 (FIG. 35), the force applied against the actuator members 798 and 800 is reduced. Manual force is then applied against the input end portion 806 of the plunger 776 to move the plunger downward and compress the spring 782. The stop member 812 is engaged by the input end portion 806 of the plunger 776 when a predetermined force is being transmitted through the spring 782 and force application member 778 to the suture retainer 772.

This results in the predetermined downward force being transmitted from the force application member 778 to the suture retainer 772 to press the conical body against the sleeve 824. The predetermined downward force is then transmitted from the sleeve 824 and conical body 822 to the body tissue 54. While the suture retainer 772 is being pressed against the body tissue with the predetermined downward force, a predetermined tension force is maintained in the left and right sections 66 and 68 of the suture 52.

In the schematic illustration of FIG. 35, there is space between the conical body 822 and the sleeve 824. In addition, there is space between the sleeve 824 and the force application members 792 and 794. It should be understood that the conical outer side surface of the body 822 is pressed firmly against the correspondingly shaped conical inner side surface of the sleeve 824. It should also be understood hat the force application members 792 and 794 are pressed against the cylindrical outer side surface of the sleeve 824. At this time, the left and right sections 66 and 68 of the suture are tensioned.

While the predetermined force is being applied against the trailing end surface 780 of the suture retainer 772 by the force application member 778, manual force is applied against the upper end portions 816 and 818 of the actuator members 798 and 800 to effect plastic deformation of the suture retainer 772. Thus, the left and right force applying members 792 and 794 are pressed against the cylindrical sleeve 824 with sufficient force to plastically deform both the cylindrical sleeve and the conical body 822 of the suture retainer 772. At this time, the suture retainer 772 is at approximately the same temperature as the body tissue 54 and is at a temperature which is below the transition temperature of the biodegradable polymeric material forming the suture retainer. Therefore, cold flowing the material of the suture retainer occurs under the influence of the force applied against the suture retainer 772 by the left and right force applying members 792 and 794.

The cold flowing of the material of the suture retainer 772 under the influence of the force applied to the suture retainer by the force application members 792 and 794 results in the suture 52 being firmly gripped in the manner set forth in association with the suture retainer 244 of the embodiment of FIGS. 13–16. The application of force to the actuator members 798 and 800 is then interrupted. The application of force to the input end portion 806 of the plunger 776 is also interrupted. The apparatus 770 is then moved upward (as viewed in FIG. 35) away from the suture retainer.

Although the apparatus 770 has been disclosed herein in association with the suture retainer 772, it is contemplated that the apparatus could be utilized to install suture retainers having a different construction. If the apparatus 770 is used to install a suture retainer having an outer side surface with a configuration which is different than the configuration of outer side surface of the suture retainer 772, the configuration of the force application members 792 and 794 would be modified to correspond to the configuration of the suture retainer to be installed. For example, if the suture retainer had a flat outer side surface, the force application members 792 and 794 would be modified to have flat surfaces to engage the suture retainer. If the suture retainer had the spherical outer side surface of the suture retainer 50 (FIG. 2), the force application members 792 and 794 would have configurations corresponding to the configuration of portions of a sphere.

Figure 36:
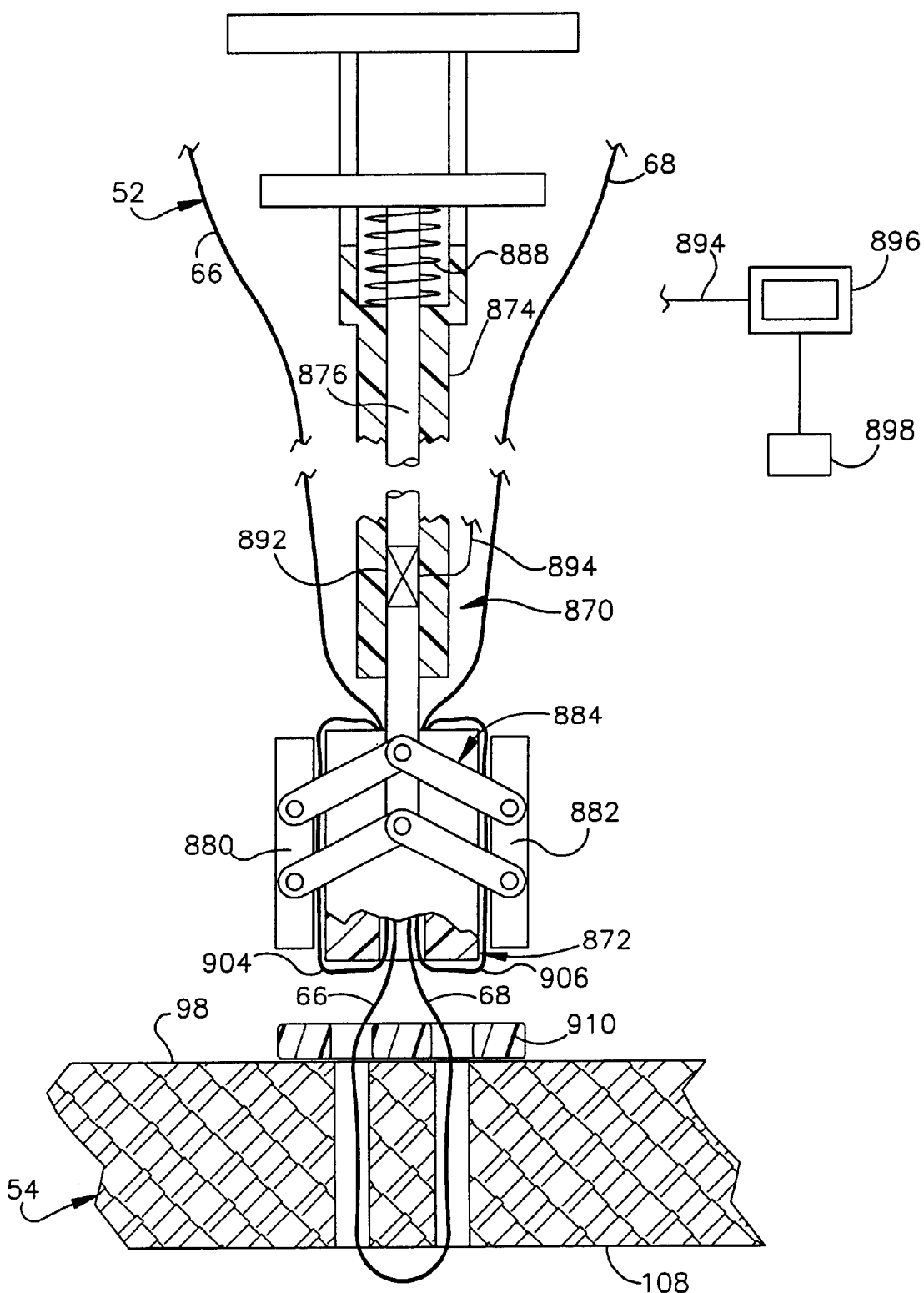
FIG. 36 is a schematic illustration of another embodiment of a tool which may be used to press a suture retainer against body tissue and to plastically deform the material of the suture retainer.

Embodiment of the Invention Illustrated in FIG. 36

In the embodiment of the invention illustrated in FIG. 35, an apparatus 770 for installing a suture retainer 772 is disclosed. In the embodiment of the invention illustrated in FIG. 36, a second apparatus for installing a suture retainer is disclosed. Since the embodiment of the invention illustrated in FIG. 36 is similar to the embodiment of the invention illustrated in FIG. 35, similar terminology will be utilized to identify similar components.

An apparatus or tool 870 for positioning a suture retainer 872 relative to body tissue 54 includes a base or housing 874. A cylindrical plunger 876 is slidable in the housing 874.

The plunger 876 is connected with left and right force application or clamp members 880 and 882 by a pair of linkages 884. Although only one of the linkages 884 has been shown in FIG. 36, it should be understood that there is a second linkage having the same construction as the linkage 884 connected with the plunger 876.

A biasing spring 888 extends around the plunger 876 and urges the plunger upward (as viewed in FIG. 36). The force transmitted from the biasing spring 888 through the plunger 876 and linkages 884 urges the left and right force application members 880 and 882 into engagement with the suture retainer 872. The force provided by the spring 888 is insufficient to cause significant deformation of the suture retainer 872. However, the force provided by the spring 888 is sufficient to enable the force application members 880 and 882 to hold the suture retainer 872 during sliding of the suture retainer along the suture 52.

A transducer or load cell 892 is connected with the plunger 876 and provides an output signal, over a lead 894 to a display unit 896. This output is indicative of the magnitude of the force transmitted through the plunger 876. When a predetermined force has been applied by the force application members 880 and 882 against the suture retainer 872 for a predetermined minimum length of time, an indicator 898 is activated by the display unit 896.

The specific suture retainer 872 illustrated in FIG. 36 has a one-piece tubular cylindrical construction. The suture 52 has left and right sections 66 and 68 which are wrapped around the suture retainer 872 in the same manner as in which the suture 52 is wrapped around the suture retainer 50 of FIG. 2. Thus, a loop 904 is formed in the left section 66 of the suture 52 and extends around a portion of the tubular cylindrical suture retainer 872. Similarly, a loop 906 is formed in the right section 68 of the suture 52 and extends around a portion of the tubular cylindrical suture retainer 872.

In the embodiment of the invention illustrated in FIG. 36, a force distribution member or button 910 is provided at the upper side surface 98 of the body tissue 54. The force transmission member or button 910 distributes the force applied by the suture retainer 872 to the body tissue 54 over a relatively large area on the body tissue. If desired, a second force distribution member could be provided between the suture and a lower side surface 108 of the body tissue 54. Since the suture retainer 872 is effective to apply force to a relatively large area, the button 910 may be omitted if desired.

When the suture retainer 872 is to be installed in the body tissue, the two sections 66 and 68 of the suture are sewn through the body tissue 54 and are then inserted into the suture retainer 872. During insertion of the left and right sections 66 and 68 of the suture 52 into the suture retainer 872, the loops 904 and 906 are formed in the two sections 66 and 68 of the suture.

The plunger 876 is then manually moved downward in the housing 874 against the influence of the biasing spring 888 to move the force application members 880 and 882 apart. When the force application members 880 and 882 have been positioned adjacent to opposite sides of the suture retainer 872, the downward force applied against the plunger 876 is released. This results in the biasing spring 888 moving the plunger 876 upward to actuate the linkages 884 to press the force application members 880 and 882 against opposite sides of the suture retainer 874.

The left and right sections 66 and 68 of the suture 52 are then tensioned. The apparatus or tool 870 is then moved along the left and right sections 66 and 68 of the suture 52 toward the body tissue. As this occurs, the loops 904 and 906 are displaced downwardly along the tensioned sections 66 and 68 of the suture 52 toward the body tissue. During downward displacement of the loops 904 and 906 toward the body tissue 54, the left and right sections 66 and 68 of the suture 52 slide along surfaces on the suture retainer 872.

After the suture retainer 872 has been moved into engagement with the button or force distribution member 910, the leading end of the suture retainer 872 is pressed against the button with a predetermined force. This force is transmitted through the plunger 876 and is measured by the transducer 892. Once the suture retainer 872 has been pressed against the button or force distribution member 910 with a predetermined force, the plunger 876 is manually pulled upward relative to the housing 874. This results in the transmission of force through the linkage 884 to the force applying members 880 and 882.

The force applying members 880 and 882 apply sufficient force to the suture retainer 872 to effect plastic deformation of the suture retainer. At this time, the suture retainer is at a temperature below the transition temperature of the biodegradable polymeric material of the suture retainer. Thus, the suture retainer is at a temperature which is the same as the temperature of the body tissue 54. The plastic deformation of the suture retainer 872 results in cold flowing of the material of the suture retainer and gripping of the left and right sections 66 and 68 of the suture 52 in the manner previously explained in conjunction with the embodiments of the invention illustrated in FIGS. 1–35.

It should be understood that the tool 870 may be used to install any of the suture retainers illustrated in FIGS. 1–33. Of course, the force application or clamp members 880 and 882 would be configured so as to grip the outer side surface of the specific suture retainer with which the tool is to be used.

Embodiment of FIGS. 37 and 38

In the embodiment of the invention illustrated in FIGS. 37 and 38, the suture is tensioned with a force which is a function of a selected suture size and strength. Since the embodiment of the invention illustrated in FIGS. 37 and 38 is similar to the embodiments of the invention illustrated in FIGS. 1–36, similar terminology will be utilized to identify similar components.

A chart 918 setting forth various available suture sizes is illustrated schematically in FIG. 37. The chart 918 also sets forth the strength of each of the available suture sizes. It is contemplated that the specific strength of a particular suture size may vary depending upon the material from which the suture is constructed and the manufacturer of the suture. By consulting the chart 918, a surgeon can select a suture of a size and strength suitable for a particular use. Thus, a relatively large suture having substantial strength may be selected when body tissue is to be connected with a bone or when portions of a bone are to be interconnected by the suture. On the other hand, the relatively small suture size having a relatively small strength may be selected when delicate body tissue, such as stomach or intestinal tissue, is to be interconnected with the suture.

Once a suture of a size and strength suitable for retaining specific body tissue has been selected, the suture is connected with body tissue and a retainer is moved along the suture toward the body tissue. Force is transmitted from the suture retainer and from the suture to the body tissue. The magnitude of the force which is transmitted from the suture retainer and the suture to the body tissue will be a function of the selected size and strength of the suture.

The suture retainer may have any one of the constructions illustrated in FIGS. 1 through 36. Alternatively, the suture retainer could have any one of the constructions illustrated in U.S. Pat. No. 5,593,425. It is contemplated that the suture could be connected with body tissue in any one of the manners illustrated in U.S. Pat. Nos. 5,593,425; 5,584,862; 5,549,631; 5,527,343; and/or 5,464,426.

In the embodiment of the invention illustrated in FIG. 38, a suture 922 extends through body tissue 924. The body tissue 924 includes an inner layer 926 of body tissue and an outer layer 928 of body tissue. A first or inner end portion 932 of the suture 922 is connected with a suture anchor 934.

The suture anchor 934 could have any desired construction. For example, the suture anchor 934 could have a construction similar to any one of the constructions disclosed in U.S. Pat. Nos. 5,584,862; 5,549,631; and/or 5,527,343. However, the illustrated embodiment of the suture anchor 934 is a circular disk or button having a pair of central openings around which the end portion 932 of the suture 922 is tied.

The suture 922 extends straight through the inner layer 926 and outer layer 928 of body tissue 924. An outer side surface 938 of the inner layer of body tissue 926 is engaged by an inner side surface 940 of the outer layer 928 of body tissue. The side surfaces 938 and 940 of the two segments or layers 926 and 928 of body tissue are disposed in flat apposition. Thus, the outer side surface 938 of the inner layer 926 is disposed in flat abutting engagement with the inner side surface 940 of the outer layer 928 where the suture 922 extends through the inner and outer layers.

A suture retainer 944 cooperates with the suture anchor 934 to hold the suture 922 against movement relative to the body tissue 924. The suture retainer 944 has a spherical configuration. A cylindrical passage 946 extends axially through the suture retainer 944.

Although the suture 922 (FIG. 38) extends straight through the passage 946 in the suture retainer 944, bends and/or loops could be formed in the suture 922 around the suture retainer 944 in the manner illustrated in FIG. 2. Thus, two bends, corresponding to the bends 72 and 74 of FIG. 2, could be formed in the suture 922 by wrapping a turn of the suture around a portion of the suture retainer 944. This will result in the formation of a single loop, corresponding to the loop 86 of FIG. 2, around the suture retainer 944.

The suture retainer 944 is formed of one piece of spherical polymeric material having a relatively low coefficient of friction. The suture retainer 944 may be formed of many different materials. However, it is believed that it will be preferred to form the suture retainer 944 of a biodegradable polymer. One biodegradable polymer which may be utilized is polycaperlactone. Alternatively, the suture retainer 944 could be formed of polyethylene oxide terephthalate or polybutylene terephthalate. It is also contemplated that other biodegradable or bioerodible copolymers could be utilized if desired.

Although it is preferred to form the suture retainer 944 of a biodegradable material, the suture retainer could be formed of a material which is not biodegradable. For example, the suture retainer could be formed of acetyl resin, such as "Delrin" (trademark). Alternatively, the suture retainer 944 could be formed of para-dimethylamino-benzenediazo sodium sulfonate, such as "Dexon" (trademark).

The suture 922 may be formed of natural or synthetic materials. The suture 922 may be a monofilament or may be formed of a plurality of interconnected filaments. The suture 922 may be biodegradable or non-biodegradable. It may be preferred to form the suture 922 of the same material as the suture retainer 944. However, the suture 922 could be formed of a material which is different than the material of the suture retainer.

In accordance with a feature of the embodiment of the invention illustrated in FIGS. 37 and 38, the suture 922 is tensioned with a force which is a function of the size and strength of the suture, as indicated by the chart 918. In addition, the suture retainer 944 is pressed against the body tissue 924 with a force which is also a function of the size and strength of the suture 922, as indicated by the chart 918 of FIG. 37. Although the suture 944 is disposed in direct engagement with and is pressed against an outer side surface 950 of the outer layer or segment 928 of body tissue 924, a force distribution member or button could be positioned between the suture retainer 944 and the outer side surface 950 of the outer layer 928 of body tissue.

The suture 922 is tensioned by a force application assembly 954 which is connected with the second or outer end portion 956 of the suture 922. The force application assembly 954 includes a transducer or load cell 958 which provides an output signal indicative of a force, indicated schematically at 960 in FIG. 38 which is applied to the second or outer end portion 956 of the suture 922. The force 960 has a magnitude which is a function of the size and strength of the suture 922, as indicated by the chart 918. Thus, the force 960 may be equal to 0.80 times the strength of the suture 922 as indicated by the chart 918. Of course, the strength of the suture 922 will vary with variations in the size of the suture 922.

The suture retainer 944 is pressed against the outer side surface 960 of the outer layer or segment 928 of body tissue 924 with a force which is also a function of the strength and size of the suture 922, as indicated by the chart 918 of FIG. 37. A force application member 964 is used to apply force against the suture retainer 922. The force application member 964 has a cylindrical opening 966 which extends through the force application member. The suture 922 extends through the opening 966. A slot may be formed in the force application member 964 to enable the suture 922 to be moved into the opening 966. Alternatively, the suture 922 could be inserted through the opening 966 before the end portion 956 of the suture is connected with the force application assembly 954.

Forces, indicated schematically at 968 and 970 in FIG. 38, are applied against opposite end portions 972 and 974 of the force application member 964 to press the suture retainer 944 directly against the outer layer 928 of body tissue or against a force transmitting member disposed between the suture retainer 944 and the outer layer 928 of body tissue. The combined force, indicated schematically the arrows 968 and 970 in FIG. 38, is a function of the size and strength of the suture 922, as indicated by the chart 918. It is contemplated that the combined forces 968 and 970 may be equal to the force 960. In the specific example previously mentioned, this would result in the forces 968 and 970 having a sum or total equal to 0.80 times the strength of the suture 922 as indicated by the chart 918. Alternatively, the summation of the forces 968 and 970 could exceed the force 960 or be less than the force 960.

The suture retainer 944 slides downward (as viewed in FIG. 38) along the suture 922 under the influence of the force application member 964. At this time, the suture 922 is tensioned by the force application assembly 954 so that the portion of the suture extending between the suture anchor 934 and the force application assembly 954 is straight, as illustrated in FIG. 38. However, at this time, the force which is applied to the outer end portion 956 of the suture 922 by the force transmitting assembly 954 may be substantially less than the force which is indicated schematically by the arrow 960 in FIG. 38.

After the suture retainer 944 has been moved along the suture 922 to the position illustrated in FIG. 38, the force applied against the suture retainer by the force application member 964 is increased. At the same time, the force applied to the outer end portion 956 of the suture 922 by the force application assembly 954 is increased. The force applied against the suture retainer 944 by the force application member 964 is increased until the force, indicated schematically by the arrows 968 and 970 in FIG. 38, is equal to a predetermined function of the strength of the suture 922, as indicated by the chart 918 for the particular size of the suture. At the same time, the force applied to the outer end portion 956 of the suture 922 by the force application assembly 954 is increased to the force indicated schematically by the arrow 960 in FIG. 38. As was previously mentioned, the force indicated by the arrow 960 is a predetermined function of the strength of the suture 922 as indicated by the chart 918.

While the suture 922 is being pulled straight under the influence of tension in the suture due to the force 960 and while the suture retainer 944 is being pressed against outer layer 928 of body tissue or against a suitable force distribution member, the suture retainer 944 is plastically deformed to firmly grip the suture 922. Thus, while the suture retainer 944 is being pressed against the outer layer 928 of body tissue 924 under the combined forces 968 and 970 and while the suture 922 is being tensioned by the force 960, a pair of force application members 978 and 980 are pressed against opposite sides of the suture retainer 944. The force applied against the suture retainer 944 by the force application members 978 and 980 plastically deforms the material of the suture retainer.

In the illustrated embodiment of the invention, the plastic deformation of the suture retainer 944 is effective to cause cold flowing of the material of the suture retainer. Force indicated by arrows 982 and 984 in FIG. 38, is applied against the suture retainer 944 by the force application members 978 and 980. This force is effective to cause flowing of the material of the suture retainer 944 at a temperature below the transition temperature range of the material of the suture retainer. Although the illustrated force application members 978 and 980 have flat force transmitting surfaces, each of the force transmitting members could have force transmitting surfaces with a configuration corresponding to the configuration of a portion of a sphere.

The cold flowing of the material of the suture retainer 944 results in collapsing of the passage 946 and in flowing of the material of the suture retainer 944 around the portion of the suture 922 extending through the passage 946. This enables the material of the suture retainer 944 to bond to and obtain a firm grip on the suture 922. The cold flowing of the material of the suture retainer 944 occurs at a temperature which is below the transition temperature of the material forming the suture retainer.

It is believed that it may be preferred to plastically deform the material of the suture retainer 944 (FIG. 38) by applying force against areas on the suture retainer and cold flowing material of the suture retainer in the manner previously explained. However, if desired, the suture retainer 944 may be heated before the force application members 982 and 984 apply force against the suture retainer. The heated material of the suture retainer will be moved into engagement with a portion of the suture 922 extending through the passage 946.

The temperature to which the material of the suture retainer is heated would be low enough so that the heated material would not cause significant deformation of the material of the suture 922. Thus, the material of the suture retainer 944 may be heated to a temperature within its transition temperature range but less than a temperature which would result in a complete melting of the material of the suture retainer. As the material of the suture retainer 944 is pressed against the suture 922 by the force application members 978 and 980, the heated plastic material of the suture retainer is cooled to a temperature below its transition temperature range. As this occurs, the plastic material of the suture retainer 944 bonds to a portion of the suture 922 without significant deformation of the suture.

The interconnection between the material of the suture retainer 944 and the portion of the suture 922 extending through the suture retainer is the result of both molecular attraction (adhesion) of the material of the retainer to the material of the suture and due to a mechanical interconnection between the material of the suture retainer and the material of the, suture. Thus, as the material of the suture retainer 944 cools, it mechanically grips the suture 922 so that the suture is held against movement relative to the suture retainer by interfacial forces between the material of the suture retainer and the material of the suture. There is a fusing of the material of the suture retainer 944 to the material of the suture 922 along the portion of the suture which extends through the suture retainer.

Whether the suture retainer 944 is plastically deformed by cold flowing the material of the suture retainer or by a flowing of heated material of the suture retainer, the suture retainer grips the suture 922 without significant deformation of the suture. Therefore, the strength of the suture 922 is not impaired and corresponds to the strength indicated by the chart 918 for the particular size of the suture.

When the layers or segments 926 and 928 of the body tissue 924 are to be interconnected with the suture 922, the end portion 932 of the suture is connected with an anchor member 934. The suture 922 is then threaded with a needle or similar device, through the layers 926 and 928 of body tissue.

It should be understood that in certain situations, a surgeon will not have access to both the inner and outer sides of the body tissue. In situations where the surgeon does not have access to both sides of the body tissue, the anchor 934 is formed with a configuration which enables it to be inserted through the layers or segments 926 and 928 of body tissue along with the suture 922. Thus, the end portion 932 of the suture 922 is connected with the anchor 934 while the anchor and suture are both disposed outside of the patient's body.

The suture anchor, with the suture 922 connected thereto, is then inserted through both layers 926 and 928 of the body tissue 924. This may be accomplished in the manner disclosed in U.S. Pat. No. 5,464,426. However, it should be understood that the suture anchor could have a configuration other than the specific configuration disclosed in U.S. Pat. No. 5,464,426. For example, the suture anchor 934 could have a configuration similar to any one of the configurations disclosed in U.S. Pat. No. 5,527,343.

In the embodiment of the invention illustrated in FIG. 38, the suture anchor 934 is positioned in engagement with an inner side surface 988 on the inner layer 926 of body tissue. It is contemplated that the suture anchor 934 could be disposed within the inner layer 926 of body tissue. Thus, the suture anchor could be disposed at a location midway between the inner side surface 988 and the outer side surface 938 of the layer 926 of body tissue. Mounting of the suture anchor in the body tissue in this manner would be particularly advantageous if the suture anchor is mounted in bone in the manner illustrated in the aforementioned U.S. Pat. No. 5,527,343.

Although the suture retainer 944 has been illustrated in FIG. 38 as having a spherical construction, generally similar to the suture retainer of FIGS. 1 and 2, it is contemplated that the suture retainer 944 could have a configuration corresponding to the configuration of any one of the suture retainers illustrated in FIGS. 1 through 36 herein.

Figure 39:
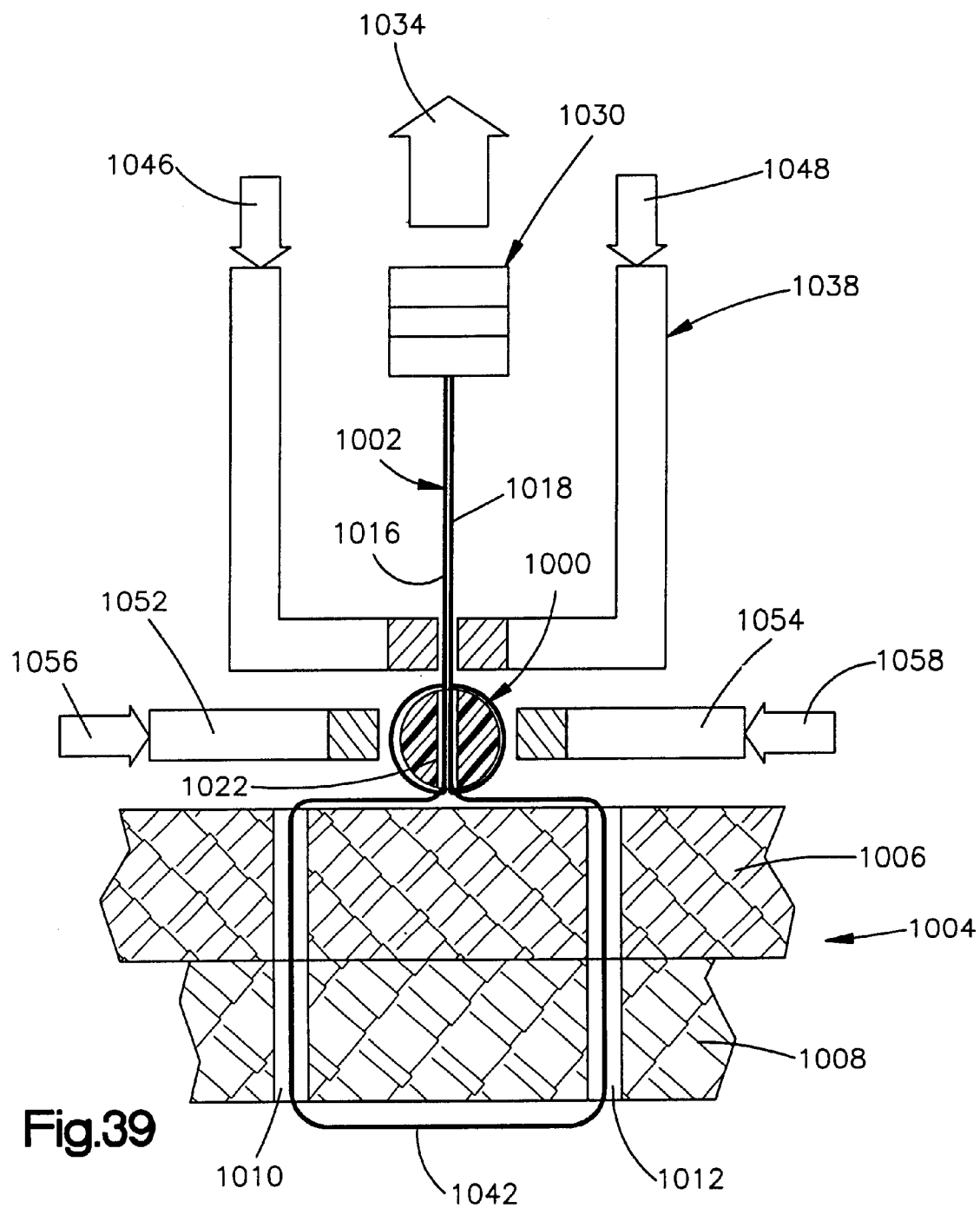
FIG. 39 is a schematic illustration, generally similar to FIG. 38, illustrating another embodiment of the invention.

Embodiment of FIG. 39

In the embodiment of the invention illustrated in FIGS. 37 and 38, the suture 922 has a single section which extends through the suture retainer. In the embodiment illustrated in FIG. 39, the suture has a plurality of sections which extend through the suture retainer. Since the embodiment of the invention illustrated in FIG. 39 is similar to the embodiment of the invention illustrated in FIGS. 1–38, similar terminology will be utilized to identify similar components. It should be understood that one or more features of the embodiment of the invention illustrated in FIGS. 1–38 may be used with the embodiment of the invention illustrated in FIG. 39.

A suture retainer 1000 (FIG. 39) is utilized to secure a known suture 1002 against movement relative to body tissue 1004. The suture 1002 extends through an outer layer 1006 and an inner layer 1008 of the body tissue. The suture 1002 has been illustrated schematically in FIG. 39 as extending through passages 1010 and 1012 in the outer and inner layers 1006 and 1008 of body tissue 1004. However, the suture 1002 could be sewn through the body tissue 1004 without forming the passages 1010 and 1012 in the body tissue.

Although the suture 1002 has been shown in FIG. 39 in association with soft body tissue, it is contemplated that the suture 1002 could be associated with hard body tissue. It is also contemplated that the suture 1002 could extend through a suture anchor in a manner similar to that disclosed in U.S. Pat. Nos. 5,584,862; 5,549,631; and/or 5,527,343.

The suture 1002 has a left section 1016 and a right section 1018. The left and right sections 1016 and 1018 of the suture 1002 extend through the suture retainer 1000. If desired, the suture 1002 could be integrally formed as one piece with the suture retainer 1000. If this was done, the end of the section 1016 or 1018 of the suture 1002 would be connected with the suture retainer 1000. Alternatively, a single section of the suture 1002 could extend through the suture retainer, in the manner illustrated for the embodiment of FIG. 38.

Although the sections 1016 and 1018 of the suture 52 could extend straight through the suture retainer 1000, as shown in FIG. 38 for the suture 922, it is preferred to form a plurality of bends in the suture 1002. In the illustrated embodiment, bends are formed in the left and right sections 1016 and 1018 of the suture 1002 by wrapping a turn of the left section 1016 around a portion of the suture retainer 1000. Similarly, bends are formed in the right section 1018 of the suture 1002 by wrapping a turn in the right section of the suture around a portion of the suture retainer 1000. A single loop is formed in the left section 1016 of the suture 1002 around a portion of the suture retainer 1000. Similarly, a single loop is formed in the right section 1018 around a portion of the suture retainer 1000. A greater or lesser number of loops could be provided in the left and right sections 1016 and 1018 if desired. The suture 1002 cooperates with the suture retainer 1000 in the same manner as is illustrated in FIGS. 1 and 2 herein.

The suture retainer 1000 has a spherical configuration. A cylindrical passage 1022 extends diametrically through the spherical suture retainer 1000. If desired, the suture retainer 1000 could have a different configuration. For example, the suture retainer 1000 could have any one of the configurations illustrated in FIGS. 1 through 36. If desired, a plurality of passages having the same or different configurations, could be provided in the suture retainer 1000.

A surgeon selects the suture 1002 to have a particular size and strength in accordance with a chart, corresponding to the chart 918 of FIG. 37. A force application assembly 1030 is connected with end portions of the left and right sections 1016 and 1018 of the suture 1002. The force application assembly 1030 tensions the suture 1002 with a force, indicated schematically by an arrow 1034 in FIG. 39.

In addition, a force application member 1038 applies force against the suture retainer 1000 urging the suture retainer towards the body tissue 1004. The force applied by the force application member 1038 to the suture retainer 1000 moves or slides the suture retainer along the suture 1002 toward the body tissue 1004. In the embodiment of the invention illustrated in FIG. 39, the suture retainer 1000 is pressed against the outer layer 1006 of body tissue under the influence of force applied against the suture retainer 1000 by the force application member 1038. However, if desired, a force distribution member, such as a button, could be provided between the suture retainer 1000 and the body tissue 1004. In addition, a force distribution member or button could be provided between a connector section 1042 of the suture 1002 and the inner layer 1008 of body tissue.

In accordance with a feature of this embodiment of the invention, the suture 1002 is tensioned by the force application assembly 1030, with a force 1034 which is a function of the strength of the suture 1002. In accordance with another feature of this embodiment of the invention, the force application member 1038 is effective to apply forces indicated schematically by arrows 1046 and 1048, which are a function of the strength of the suture 1002, to the suture retainer 1000.

The combined effects of the force application assembly 1030 and the force application member 1038 result in the left and right sections 1016 and 1018 of the suture 1002 being tensioned with a force which is a function of the strength of the suture 1002 and in the transmission of a force from the suture retainer 1000 to the body tissue 1004 which is a function of the strength of the suture 1002. Thus, the force 1034 is a function of the strength of the suture 1002. For example, the force 1034, with which the suture 1002 is tensioned, may be equal to 0.80 times the strength of the suture. Similarly, the combined forces 1046 and 1048 which are transmitted from the suture retainer 1000 to the body tissue 1004 may be 0.80 times the strength of the suture.

While the suture 1002 is being tensioned with the force 1034 and while the forces 1046 and 1048 are being applied to the suture retainer 1000 to press the suture retainer against the body tissue, force application members 1052 and 1054 are effective to apply forces, indicated schematically by arrows 1056 and 1058 against the suture retainer 1000. The force applied by the force application members 1052 and 1054 plastically deforms the material of the suture retainer 1000.

The plastic deformation of the suture retainer 1000 is effective to cause cold flowing of material of the suture retainer. The force indicated by the arrows 1056 and 1058 is applied against the suture retainer 1000 by the force application members 1052 and 1054 for a predetermined length of time. This force is effective to cause flowing of the material of the suture retainer 1000 at a temperature below the transition temperature range for the material of the suture retainer. Although the illustrated force application members 1052 and 1054 have flat force transmitting surfaces, each of the force application members 1052 and 1054 could have force transmitting surfaces with a configuration which corresponds to the configuration of a portion of a sphere.

The cold flowing of the material of the suture retainer 1000 results in a collapsing of the passage 1022 and the flowing of the material of the suture retainer around the sections 1016 and 1018 of the suture 1002. This enables the material of the suture retainer 1000 to bond to and obtain a firm grip on the suture 1002. The cold flowing of the material of the suture retainer 1000 occurs at a temperature which is below the transition temperature of the material forming the suture retainer.

During the time in which the force application members 1052 and 1058 are effective to apply force against the suture retainer 1000, the suture retainer is pressed against the outer layer 1006 of the body tissue 1004 under the combined influence of the forces 1046 and 1048 which are a function of the strength of the suture 1002. In addition, a predetermined tension is maintained in the sections 1016 and 1018 of the suture 1002 by the force application assembly 1030. Thus, the sections 1016 and 1018 of the suture 1002 tension with a force 1034 which is a function of the strength of the suture 1002 while the force application members 1052 and 1054 are effective to plastically deform the material of the suture retainer 1000.

Once the suture retainer 1000 has been plastically deformed to grip the suture 1002, the force transmitting members 1052 and 1054 disengage from the suture retainer 1000. At the same time, the force application member 1038 is moved away from the suture retainer 1000 and the force application assembly 1030 interrupts the application of tensioning force to suture 1002. The suture retainer 1000 grips the suture 1002 and maintains the tension in the portions of the sections 1016 and 1018 of the suture which extend through the passages 1010 and 1012 even through the force application assembly 1030 is no longer effective to tension the suture.

The suture retainer 1000 may be formed of many different materials. However, it is believed that it will be preferred to form the suture retainer of a biodegradable polymer. Although it is preferred to form the suture retainer 1000 of a biodegradable material, the suture retainer could be formed of a material which is not biodegradable.

In the illustrated embodiment of the invention, the suture 1002 is formed of the same material as the suture retainer 1000. The suture 1002 may be formed of a natural or synthetic material and may be a monofilament or formed by a plurality of interconnected filaments. The suture 1002 may be biodegradable or non-biodegradable.

In the foregoing description, the material of the suture retainer 1000 has been plastically deformed by cold flowing of the material of the suture retainer. It is contemplated that the suture retainer 1000 could be heated to a temperature in the transition temperature range for the material of the suture retainer. The force application members 1052 and 1054 could apply force against the heated material of the suture retainer 1000 to cause a flowing of the heated material of the suture retainer.

Embodiment of FIGS. 40–42

A suture retainer 1070 (FIG. 42) includes a holder or retainer member 1072 (FIG. 40) and a tubular member 1074 (FIG. 41). The suture retainer 1070 is utilized to secure a known suture 1076 against movement relative to by tissue 1078 (FIG. 42). In the embodiment of the invention illustrated in FIG. 42, the suture 1076 is connected with a suture anchor 1082. However, the suture 1076 could be connected with body tissue in many different ways, including those illustrated in FIGS. 1, 9, 26, 36, 38, and 39 herein. The suture anchor 1082 could have any one of many different known constructions, including the constructions illustrated in U.S. Pat. Nos. 5,584,862; 5,549,631; and/or 5,527,343. It should be understood that one or more of the features of the embodiments of the invention illustrated in FIGS. 1–39 could be used with the embodiment of the invention illustrated in FIGS. 40–42.

The tubular member 1074 (FIG. 41) has a cylindrical outer side surface 1086. The outer side surface 1086 extends between annular end surfaces 1088 and 1090 disposed at axially opposite ends of the tubular member 1074. A cylindrical passage 1092 extends between the axially opposite end surfaces 1088 and 1090 of the tubular member 1074. Although the tubular member 1074 has been illustrated in FIG. 41 has having a cylindrical outer side surface 1086, it is contemplated that the tubular member 1074 could have an outer side surface with a different configuration, for example, a rectangular configuration.

A notch or recess 1096 may be formed in the tubular member 1074. The notch 1096 is disposed midway between the end surfaces 1088 and 1090. The notch 1096 extends through the passage 1092. Although it is preferred to form the notch 1096 in the tubular member 1074, it is contemplated that the notch could be omitted if desired. If the notch 1096 is omitted, the cylindrical outer side surface 1086 would extend between the opposite end surfaces 1088 and 1090 and would be free of discontinuities.

The holder member 1072 (FIG. 40) has a generally C-shaped configuration. The holder member 1072 includes a main section 1100 and pair of leg sections 1102 and 1104. In the illustrated embodiment of the invention, the main section 1100 and leg sections 1102 and 1104 have a rectangular cross-sectional configuration. However, it is contemplated that the main section 1100 and leg sections 1102 and 1104 could have a different cross-sectional configuration if desired.

The leg sections 1102 and 1104 extend perpendicular to the main section 1100. However, it should be understood that the main section 1100 and leg sections 1102 and 1104 could have a different configuration if desired. For example, the main section 1100 and leg sections 1102 and 1104 could have a circular cross-sectional configuration. The leg sections 1102 and 1104 could be skewed in an acute angle to central axis of the main section 1100.

A pair of flanges 1108 and 1110 extend toward each other from outer end portions of the leg sections 1102 and 1104 (FIG. 40). The flanges 1108 and 1110 define an opening 1112 to a recess 1114 defined by the holder member 1172. The illustrated recess 114 has a polygonal configuration. However, the recess 114 could have an arcuate configuration if desired.

The flanges 1108 and 1110 have straight edges 1118 and 1120 which extend parallel to each other and perpendicular to the central axis of the leg sections 1102 and 1104. Although it is preferred to form the flanges 1108 and 1110 with straight edges 1118 and 1120, the flanges could be formed with edges having a different configuration, for example, a curved configuration.

The tubular member 1174 (FIG. 41) and the holder member 1072 are formed of a polymeric material having a relatively low coefficient to friction. The polymeric material forming the holder member 1072 and tubular member 1074 is biodegradable. One biodegradable polymer which may be utilized to form the holder member 1072 and tubular member 1074 is polycaperlactone. Alternatively, the holder member 1072 and tubular member 1074 could be formed of polyethylene oxide terephthalate or polybutylene terephthalate. It is contemplated that other biodegradable or bioerodible copolymers could be utilized if desired. If desired, the holder member 1072 could be formed of one known biodegradable copolymer and the tubular member 1074 could be formed of a different biodegradable copolymer.

Although it is preferred to form the holder member 1072 and tubular member 1074 of a biodegradable material, they could be formed of a material which is not biodegradable. For example, the holder member 1072 and/or the tubular member 1074 could be formed of an acetyl resin, such as "Delrin" (Trademark). Alternatively, the holder member 1072 and/or tubular member 1074 could be formed of a para-dimethylamino-benzenediazo sodium sulfonate, such as "Dexon" (Trademark). If desired, either the holder member 1072 or the tubular member 1074 could be formed of a material which is biodegradable and the other member formed of a material which is not biodegradable.

When the suture retainer 1070 (FIG. 42) is to be used to secure the suture 1076 relative to the body tissue 1078, the suture is inserted through the passage 1092 in the tubular member 1074, in the manner illustrated in FIG. 41. The tubular member 1074 is then slid along the suture 1076 toward the body tissue 1078 with the end surface 1090 of the tubular member leading. The end surface 1090 of the tubular member is moved through the opening 1112 (FIG. 40) in the holder member 1072.

Although only a single section of the suture 1076 extends through the tubular member 1074, two or more sections of the suture could extend through the tubular member 1074. For example, a pair of sections of the suture 1076 could extend through the tubular member 1074 in much the same manner as in which a pair of sections 66 and 68 of a suture 52 extend through the main section 704 of the suture retainer 700 of FIG. 32.

The suture 1076 is then tensioned with a predetermined force which is a function of the known size and strength of the suture. The leg section 1104 of the holder member 1072 is pressed against the body tissue 1178 (FIG. 42) with a predetermined force. The leading end portion of the tubular member 1074 is then pressed firmly against the leg section 1104 of the holder member 1072 with a predetermined force which corresponds to the force with which the holder member is pressed against the body tissue 1078.

The tubular member 1074 is then bent at the notch 1096. This resiliently deforms the tubular member 1074 from the linear configuration illustrated in FIG. 41 to the bent configuration illustrated in FIG. 42. As the tubular member 1074 is elastically bent, the predetermined tensioned is maintained in the suture 1076.

While the tubular member 1074 is being pressed against the holder member 1072 with a force sufficient to apply a predetermined force against the body tissue 1078 through the holder member, the tubular member 1074 is resiliently bent from the straight configuration of FIG. 41 to the bent configuration of FIG. 42. As this occurs, the trailing end portion of the tubular member 1074, on which the end surface 1088 is located, is moved into the recess 1114 (FIG. 40) in the holder member 1072. The bent tubular member 1074 has the generally V-shaped configuration illustrated in FIG. 42.

The edges 1018 and 1020 (FIG. 40) on the flanges 1108 and 1110 press against the outer side surface 1086 (FIG. 41) of the tubular member 1074 to hold the tubular member against resiliently springing outward from the generally V-shaped configuration to which the tubular member has been resiliently deflected (FIG. 42). At this time, an arcuate bend portion 1124 of the tubular member 1074 extends out of the recess 1114 in the holder member 1072 through the opening 1112. The linear edges 1118 and 1120 of the flanges 1108 and 1110 apply force against the tubular member 1074 to hold the tubular member in the generally V-shaped configuration illustrated in FIG. 42.

The suture 1076 is firmly gripped by the portion of the passage 1092 extending through the bend portion 1124 of the tubular member 1074. Gripping of the suture 1076 is promoted by the notch 1096 (FIG. 41). The notch 1096 results in surfaces on the tubular member 1074 which form the portion of the passage 1092 intersecting the notch 1096 engaging the suture 1076 to hold the suture.

The generally V-shaped configuration of the resiliently deflected tubular member 1074 (FIG. 42) results in the suture 1076 being held with sufficient force to maintain the predetermined tension in the portion of the suture extending between the bend portion 1124 of the tubular member 1074 and the suture anchor 1082. This tension results in the tubular member 1074 being pressed against the holder member 1072 with sufficient force to press the leg section 1104 of the holder member 1072 against the body tissue 1078 with a predetermined force.

Once the tubular member 1074 has been bent and positioned in the recess 1114 in the holder member 1072, in the manner illustrated schematically in FIG. 42, the suture retainer 1070 may be plastically deformed to increase the grip of the tubular member 1074 on the suture 1076. Thus, if desired, while the predetermined tension is present in the suture 1076 and while the holder member 1072 is being pressed against the body tissue 1078 with a predetermined force, force is applied against opposite sides of the suture retainer 1070. The force is applied to the suture retainer in a direction extending perpendicular to the longitudinal central axis of the main section 1100 of the holder member 1072 and extending through the center of the recess 1114. The force applied against the suture retainer 1070 plastically deforms both the holder member 1072 and the tubular member 1074.

The plastic deformation of the holder member 1072 and tubular member 1074 is effective to cause cold flowing of material of both the holder member and the tubular member. This force is effective to cause flowing of the material of the holder member 1072 and the tubular member 1074 at a temperature below a transition temperature range for the material of the holder member 1072 and tubular member 1074. The cold flowing of the material of the holder member 1072 and the tubular member 1074 results in a reduction in the size of the recess 114 in the holder member 1072 and a closing of the passage 1092 through the tubular member 1074.

As the material of the tubular member 1074 is plastically deformed at a temperature below the transition is temperature range of the material, there is a collapsing of the passage 1092 through the tubular member. This results in the material of the tubular member 1074 bonding to and obtaining a very strong grip on the suture 1076. The manner in which force is applied against opposite sides of the suture retainer 1072 may be similar to that illustrated schematically in FIGS. 3, 8, 18, 22, 32, 34, 35, and 38 herein.

Although it is believed that it may be preferred to apply force against both the holder member 1072 and tubular member 1074 (FIG. 42) to effect cold flowing of the material forming the holder member and tubular member, force may be applied against only the tubular member 1074 if desired. Thus, the force application members could be constructed so as to have a configuration corresponding to the configuration of the recess 114 in the holder member 1072 and to extend a short distance through the opening 1112 into the recess.

The force application members would be positioned in engagement with diametrically opposite sides of the tubular member 1074 and would be aligned with opposite ends of the recess 114. The force application members would then be moved toward each other along an axis extending through the center of the recess 1114 in a direction perpendicular to a longitudinal central axis of the main section 1100 of the holder member 1072. A predetermined force sufficient to cause cold flowing of the tubular member 1074 would then be applied against opposite sides of the tubular member. This would result in a cold flowing of the material of the tubular member 1074 and collapsing of the passage 1092 through the tubular member without significant deformation of the holder member 1072.

Regardless of whether the holder member 1072 and tubular member 1074 or just the tubular member 1074 are plastically deformed, the passage 1092 through the tubular member is collapsed and the material of the tubular member pressed firmly against the suture 1076. The force applied against the tubular member 1074 is sufficient to embed the suture 1076 in the material of the tubular member 1074 to obtain a cold bonding of the material of the tubular member 1074 with the suture 1076. A cold bonding of the material forming the inner side surface of the passage 1092 with the suture 1076 securely interconnects the suture and the tubular member 1074. The manner in which the material of the tubular member 1074 engages the suture 1076 is the same as is illustrated schematically in FIG. 4.

It is preferred to effect cold flowing of the material of the tubular member 1074 and, if desired, the material of the holder member 1072 without the addition of heat. However, it is contemplated that the tubular member 1074 and, if desired, the holder member 1072 could be heated to a temperature which is somewhat above the temperature of the body tissue 1078 (FIG. 42). Although the material of the holder member 1072 and tubular member 1074 could be heated into the transition temperature range for the materials forming the members, it is believed that it will be desired to maintain the temperature of the holder member 1072 and tubular member 1074 at a temperature below the transition temperature of the materials forming these member. However, it should be understood that in certain situations, it may be desired to heat the holder member 1072 and/or the tubular member 1074 to a temperature which is in the transition temperature range for the materials forming these members. If this was done, there would be a hot flowing, rather cold flowing of the material of the holder member 1072 and/or tubular member 1074.

The foregoing description has assumed that force will be applied against the suture retainer 1070, with or without the application of heat, to effect flowing of the material of the suture retainer. However, it is believed that it may be preferred to omit the application of force to the suture retainer 1070. Thus, the resiliently bent tubular member 1074 is held against movement from the bent condition of FIG. 42 under the influence of its own natural resilience, by the holder member 1072 to grip the suture 1076 without additional deformation of the suture retainer 1070. By omitting the application of force to the suture retainer 1070 after the tubular member 1074 has been bent and gripped by the holder member 1072, installation of the suture retainer is simplified.

In the embodiment of the invention illustrated in FIG. 42, the leg section 1104 of the holder member 1072 is pressed firmly against the body tissue 1078. If desired, a force distribution member could be provided between the holder member 1072 and the body tissue 1078. For example, a circular force distribution member having a central passage could be provided between the holder member 1072 and body tissue 1078. Alternatively, the leg section 1104 of the holder member 1072 could be provided with an enlarged base so as to have a larger area of engagement with the body tissue 1078.

In the embodiment of the invention illustrated in FIG. 42, opposite end surfaces 1088 and 1090 on the tubular member 1074 are disposed in the recess 1114. However, it is contemplated that bent tubular member 1074 could be inserted into the recess 1114 in the holder member 1072 with the bend portion 1124 disposed on one side of the holder member 1072 and the end surfaces 1088 and 1090 disposed on the opposite side of the holder member. This would result in the holder member 1072 functioning as a band which would extend around the tubular member 1074 at a location between the bent portion 1124 and the end surfaces 1088 and 1090. The band formed by the holder member 1072 would hold portions of the tubular member 74 in engagement with each other at a location offset from the bend portion 1124.

Embodiment of FIG. 43

In the embodiment of the invention illustrated in FIGS. 40–42, the tubular member 1074 is provided with a cylindrical outer side surface 1086 which is engaged by the edges 1118 and 1120 on the holder or retainer member 1072. In the embodiment of the invention illustrated in FIG. 43, the tubular member is provided with a pair of notches which are engaged by the holder member. Since the embodiment of the invention illustrated in FIG. 43 is similar to the embodiment of the invention illustrated in FIGS. 40–42, similar terminology will be utilized to designate similar components.

In the embodiment of the invention illustrated in FIG. 43, a tubular member 1130 has a cylindrical passage 1132 through which a suture 1134 extends. The tubular member 1130 has a cylindrical outer side surface 1136. A notch 1138 is formed midway between opposite end surfaces 1140 and 1142 on the tubular member 1130. The notch 1138 corresponds to the notch 1096 in the embodiment of the tubular member illustrated in FIG. 41.

In accordance with a feature of the embodiment of the invention illustrated in FIG. 43, a pair of notches 1146 and 1148 are formed in the cylindrical outer side surface 1136. The notches 1146 and 1148 are disposed on the right side (as viewed in FIG. 43) of the tubular member 1130 while the notch 1138 is formed in the opposite or left side of the tubular member. Although the notches 1146 and 1148 are located closer to the notch 1138 than they are to the end surfaces 1140 and 1142 of the tubular member 1130, the notch 1146 is located approximately halfway between the notch 1138 and the end surface 1140. Similarly, the notch 1148 is located approximately halfway between the notch 1138 and the end surface 1142 of the tubular member 1130.

When the tubular member 1130 is positioned in engagement with a holder member, in a manner similar to which the tubular member 1074 is positioned in engagement with the holder member 1072 in FIG. 42, flanges, corresponding to the flanges 1108 and 1110 on the holder member engage the notches 1146 and 1148 on the tubular member 1130. The presence of the notches 1146 and 1148 retards undesired relative movement between the tubular member 1130 and the holder member as the tubular member is inserted into the holder member, in the manner indicated schematically in FIG. 42 for the tubular member 1074.

Embodiment of FIG. 44

In the embodiment of the invention illustrated in FIGS. 40–42, the tubular member 1074 is resiliently deflected to form a single bend portion 1124 in the tubular member. In the embodiment of the invention illustrated in FIG. 44, a plurality of bend portions are formed in the tubular member 1074. Since the embodiment of the invention illustrated in FIG. 44 is similar to the embodiment of the invention illustrated in FIGS. 40–42, similar terminology will be utilized to identify similar components.

In the embodiment of the invention illustrated in FIG. 44, a suture retainer 1152 is utilized to secure a suture 1154 against movement relative to body tissue. Although the suture 1154 has been illustrated schematically in FIG. 44 as having slack, it is contemplated that at least a portion of the suture 1154 disposed between the suture retainer 1152 and a suture anchor, corresponding to the suture anchor 1082 in the body tissue 1078 of FIG. 42, will be tensioned with a predetermined force. Therefore, a predetermined tension is maintained in the suture 1154 and the suture retainer 1152 is pressed against the body tissue with a predetermined force.

The suture retainer 1152 includes a holder or retainer member 1158 which at least partially encloses a tubular member 1160. The holder member 1158 has a generally C-shaped configuration with a recess 1162 in which the tubular member 1160 is disposed. The recess 1162 has an opening 1164 through which the suture 1154 extends.

In the illustrated embodiment of the invention, the tubular member 1160 is disposed almost entirely within the recess 1162. Only a relatively insignificant portion of the tubular member 1158 extends through the opening 1164. If desired, the tubular member 1160 could have a length such that the entire tubular member 1160 is disposed in the recess 1162. Alternatively, the length of the tubular member 1160 could be such that opposite end portions of the tubular member 1160 project a substantial distance through the opening to the recess 1162.

In accordance with a feature of this embodiment of the invention, a pair of bend portions 1168 and 1170 are formed in the tubular member 1160. By resiliently deflecting the tubular member 1160 to form the bend portions 1168 and 1170, two portions of a passage 1174 through the tubular member 1160 are bent to grip the suture 1154. A pair of notches 1176 and 1178 are formed in the tubular member 1160. The notches 1176 and 1178 have the same configuration as the notch 1096 and perform the same function as the notch 1096 of FIG. 41.

When the suture retainer 1152 is to be utilized to secure the suture 1134 relative to body tissue, the tubular member 1160 is slid along the suture 1154 into engagement with the holder member 1158. At this time, the tubular member 1160 has a straight or linear configuration corresponding to the configuration of the tubular member 1074 of FIG. 41. The tubular member is then bent at the notches 1176 and 1178 so that axially opposite end portions of the tubular member 1160 are disposed in abutting engagement with each other.

The tubular member 1160 is moved into the recess 1162 in the C-shaped holder member 1158. This prevents the tubular member 1160 from springing back from the bent or resiliently deflected condition of FIG. 44 toward its original linear or straight configuration. As the tubular member 1160 is resiliently deflected to form the bend portions 1168 and 1170, the passage 1174 is collapsed and the suture 1154 is firmly gripped at both of the bend portions. This results in the desired tension being maintained in the suture 1154 and in the holder member 1158 being pressed against body tissue with a desired force.

Once the tubular member 1160 has been positioned in the holder member 1158, in the manner illustrated schematically in FIG. 44, both the holder member and tubular member may be plastically deformed by cold flowing the material of the holder member and the tubular member. Alternatively, just the material of the tubular member 1160 may be plastically deformed. The material of the tubular member 1160 and holder member 1158 or just the material of the tubular member 1160 may be deformed by force application members which apply force against opposite sides of the suture retainer 1152 in the manner previously explained in conjunction with the embodiment of the invention illustrated in FIGS. 40–42.

The holder member 1158 is formed of a single piece of biodegradable polymer, such as polycaperlactone. Similarly, the tubular member 1160 is formed of a single piece of a biodegradable polymer. Of course other biodegradable polymers could be utilized if desired.

Figure 46:
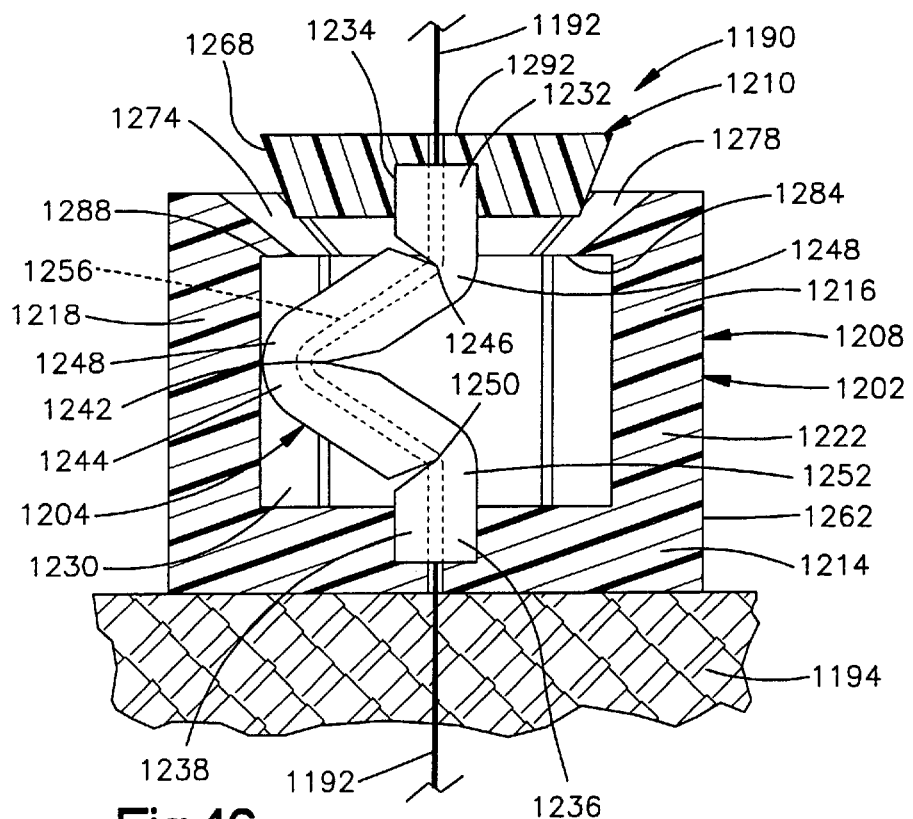
FIG. 46 is a fragmentary sectional view, taken generally along the line 46—46 of FIG. 45, and illustrating the manner in which a tubular member is held between upper and lower portions of a holder as the tubular member is bent by the application of axial force to the tubular member.
Figure 47:
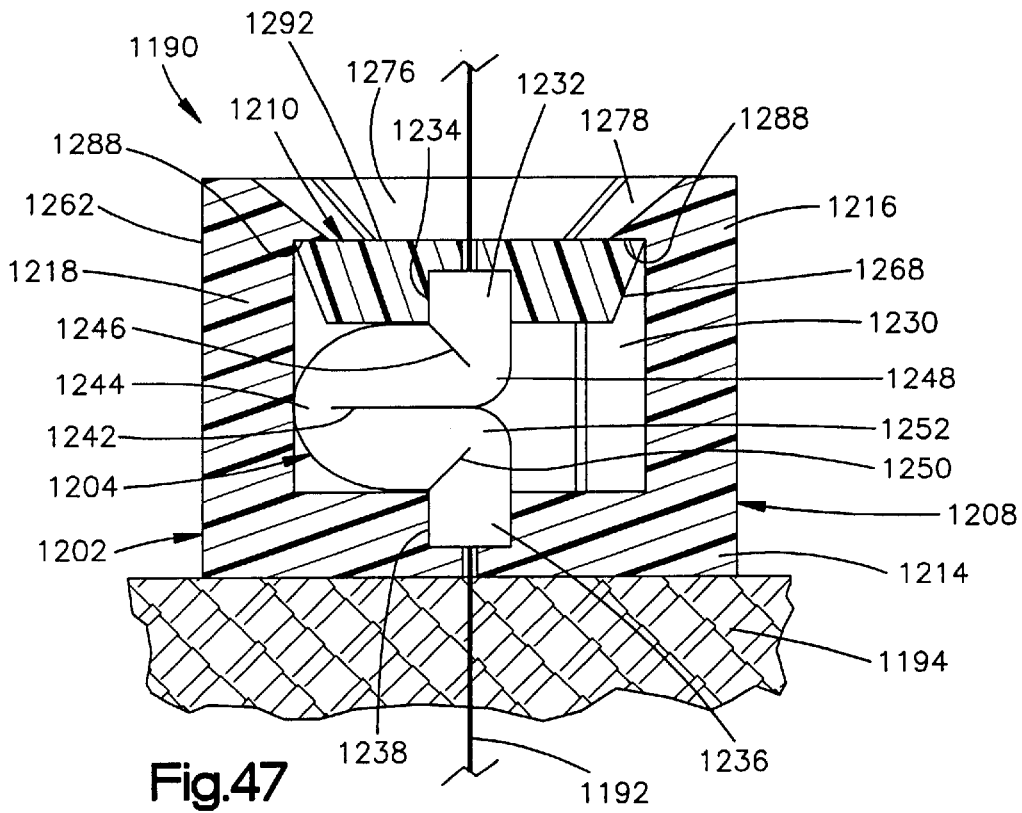
FIG. 47 is a schematic sectional view, generally similar to FIG. 46, illustrating the manner in which one section of the holder is held against movement relative to another section of the holder to retain the tubular member in a bent configuration with the suture extending through the tubular member and holder.

Embodiment of FIGS. 45–47

In the embodiment of the invention illustrated in FIGS. 40–44, a holder member having an open-ended recess is used to retain a resiliently deflected tubular member, through which the suture extends, in a bent configuration. In the embodiment of the invention illustrated in FIGS. 45–47, the holder member has a closed recess in which the resiliently deflected tubular member is received. Since the embodiment of the invention illustrated in FIGS. 45–47 is similar to the embodiment of the invention illustrated in FIGS. 40–44, similar terminology will be utilized to identify similar components. It should be understood that one or more of the features of the embodiments of the invention illustrated in FIGS. 1–44 could be used with the embodiment of the invention illustrated in FIGS. 45–47.

A suture retainer 1190 (FIG. 45) is utilized to position a suture 1192 relative to body tissue 1194. In the illustrated embodiment of the suture retainer 1190, the suture 1192 is connected with a suture anchor 1198 which engages the body tissue 1194. The suture anchor 1198 may be embedded in body tissue, in the manner illustrated in FIG. 42 or may be disposed adjacent to a side of the body tissue opposite from the suture retainer 1190, in the manner illustrated schematically in FIG. 38. The suture anchor 1198 may have any desired construction. Alternatively, the suture anchor 1198 may be omitted and the suture 1192 connected with body tissue in any desired manner. For example, the suture 1192 may be connected with the body tissue in the manner illustrated in FIGS. 1 and 26 if desired. If desired, a suture retainer, having the construction of any one of the suture retainers disclosed herein, could be utilized in place of the suture anchor 1198.

The suture retainer 1190 includes a holder or retainer 1202 and a tubular member 1204 (FIG. 46). The holder 1202 includes a generally cylindrical main or container section 1208 and a circular cover section 1210. It should be understood that the main section 1208 and cover section 1210 could have a different configuration if desired. For example, the main section 1208 and cover section 1210 could have rectangular configurations. Alternatively, either the main section 1208 or the cover section 1210 could have a circular configuration and the other section could have a rectangular configuration.

It is believed that it may be preferred to construct the retainer 1190 with a spherical configuration. If this was done, the cover section 1210 would have an outer side surface which would form a portion of a sphere. The main section 1208 would have an outer side surface which would form the remainder of the sphere, that is the portion of the sphere not defined by the cover section 1210.

The main section 1208 of the holder 1202 includes a circular base 1214 which engages the body tissue 1194 (FIG. 45). A cylindrical wall 1216 extends upward (as viewed in FIGS. 45–47) from the base 1214 and is coaxial with the base. The wall 1216 is formed in a plurality of sections 1218, 1220, 1222 and 1224 (FIG. 45). The sections 1218–1224 of the wall 1216 are resiliently deflectable relative to the base 1214.

The arcuate sections 1218–1224 (FIG. 45) of the wall 1216 cooperate with the base 1214 to form a cylindrical recess or chamber 1230 (FIGS. 46 and 47) in which the cylindrical tubular member 1204 is disposed. The tubular member 1204 has an upper end portion 1232 which is received in a cylindrical socket 1234 formed in the cover section 1210. A cylindrical lower end portion 1236 of the tubular member 1204 is received in a cylindrical socket 1238 formed in the base 1214 of the main section 1208 of the holder 1202. The upper and lower end portions 1232 and 1236 of the tubular member 1204 could be connected with the cover section 1210 and base 1214 in a different manner if desired.

The tubular member 1204 has a construction which is generally similar to the construction of the tubular member 1074 of FIG. 41. However, the tubular member 1204 is provided with a plurality of notches to promote the formation of a plurality of bends in the tubular member. Thus, the tubular member 1204 has a central notch 1242 which facilitates a formation of a bend 1244 (FIG. 46) in a central portion of the initially straight tubular member.

In addition, the tubular member 1204 has an upper (as viewed in FIG. 46) notch 1246 which promotes the formation of a bend 1248 adjacent to the cover section 1210. Similarly, a lower notch 1250 promotes the formation of a bend 1252 adjacent to the base 1214 of the main section 1208 of the holder 1202. The suture 1192 extends through a cylindrical passage 1256 formed in the tubular member 1204.

Although the tubular member 1204 has been illustrated in FIG. 46 in a partially bent configuration, it should be understood that the tubular member 1204 initially has a linear configuration, similar to the linear configuration of the tubular member 1074 of FIG. 41. When force is applied against the cover section 1210, urging the cover section toward the base 1214 of the main section 1208, the bends 1244, 1248 and 1252 begin to form in the tubular member 1204 (FIG. 46). The notches 1242, 1246 and 1250 promote the formation of the bends 1244, 1248 and 1252 at predetermined locations along the length of the tubular member 1204 to impart a zig-zag configuration to the tubular member.

Although it is preferred to utilize notches 1242, 1246 and 1250 to promote the formation of the bends 1244, 1248, and 1252 at predetermined locations along the length of the tubular member 1204, the tubular member could be weakened at preselected locations in other ways if desired. For example, the thickness of the side wall of the tubular member 1204 could be reduced in areas where it is desired to have the bends 1244, 1248 and 1252 formed.

When the suture retainer 1190 is to be utilized to secure the suture 1192 relative to the body tissue 1194, the suture 1192 is moved into a slot 1260 (FIG. 45) in the main section 1208 of the suture retainer 1190. The slot 1260 extends from a cylindrical outer side surface 1262 into a the center of the socket 1238 in the central portion of a base 1214.

The slot 1260 enables the holder 1202 to be moved from a location spaced from the suture 1192 to a location in engagement with the suture and the body tissue 1194 without sliding the holder 1202 along the suture. Thus, the holder 1202 can be moved in a direction transverse to a longitudinal central axis of the suture 1192 into engagement with the suture at a location along the length of the suture immediately adjacent to the body tissue 1194. This facilitates positioning of the holder 1202 relative to the body tissue 1194 without sliding the holder along the suture 1192.

The holder 1202 is pressed against the body tissue with a predetermined force while the suture 1192 is tensioned with a predetermined force. If desired, the slot 1260 could be omitted. If this was done, the suture would extend through a hole in the base 1214.

The tubular member 1204 is then slid along the suture 1192 into engagement with the holder 1202. As this occurs, the tubular member 1204 has a straight or linear configuration, corresponding to the straight configuration of the tubular member 1074 of FIG. 41. The lower end portion 1236 of the tubular member 1204 is moved along the suture 1192 toward the holder 1202 with the suture extending through the passage 1256 in the tubular member 1204. The lower or leading end portion 1236 of the tubular member 1204 is moved through the recess 1230 in the holder 1202 into the socket 1238 in the base 1214 of the holder 1202.

The cover section 1210 is then positioned relative to the suture 1192. A slot 1266 extends from a frustroconical peripheral surface 1268 (FIG. 46) on the cover section 1210 to the center of the socket 1234 in the central portion of the cover section (FIG. 45). The slot 1266 enables the cover section 1210 to be positioned adjacent to the upper or trailing end portion 1232 of the tubular member 1204 without being slid along the suture 1192. Thus, the cover section 1210 can be moved in a direction transverse to the longitudinal central axis of the suture 1192 into engagement with the suture at a location disposed immediately adjacent to and above (as viewed in FIG. 46) the upper end portion 1232 of the tubular member 1204. The cover section 1210 is then moved downward to position the upper end portion 1232 of the tubular member 1204 in the socket 1234.

When the lower end portion 1236 of the tubular member 1204 is initially positioned in the socket 1238 in the holder 1202 and the upper end portion 1232 of the tubular member is initially positioned in the socket 1234 in the cover section 1210, the tubular member 1204 has a straight or linear configuration. This results in the cover section 1210 being disposed above (as viewed in FIG. 46) the holder 1202.

To resiliently deflect the tubular member 1204 from its initial straight configuration and to form the bends 1244, 1248 and 1252 in the tubular member, the cover section 1210 is pushed axially downward toward the holder 1202 while a predetermined tension is maintained in the suture 1192. Columnar loading of the tubular member 1204 increases as the axially downward force applied against the cover section 1210 increases. When a predetermined force has been transmitted from the cover section to the tubular member 1204 and from the tubular member to the holder 1202 and body tissue 1194, the tubular member begins to buckle adjacent to the notch 1242 to initiate formation of the bend 1244.

The continued application of an increasing axial force to the cover section 1210 results in buckling of the tubular member 1204 adjacent to the notches 1246 and 1250 to initiate formation of the bends 1248 and 1252. As the bend 1244 and, subsequently, the bends 1248 and 1252 begin to form, the tubular member 1204 and passage 1256 are deflected to a zig-zag configuration. The cover section 1210 is then moved downward (as viewed in FIG. 46) toward the main section 1208 of the holder 1202. While this is occurring, the holder 1202 is being pressed against the body tissue 1194 with a predetermined force and a predetermined tension is maintained in the suture 1192.

As the tubular member 1204 continues to buckle under columnar loading, the frustroconical peripheral surface 1268 (FIG. 46) on the cover section 1210 moves into engagement with radially inward and downward sloping cam surfaces 1274, 1276, 1278, and 1280 on the sections 1218, 1220, 1222 and 1224 of the wall 1216 (FIG. 45). The force applied against the sections 1218–1224 of the wall 1216 by the surface 1268 of the cover section 1210 resiliently deflects the wall sections 1218–1224 radially outward to increase the size of an opening 1284 to the recess 1230.

As the cover section 1210 continues to move downward, as viewed in FIG. 46, the cover section moves into the recess 1230. As this occurs, the sections 1218–1224 of the wall 1216 resiliently snap back to their initial positions. When the sections 1218–1224 of the wall 1216 have moved back to their initial positions, retainer surfaces 1288 on upper end portions of the sections 1218–1224 of the wall 1216 move into engagement with an upper (as viewed in FIG. 47) side surface 1292 of the cover section 1210 to latch the cover section 1210 in place. This results in the cover section 1210 being held against upward (as viewed in FIG. 47) movement relative to the main section 1208 of the holder 1202. Therefore, the cover section 1210 cooperates with the base 1214 of the main section 1208 of the holder 1202 to retain the tubular member 1204 in the fully bent, zig-zag configuration illustrated in FIG. 47.

As the tubular member 1204 is resiliently deflected from its initial straight configuration through the partially bent configuration of FIG. 46 to the fully bent zig-zag configuration of FIG. 47, the passage 1256 through the tubular member 1204 collapses and grips the suture 1192. The relatively sharp bend 1244 (FIG. 47) in the tubular member 1204 results from pressing the outer side surface on the portion of the tubular member disposed above (as viewed in FIG. 46) the notch 1242 against a portion of the outer side surface of the tubular member disposed below the notch 1242. The relatively sharp bend 1244 results in the suture 1192 being securely gripped by the collapsed portion of the passage 1256 extending through the bend 1244. In addition, the collapsed portions of the passage 1256 through the bends 1248 and 1252 securely grip the suture 1192.

Once the tubular member 1204 has been resiliently deflected to the bent configuration of FIG. 47 and the cover section 1210 firmly latched in place by the sections 1218–1224 of the wall 1216, the suture 1192 is securely gripped to maintain a predetermined tension in the portion of the suture extending between the suture retainer 1190 and the anchor 1198 (FIG. 45). At this time, a predetermined force is transmitted from the holder 1202 to the body tissue 1194. If desired, a force distribution member, similar to the button 602 of FIG. 26, could be positioned between the main section 1208 of the holder 1202 and the body tissue 1194 to distribute the force transmitted from the holder to the body tissue over a relatively large area. Alternatively, the main section 1208 of the holder 1202 could be formed with a circular flange which extends radially outward from the base 1214 to increase the surface area on the body tissue 1194 engaged by the suture retainer 1190.

Although only a single section of the suture 1192 has been illustrated in FIGS. 45–47 as extending through the main section 1208, tubular member 1204, and cover section 1210, two or more sections of the suture could extend through the suture retainer 1190 if desired. For example, two sections of the suture 1192 could extend through the main section 1208, tubular member 1204, and cover section 1210 of the suture retainer 1190 if desired. The two sections of the suture 1192 would extend through the suture retainer 1190 in much the same manner as in which two sections 66 and 68 of the suture 52 extend through the main section 704 of the suture retainer 700 of FIG. 32.

After the tubular member 1204 has been resiliently deflected to the fully bent condition of FIG. 47 and the cover section 1210 latched in place by the sections 1218–1224 of the wall 1216, the suture retainer 1190 may be plastically deformed to further ensure a secure grip on the suture 1192. While the suture retainer 1190 is being pressed against the body tissue 1194 with a predetermined force and while the portion of the suture 1192 disposed between the anchor 1198 (FIG. 45) and the suture retainer 1190 is tensioned with a predetermined force, a pair of force application members, corresponding to the force application members 340 and 342 of FIG. 18, may be pressed against opposite sides of the suture retainer 1190. The force applied against the suture retainer 1190 by the force application members plastically deforms the material of the suture retainer.

The plastic deformation of the suture retainer 1190 is effective to cause cold flowing of material of the suture retainer. Thus, the force application members are effective to apply a predetermined force against the outer side surface 1262 of the suture retainer 1190 to cause flowing of the material of the suture retainer at a temperature below a transition temperature range for the material of the suture retainer. The force applied against the suture retainer 1190 by the force application members is effective to cause cold flowing of the material of both the holder 1202 and the tubular member 1204.

The suture retainer 1190 is plastically deformed by the application of a predetermined force of a predetermined period of time against a suture retainer. As this occurs, the material of the tubular member 1204 cold flows around the suture 1192 and is bonded with the material of the suture. The manner in which the material of the tubular member 1204 bonds with the suture 1192 is the same as is illustrated schematically in FIGS. 4 and 5. The temperature at which the material of the tubular member 1204 is plastically deformed and cold flows under the influence of force applied against the suture retainer 1190 by force application members, is close to the temperature of the body tissue 1194. This temperature is below the transition temperature for the material of the suture retainer 1190.

The suture retainer 1190 may be formed of many different materials. However, it is believed that it will be preferred to form the suture retainer 1190 of a biodegradable polymer. One biodegradable polymer which may be utilized is polycaperlactone. Alternatively, the suture retainer 1190 could be formed of polyethylene oxide terephthalate or polybutylene terephthalate. It is also contemplated that the suture retainer 1190 could be formed of other biodegradable or bioerodible copolymers if desired.

Although it is preferred to form the suture retainer 1190 of a biodegradable material, the suture retainer could be formed of a material which is not biodegradable. For example, the suture retainer 1190 could be formed of an acetyl resin, such as "Delrin" (trademark). Alternatively, the suture retainer 1190 could be formed of a para-dimethylamino-benzenediazo sodium sulfonate, such as "Dexon" (trademark).

It is preferred to effect cold flowing of the material of the suture retainer 1190 without the addition of heat. However, it is contemplated that the suture retainer 1190 could be heated to a temperature which is somewhat above the temperature of the body tissue 1194. If desired, heat could be transmitted to the suture retainer through the force application members utilized to effect cold flowing of the material of the suture retainer 1190. Although the suture retainer 1190 may be heated, the suture retainer would be maintained at a temperature below the transition temperature for the material of the suture retainer. Alternatively, the suture retainer could be heated to a temperature in the transition temperature range for the suture retainer.

The suture 1192, like the sutures 1076, 1134 and 1154 of FIGS. 40–44, may be of natural or synthetic materials. The sutures of FIGS. 41–47 may be monofilament or may be formed of a plurality of interconnected filaments. The sutures of FIGS. 41–47 may be biodegradable or non-biodegradable. It may be preferred to form the sutures of FIGS. 41–45 of the same material as the associated suture retainers. However, the sutures could be formed of a material which is different than the materials of the associated suture retainers.

In the embodiment of the invention illustrated in FIGS. 45, 46 and 47, the holder 1202 is formed separately from the tubular member 1204. Thus, the main section 1208 and cover section 1210 of the holder 1202 are formed separately from the tubular member 1204. However, it is contemplated that the tubular member 1204 and the cover section 1210 and main section 1208 of the holder 1202 could be formed as one piece. Alternatively, the tubular member 1204 could be formed as one piece with just the cover section 1210 or just the main section 1208 of the holder 1202. If the cover section 1210 and main section 1208 of the holder 1202 are integrally formed as one piece with the tubular member 1204, the passage 1256 through the tubular member 1204 would extend through the cover section 1210 and main section 1208 of the holder 1202. This would result in the holder 1202 and tubular member 1204 being moved together along the suture 1192 toward the body tissue 1194.

When the cover section 1210 and main section 1208 of the holder 1202 are integrally formed as one piece with the tubular member 1204, it may be desired to form a slot which extends through the holder 1202 and tubular member 1204 to a central axis of the tubular member. This would enable the suture retainer to be moved into engagement with the suture 1192 without first threading or inserting the suture through a passage extending through both the holder 1202 and tubular member 1204. The slot in the integrally formed tubular member 1204 and holder 1202 would enable the suture retainer 1190 to be positioned in engagement with the suture 1192 by moving the suture retainer transverse to a longitudinal central axis of the suture 1192. As this occurs, the suture would move through the aligned slots in the holder 1202 and tubular member 1204 to a position in which the longitudinal central axis of the suture 1192 is coincident with the longitudinal central axis of the tubular member 1204. When such a slot is utilized, it is believed that the cold flowing of the material of the suture retainer 1190 by the application of force to the suture retainer while pressing the holder 1202 against the body tissue 1194 with a predetermined force and maintaining a predetermined tension in the portion of the suture 1192 disposed between the suture retainer and the anchor 1198 may be particularly advantageous.

In the embodiment of the invention illustrated in FIGS. 45–47, the wall 1216 is formed by a circular array of wall sections 1218–1224. It is contemplated that a number of wall sections greater than the illustrated number or less than the illustrated number could be utilized if desired. It is also contemplated that the size of the slots between the wall sections 1218–1224 could be increased. If desired, one or more of the wall sections 1218–1224 could be omitted. For example, the diametrically opposite wall sections 1220 and 1222 could be eliminated. This would open up the recess 1230 and facilitate movement of body tissue into the recess.

Embodiment of FIGS. 48–52

In the embodiment of the invention illustrated in FIGS. 40–47, the suture retainers 1070, 1152, and 1190 all utilize a tubular member which partially encloses the suture. In the embodiment of the invention illustrated in FIGS. 48–52, one portion of a suture retainer is resiliently deflected and presses the suture against another portion of the suture retainer. Since the embodiment of the invention illustrated in FIGS. 48–52 is similar to the embodiment of the invention illustrated in FIGS. 40–47, similar terminology will be utilized to identify similar components. It should be understood that one or more of the features of any one of the embodiments of invention illustrated in FIGS. 1–47 may be used with any of the other embodiments of the invention illustrated in FIGS. 48–52.

A suture retainer 1300 (FIG. 52) is utilized to secure a suture 1302 against movement relative to body tissue. It should be understood that although body tissue has not been illustrated schematically in FIG. 52, a predetermined force is transmitted from the suture retainer 1300 to the body tissue. In addition, a predetermined tension is maintained in a portion of the suture 1302 extending between the suture retainer 1300 and an anchor corresponding to the anchor 1082 of FIG. 42. However, it should be understood that the suture 1302 could be connected with body tissue in a manner other than the use of a suture anchor. For example, the suture 1302 could be connected with body tissue in the manner illustrated schematically in FIGS. 1, 9, 26, 36, 38, and/or 39 herein.

The suture retainer 1300 includes a holder member 1306 (FIGS. 48 and 49) and a resilient member 1308 (FIGS. 50 and 51). The suture 1302 is wrapped around the resilient member 1308 (FIGS. 50 and 51). As the suture 1302 is wrapped around the resilient member 1308, a plurality of bends are formed in the suture. As turns of the suture are wrapped around the resilient member 1308, loops are formed in the suture 1302 around the resilient member 1308 in the manner illustrated in FIG. 50. A greater or lesser number of loops could be provided in the suture 1302 if desired.

In the embodiment of the invention illustrated in FIGS. 48–52, only a single section of the suture 1302 is wrapped around the resilient member 1308 (FIGS. 50 and 51). However, a plurality of sections of the suture 1302 could be wrapped around the resilient member 1308 if desired. For example, two sections of the suture 1302 could be wrapped around the resilient member 1308 in much the same manner as in which two sections 66 and 68 of the suture 52 are wrapped around the suture retainer 50 in FIG. 1.

The resilient member 1308 has a generally C-shaped configuration. The resilient member has an opening 1310 to a generally circular recess 1312. A pair of actuator members 1316 and 1318 (FIGS. 50 and 51) are disposed adjacent to opposite sides of the opening 1310. By manually applying force against the actuator members 1316 and 1318, the resilient member 1308 can be deflected to decrease the size of the opening and the diameter of the generally circular resilient member 1308.

The resilient member 1308 includes a generally rectangular body section 1322 and an arcuate rim section 1324 which projects radially outward from the body section 1322. The actuator members 1316 and 1318, body section 1322 and rim section 1324 of the resilient member 1308 are integrally molded as one piece.

The holder member 1306 (FIGS. 48 and 49) has an annular body section 1328 which defines a circular central opening 1330. The annular body section 1328 has an arcuate radially inner side surface 1334 (FIG. 49) which faces inwardly toward the center of the holder member 1308 and defines an annular groove 1336. The illustrated body section 1328 has a generally rectangular cross sectional configuration, as viewed in FIG. 49. However, it is contemplated that the body section could be formed with a generally parabolic cross sectional configuration, as viewed in FIG. 49, in order to minimize interference with adjacent body tissues. In fact, the body section 1328 could be formed with a circular cross sectional configuration, as viewed in FIG. 49.

When the resilient member 1308 is in its initial or undeflected condition, the body section 1322 of the resilient member has an outside diameter which is greater than the diameter of the circular opening 1330 formed in the holder member 1306. In addition, the rim section 1324 has a maximum outside diameter which is greater than the diameter of the groove 1336 in the holder member.

Once the suture 1302 has been wrapped around the resilient member 1308, in the manner illustrated schematically in FIGS. 50 and 51, the actuator members 1316 and 1318 are moved together to close the opening 1310. As the actuator members 1316 and 1318 move toward each other, the resilient member 1308 is resiliently deflected.

The resilient deflection of the member 1308 decreases the outside diameter of the rim section 1324 to a diameter which is slightly less than the diameter of the opening 1330 (FIG. 48) in the body section 1328 of the holder member 1306. The resilient member 1308 is then moved into axial alignment with the holder member 1306. When the resilient member 1308 and holder member 1306 are in a coaxial relationship, the resilient member 1308 is moved into the opening 1330 in the holder member 1306. As the resilient member 1308 is moved into the opening 1330 in the holder member 1306, the actuator members 1316 and 1318 are held in abutting engagement with each other to close the opening 1310 (FIG. 50) and maintain the resilient member 1308 in a resiliently deflected condition in which the member has an outside diameter which is slightly less than the diameter of the opening 1330.

When the resilient member 1308 has been moved into the opening 1330 in the body section 1328, the rim section 1324 of the resilient member 1308 is aligned with the groove 1336 (FIG. 49) in the holder member 1308. The actuator members 1316 and 1318 are then released. This results in expansion of the resilient member 1308 back toward the free or unrestrained condition of FIG. 50. However, the groove 1336 has a diameter which is less than the diameter of the unrestrained rim section 1324 (FIG. 50). Therefore, the rim section 1324 presses against the inner side surface 1334 of the groove 1336 to hold the resilient member 1308 in a deflected condition.

As was previously mentioned, the suture 1302 is wrapped around the resilient member 1308 (FIG. 50). Therefore, when the resilient member 1308 expands into the groove 1336 in the holder member 1306, the rim section 1324 on the resilient member is effective to clamp the turns formed in the suture 1302 against the inner side surface 1334 of the holder member 1306. This clamping action results in the suture 1302 being firmly gripped between the outer side surface of the rim section 1324 and the inner side surface 1334 of the groove 1336. The clamping action between the resilient member 1308 and the holder member 1306 secures the suture against movement relative to the suture retainer 1300, body tissue against which the suture retainer 1300 is pressed, and an anchor with which the suture 1302 is connected.

In the embodiment of the invention illustrated in FIGS. 48–52, the suture 1302 is wrapped for a plurality of turns around a resilient member 1308. If desired, the suture 1302 could be wrapped for a single turn around the resilient member 1308. Of course, a greater number of turns of the suture 1302 could be provided around the resilient member 1308 if desired.

When the suture retainer 1300 is to be positioned relative to body tissue, it is contemplated that the holder member 1306 will be moved along the suture 1302 into engagement with the body tissue. The suture 1302 will then be wrapped around the resilient member 1308. The resilient member 1308 will then be moved along the suture 1302 toward the holder member 1306. As the resilient member 1308 is slid along the suture 1302 toward the holder member 1306, the turns of the suture around the resilient member will slide along the surface of the resilient member. This results in movement of the bends formed in the suture 1302 by wrapping the suture around the resilient member 1308 moving along the suture toward the body tissue and holder member 1306 with the resilient member 1308.

It is contemplated that the holder member 1306 will be pressed against the body tissue with a predetermined force and that a predetermined tension will be provided in the suture 1302 as the resilient member 1308 is moved into the opening 1330 in the holder member 1306. The predetermined tension will be maintained in the suture 1302 and the holder member 1306 will be pressed against the body tissue with the predetermined forces as the rim section 1324 on the resilient member 1308 is moved into alignment with the groove 1336 in the holder member 1306. The predetermined tension in the suture 1302 and the predetermined force to be transmitted between the holder member 1306 and the body tissue as the actuator members 1316 and 1318 are released enable the resilient member 1308 to radially expand and clamp the suture 1302 against the side surface 1334 of the groove 1336.

In the embodiment of the invention illustrated in FIGS. 48–52, the holder member 1306 is formed as a continuous annular ring. Therefore, the ring must be moved along the suture 1302 to position the ring relative to the body tissue. It is contemplated that a radial slot could be provided through the annular holder member 1306. The radial slot in the holder member 1306 enables the holder member to be positioned adjacent to the body tissue and then moved transversely to the suture 1302 to position the suture in the opening 1330 in the holder member 1306. Thus, the slot in the holder member 1306 would allow the holder member to be positioned relative to body tissue in much the same manner as in which the slot 1260 (FIGS. 46 and 47) enables the main section 1208 of the holder 1202 to be positioned relative to body tissue.

In the embodiment of the invention illustrated in FIGS. 48–52, a single rim section 1324 is provided on the body section 1322 of the resilient member 1308 (FIGS. 50 and 51). However, it is contemplated that a plurality of axially spaced apart circular rim sections having the same configuration as the rim section 1324 could be formed on the body section 1322. Of course, if a plurality of rim sections 1324 were provided on the resilient member 1308, a plurality of grooves 1336 would be formed in the body section 1328 of the holder member 1306 (FIGS. 48 and 49). By providing a plurality of rim sections on the resilient member 1308 and a plurality of grooves in the holder member 1306, undulations would be formed in each of the turns of the suture 1302 around the resilient member 1308. A clamping action would be provided between each of the rim sections 1324 on the resilient member 1308 and each of the grooves 1336 in the holder member 1306.

After the resilient member 1308 has been positioned in the opening 1330 in the holder member 1306 (FIG. 52) and while a predetermined tension is maintained in the portion of the suture 1302 between the suture retainer 1300 and an anchor in the body tissue and while a predetermined force is transmitted between the holder member 1306 and the body tissue, the suture retainer 1300 is plastically deformed to increase the grip of the suture retainer on the suture 1302. Thus, while the suture retainer is being pressed against the body tissue with the predetermined force and a predetermined tension is maintained in the portion of the suture between the suture retainer and an anchor in the body tissue, a pair of force application members are pressed against opposite sides of the suture retainer 1300. The force applied against the suture retainer 1300 by the force application members is effective to plastically deform the material of the suture retainer.

The plastic deformation of the suture retainer 1300 is effective to cause cold flowing of material of the holder member 1306 and resilient member 1308. Force is applied against the suture retainer 1300 by the force application members while the suture retainer is at a temperature below a transition temperature range for the material of the suture retainer. Thus, the suture retainer 1300 is plastically deformed while the suture retainer is at a temperature close to the temperature of the associated body tissue. This temperature is below the transition temperature for the material of the suture retainer 1300.

It is contemplated that axially directed forces may be applied against axially opposite ends of the suture retainer 1300 to effect the plastic deformation and cold flowing of the material of the suture retainer. However, it is also contemplated that radially directed forces could be applied against the suture retainer 1300 to effect plastic deformation and cold flowing of the material of the suture retainer.

If force is applied against axially opposite end portions of the suture retainer 1300 to effect the cold flowing of the material of the suture retainer, it is contemplated that force application members similar to those illustrated in FIG. 3 herein could be utilized. Alternatively, if radially directed force is to be applied against the suture retainer 1300 to effect a cold flowing of the material of the suture retainer, force application members similar to those illustrated in FIG. 18 herein could be utilized.

The suture retainer 1300 may be formed of a many different materials. However, it is believed that it will be preferred to form the suture retainer 1300 of a biodegradable polymer. One biodegradable polymer which may be utilized is polycaperlactone. Alternatively, the suture retainer 1300 could be formed of polyethylene oxide terephthalate or polybutylene terephthalate. It is also contemplated that other biodegradable or bioerodible copolymers could be utilized if desired.

Although it is preferred to form the suture retainer 1300 of a biodegradable material, the suture retainer could be formed of a material which is not biodegradable. For example, the suture retainer could be formed of an acetyl resin, such as "Delrin" (trademark). Alternatively, the suture retainer 1300 could be formed of a para-dimethylamino-benzenediazo sodium sulfonate, such as "Dexon" (trademark).

It is preferred to effect cold flowing of the material of the suture retainer 1300 without the addition of heat. However, it is contemplated that the suture retainer 1300 could be heated to a temperature which is somewhat above the temperature of the body tissue. If desired, heat could be transmitted to the suture retainer through the force application members. Although the suture retainer 1300 may be heated, the suture retainer would be maintained at a temperature below the transition temperature for the material of the suture retainer. Alternatively, the suture retainer 1300 could be heated into its transition temperature range and plastically deformed by hot flowing of the material of the suture retainer rather than cold flowing of the material.

In the various embodiments of the invention illustrated herein, the suture, such as the suture 1302 of FIG. 52, is formed of a monofilament which is biodegradable. However, it is contemplated that the sutures of any one of the embodiments of the invention illustrated herein, such as the suture 1302, could be formed of a plurality of interconnected filaments. These interconnected filaments could be either biodegradable or non-biodegradable. It may be preferred to form the suture of any one of the embodiments of the invention illustrated herein of the same material as the associated suture retainer. Thus, the suture 1302 of FIG. 52 could be formed of the same material as the suture retainer 1300. However, the suture 1302 could be formed of a material which is different than the material of which the suture retainer 1300 is formed.

Figure 53:
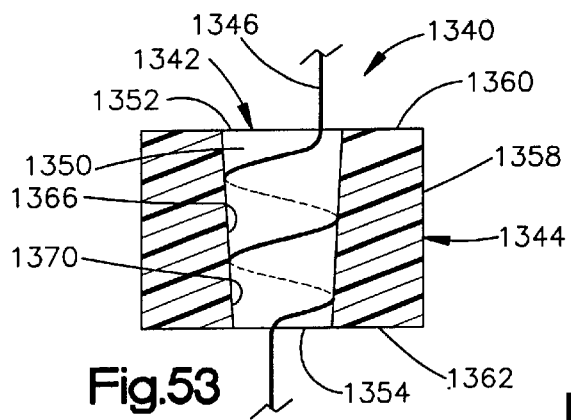
FIG. 53 is a sectional view illustrating another embodiment of the retainer in which an axially tapered member cooperates with an axially tapered recess in a holder to grip a suture.

Embodiment of FIG. 53

In the embodiment of the invention illustrated in FIGS. 48–52, the suture 1302 is wrapped around a resilient member 1308. In the embodiment of the invention illustrated in FIG. 53, the suture is wrapped around an axially tapered member and is-enclosed by a holder member. Since the embodiment of the invention illustrated in FIG. 53 is generally similar to the embodiment of the invention illustrated in FIGS. 1–52, similar terminology will be utilized to identify similar components. It should be understood that one or more of the features of the embodiments of the invention illustrated in FIGS. 1–52 could be used with the embodiment of the invention illustrated in FIG. 53.

A suture retainer 1340 (FIG. 53) includes an axially tapered member 1342 and a holder member 1344 which encloses the axially tapered member 1342 and a portion of a suture 1346. The suture 1346 is connected with a suture anchor (not shown) embedded in body tissue. The suture retainer 1340 is effective to transmit a predetermined force to the body tissue. A predetermined tension is maintained in the portion of the suture 1346 disposed between the suture retainer 1340 and the suture anchor.

Although the suture 1346 has been described as being connected with a suture anchor embedded in body tissue, it is contemplated that the suture 1346 could be connected with body tissue in a different manner if desired. For example, the suture 1346 could be connected with body tissue in the manner illustrated in FIGS. 1, 9, 26, 36, 38, or 39 herein. Alternatively, the suture 1346 could be connected with a second suture retainer which may have the same construction as the suture retainer 1340, the construction of any one of the suture retainers disclosed herein, or the construction of other known suture retainers.

The axially tapered member 1342 has an outer side surface 1350 which is formed as a portion of a right circular cone. The outer side surface 1350 of the axially tapered member 1342 extends between flat parallel circular end surfaces 1352 and 1354. The end surfaces 1352 and 1354 are disposed in a coaxial relationship with each other and with the outer side surface 1350 of the axially tapered member 1342. The end surface 1354 of the conical tapered member 1342 has a diameter which is smaller than the diameter of the end surface 1352 of the tapered member 1342.

The holder member 1344 has a cylindrical outer side surface 1358. The outer side surface 1358 extends between a flat end surface 1360 and a circular end surface 1362. The end surfaces 1360 and 1362 extend parallel to each other and are disposed in a coaxial relationship. The holder member 1344 may have a configuration other than the cylindrical configuration illustrated in FIG. 53. For example, the holder member 1344 may have a spherical configuration.

A recess 1366 is formed in the cylindrical holder member 1344. The recess 1366 is of the same size and configuration as the axially tapered member 1342. The recess 1366 is formed as a portion of a right circular cone. The recess 1366 has an axially tapered inner side surface 1370 which has the same angle of taper as the outer side surface 1350 of the tapered member 1342. If desired, the taper of the side surface 1370 of the recess 1366 could be slightly less than the taper in the outer side surface 1350 on the axially tapered member 1342 to promote a wedging action between the axially tapered member and the holder member 1344.

In the embodiment of the invention illustrated in FIG. 53, the taper on the outer side surface 1350 of the axially tapered member 1342 and the taper on the inner side surface 1370 of the recess 1366 in the holder member 1344 is the same. The tapers on the axially tapered member 1342 and the recess 1366 are relatively small and provide a self-holding action. Although many different tapers could be utilized, it is contemplated that it may be preferred to use a taper of the Morse taper series. Of course, other known tapers could be utilized if desired.

The suture 1346 is wrapped around the axially tapered member 1342 before the axially tapered member is inserted into the holder member 1344. As the suture 1346 is wrapped around the axially tapered member 1342, a plurality of loops are formed in a spiral. This results in a continuous series of smooth arcuate bends, which are free of stress inducing discontinuities, being formed in the suture 1346 as it is wrapped around the axially tapered member 1342. After the suture 1346 has been wrapped around the axially tapered member 1342, the axially tapered member is inserted into the recess 1366 in the holder member 1344. If desired, a spiral groove may be formed in the outer side surface 1350 of the axially tapered member 1342 to facilitate wrapping the suture 1346 around the axially tapered member 1342.

A predetermined force is transmitted between the holder member 1344 and the body tissue as the axially tapered member 1342 is moved into the recess 1346 in the holder member. In addition, a predetermined tension is maintained in the portion of the suture 1346 extending between the suture retainer 1340 and a suture anchor embedded in the body tissue.

The axially tapered member 1342 and the holder member 1344 may be formed of a biodegradable or a bioerodible copolymer. Although it is believed that it will be preferred to use a biodegradable copolymer to form the axially tapered member 1342 and holder member 1344, the axially tapered member and holder member could be formed of materials which are not biodegradable. The suture 1346 is formed as a continuous filament of biodegradable material. However, the suture 1346 could be formed as a plurality of strands.

In the embodiment of the invention illustrated in FIG. 53, only a single section of the suture 1346 is wrapped around the axially tapered member 1342. However, a plurality of sections of the suture 1346 could be wrapped around the axially tapered member 1342 if desired. For example, two sections of the suture 1346 could be wrapped around the axially tapered member 1342 in the same direction, in much the same manner as in which two sections 66 and 68 of the suture 52 are wrapped in the same direction around the body 184 of the suture retainer 190 of FIG. 9. Alternatively, two sections of the suture 1346 could be wrapped around the axially tapered member 1342 in opposite directions, in much the same manner as in which two sections 66 and 68 of the suture 52 are wrapped in opposite directions around the conical body 242 of the suture retainer 244 of FIG. 13. If desired, grooves, corresponding to the groove 194 of FIG. 9 or the grooves 258 and 260 of FIG. 13, could be provided in the axially tapered member 1342 (FIG. 53).

Figure 54:
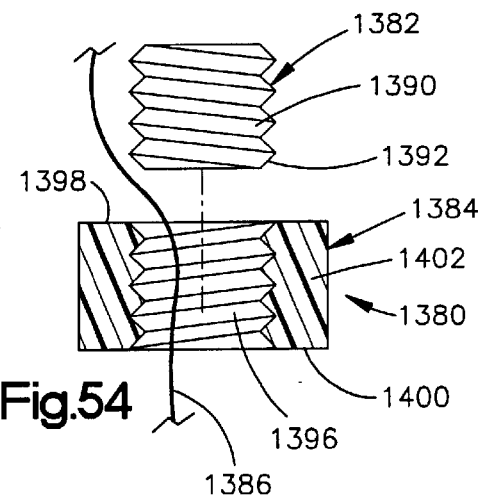
FIG. 54 is a schematic illustration of another embodiment of the retainer in which internally and externally threaded members cooperate to grip a suture.

Embodiment of FIG. 54

In the embodiment of the invention illustrated in FIG. 54, a suture retainer 1380 is formed by an externally threaded member 1382 and an internally threaded holder member 1384. The externally threaded member 1382 and the holder member 1384 cooperate to secure a suture 1386 against movement relative to body tissue. It should be understood that one or more of the features of the embodiments of the invention illustrated in FIGS. 1–53 could be used with the embodiment of the invention illustrated in FIG. 54.

The externally threaded member 1382 has a helical external thread convolution 1390 which extends from a leading end portion 1392 of the externally threaded member 1382 to a trailing or head end portion (not shown) of the externally threaded member 1382. If desired, a force transmission element, such as a manually engagable handle or a hexagonal head engagable by a suitable tool, may be provided on the trailing end portion of the externally threaded member 1382. If a manually engagable handle is provided, the handle could project outwardly of the external thread convolution 1390 and have suitably knurled surfaces for manual engagement by a surgeon. Alternatively, the externally threaded member 1382 could have the configuration of any one or many known bolts.

The holder member 1384 has an internal thread convolution 1396 which extends between flat annular end surfaces 1398 and 1400 on a cylindrical body section 1402 of the holder member 1384. Although the external thread convolution 1390 and internal thread convolution 1396 have been schematically illustrated in FIG. 54 as having sharply defined crests and roots, the thread convolutions 1390 and 1396 could have rounded crests and roots, similar to those found on Whitworth screw threads or British Association screw threads. It is contemplated that the roots and crests of the internal and external thread convolutions 1396 and 1390 could have rounded or continuously curving surface areas which define the entire thread convolutions or at least a major portion of the thread convolutions.

The suture 1386 may have a distal end portion connected with a suture anchor embedded in body tissue, in the same manner as in which the suture 1192 of FIG. 45 is connected with the suture anchor 1198 embedded in the body tissue 1194. However, the suture 1386 (FIG. 54) could be connected with body tissue in a different manner if desired. For example, the suture 1386 could be connected with body tissue in any one of the ways illustrated in FIGS. 1, 9, 26, 36, and 38 herein. Of course, the suture 1386 could be connected with body tissue in a different manner if desired.

When the suture retainer 1380 is to be utilized to secure the suture 1386 relative to body tissue, one or more sections of the suture are inserted through the internally threaded opening in the holder member 1384. The holder member 1384 is then moved along the suture until the end surface 1400 on the holder member is disposed in abutting engagement with the body tissue. The suture 1386 is then tensioned with a predetermined force and the end surface 1400 on the holder member 1384 is pressed against the body tissue with a predetermined force.

The externally threaded member 1382 is then moved into engagement with the holder member 1384. As the external thread convolution 1390 engages the internal thread convolution 1396, the externally threaded member 1382 is rotated about its central axis relative to the holder member 1384. The interaction between the external thread convolution 1390 and internal thread convolution 1396 causes the externally threaded member 1382 to move into the holder member 1384. As this occurs, the suture 1386 is clamped between the external thread convolution 1390 and internal thread convolution 1396.

The trailing end portion (not shown) of the externally threaded member 1382 is provided with a head end surface which projects radially outward from the external thread convolution 1390. The head end surface moves into engagement with the end surface 1398 on the holder member 1384. When the head end surface on the trailing end portion of the externally threaded member 1382 has moved into abutting engagement with the end surface 1398 on the holder member 1384, the helical, axially upward (as viewed in FIG. 54) facing flank on the external thread convolution 1390 is pressed firmly against the axially downward facing flank on the internal thread convolution 1396. The helical upward facing flank of the external thread convolution 1390 and the helical downward facing flank of the internal thread convolution 1396 securely grip the suture 1386 with a clamping action at spaced apart locations along the length of the suture 1386. The head end surface may be disposed on a hexagonal head end portion of the externally threaded member 1382.

If desired, space can be provided between the helical crest of the external thread convolution 1390 and the helical root of the internal thread convolution 1396. Space can also be provided between the root of the external thread convolution 1390 and the crest of the internal thread convolution 1396. This space would minimize any possibility of abrading the suture 1386. If this is done, the suture 1386 would be gripped by force transmitted between the helical flanks of the external thread convolution 1390 and internal thread convolution 1396. Of course, rounding the crests and roots of the internal and external thread convolutions 1396 and 1390 would also minimize any possibility of abrading the suture 1386.

In the embodiment of the invention illustrated in FIG. 54, only a single section of the suture 1386 extends through holder member 1384. However, a plurality of sections of the suture 1386 could extend through the holder member 1384 if desired. For example, two sections of the suture 1386 could extend through the holder member 1384 in much the same manner as in which two sections 66 and 68 of the suture 52 extend through the suture retainer 740 of FIG. 34. If desired, a force distribution member having a plurality of openings, that is, one for each section of the suture, could be provided between the holder member 1384 and body tissue. The force distribution member may have a construction similar to the construction of the force distribution member 910 of FIG. 36.

It is contemplated that the externally threaded member 1382 (FIG. 54) and holder member 1384 will be formed of a biodegradable or bioerodible polymer. However, the externally threaded member 1382 and internally threaded member 1384 could be formed of materials which are not biodegradable.

The suture 1386 is formed of a biodegradable material. The suture 1386 may be formed as a monofilament or a plurality of interconnected filaments. Although it is believed that it will be preferred to form the suture 1386 of a material which is biodegradable, the suture 1386 could be formed of a material which is not biodegradable.

Once the externally threaded member 1382 and holder member 1384 have been interconnected in the manner previously described, it is contemplated that the material of the suture retainer 1380 may be plastically deformed to enhance the grip of the suture retainer on the suture 1386. Thus, while the suture retainer 1380 is being pressed against the body tissue with a predetermined force and while a predetermined tension is maintained in the portion of the suture 1386 disposed between the suture retainer 1380 and an anchor embedded in body tissue, a pair of force application members are pressed against opposite sides of the suture retainer in the manner indicated schematically in FIG. 34. The force applied against the suture retainer 1380 by the force application members plastically deforms the material of the suture retainer.

The plastic deformation of the suture retainer 1380 FIG. 54) is effective to cause cold flowing of the material of the suture retainer. The force applied against the suture retainer by the force application members will, in all probability, be effective to cause a greater cold flowing of the material of the holder member 1384 than of the externally threaded member 1382. The cold flowing of the material of the holder member 1384 will result in a bonding of the material of the holder member and, to some extent at least, of the externally threaded member 1382 with the suture 1386 in the manner indicated schematically in FIG. 4.

It is preferred to effect the cold flowing of the material of the suture retainer 1380 without the addition of heat. However, it is contemplated that the suture retainer 1380 could be heated to a temperature which is somewhat above the temperature of the body tissue. If desired, heat could be transmitted to the suture retainer through the force application members. Although the suture retainer 1380 may be heated, the suture retainer would be maintained at a temperature below the transition temperature of the material of the suture retainer.

Under certain circumstances, it is believed that it may be desired to heat the suture retainer 1380 into the transition temperature range of the material forming the externally threaded member 1382 and the holder member 1384. When this is done, the force application members will effect a hot flowing of the material of the suture retainer rather than a cold flowing of the material.

In the embodiment of the invention illustrated in FIG. 54, a single section of the suture 1386 extends through the internally threaded opening in the body section 1402 of the holder member 1384. However, it is contemplated that one or more sections of the suture 1386 could be wrapped around the body section 1402 of the holder member 1384, in much the same manner as in which the sections 66 and 68 of the suture 52 are wrapped around the suture retainer 50 in FIG. 2. This would result in a plurality of sections of the suture 1386 extending through the internally threaded opening in the body section 1402 of the holder member 1384.

Figure 55:
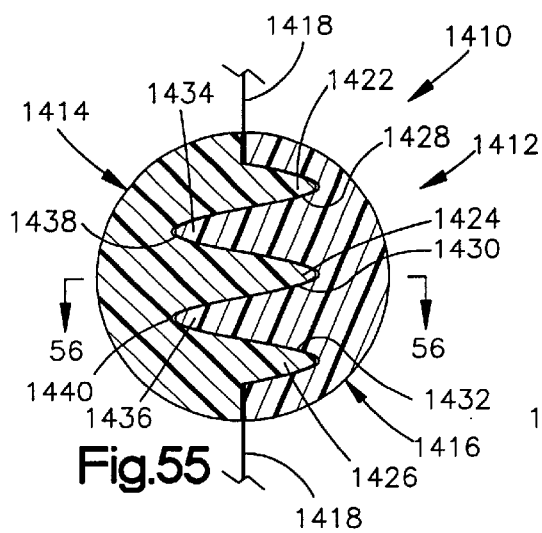
FIG. 55 is a schematic sectional view of another embodiment of the retainer in which fingers and recesses on a pair of members cooperate to grip a suture.
Figure 56:
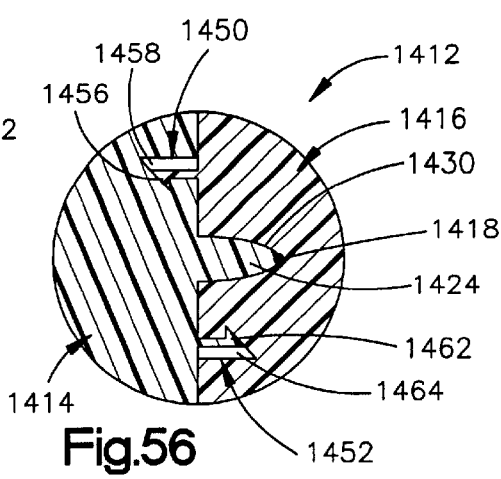
FIG. 56 is a sectional view taken generally along the line 56—56 of FIG. 55, illustrating the manner in which a finger of one of the members cooperates to the recess on the other member to grip a suture.

Embodiment of FIGS. 55 and 56

In the embodiment of the invention illustrated in FIGS. 40–47, a tubular member 1074, 1130 or 1204 is deflected to form bends in a suture and grip the suture. In the embodiment of the invention illustrated in FIGS. 55 and 56, the bends are formed in the suture by interdigitating extensions or fingers. Since the embodiment of the invention illustrated in FIGS. 55 and 56 is similar to the embodiments of the invention illustrated in FIGS. 1–54, similar terminology will be utilized to identify similar components. It should be understood that one or more features of the embodiments of the invention illustrated in FIGS. 1–54 may be used with the embodiment of the invention illustrated in FIGS. 55 and 56.

A suture retainer 1410 includes a holder member 1412. The holder member 1412 has a spherical configuration. The holder member 1412 includes left and right (as viewed in FIG. 55) sections 1414 and 1416. The sections 1414 and 1416 have a generally hemispherical configuration. The sections 1414 and 1416 are disposed on opposite sides of a suture 1418. If desired, the suture retainer 1410 could have a configuration which is different than the illustrated spherical configuration. For example, the suture retainer 1410 could be provided with a flat side surface which is pressed against body tissue.

The suture 1418 is connected with an anchor (not shown) which is embedded in body tissue. Of course, as previously explained herein, the suture 1418 could be connected with body tissue in a different manner if desired. A predetermined tension is maintained in a portion of the suture 1418 disposed between the suture retainer 1410 and the anchor. In addition, a predetermined force is transmitted from the suture retainer to the body tissue.

The suture 1418 may have a distal end portion connected with a suture anchor embedded in body tissue, in the same manner as in which the suture 1192 of FIG. 45 is connected with the suture anchor 1198 embedded in the body tissue 1194. However, the suture 1418 (FIG. 55) could be connected with body tissue in a different manner if desired. For example, the suture 1418 could be connected with body tissue in any one of the ways illustrated in FIGS. 1, 9, 26, 36, and 38 herein. Of course, the suture 1418 could be connected with body tissue in a different manner if desired.

The section 1414 of the holder member 1412 is provided with a plurality of generally cylindrical fingers or projections 1422, 1424, and 1426 which extend into generally cylindrical recesses 1428, 1430 and 1432 formed in the section 1416 of the holder member 1412. Similarly, a plurality of generally cylindrical fingers or projections 1434 and 1436 extend from the section 1416 of the holder member 1412 into generally cylindrical recesses 1438 and 1440 formed in the section 1414 of the holder member 1412. It is contemplated that the number and configuration of the projections from the sections 1414 and 1416 could be different than the specific number and configuration of projections illustrated in FIG. 55.

The projections 1434 and 1436 from the section 1416 are interdigitated with or extend between the projections 1422, 1424 and 1426 from the section 1414. The suture 1418 is coextensive with the outer side surfaces of the projections 1422, 1424, 1426, 1434 and 1436. This results in the portion of the suture 1418 disposed in the suture retainer 1410 having a serpentine configuration. The serpentine configuration of the suture 1418 results in the formation of a plurality of bends where the suture extends across outer end portions of the fingers or projections 1422, 1424, 1426, 1434 and 1436.

The portion of the suture 1418 disposed in the suture retainer 1410 is firmly gripped between the fingers or projections and the side surfaces of the recesses in which the projections are disposed. Thus, a portion of the suture 1418 is firmly gripped between the projections 1424 and 1426 from the section 1414 of the holder member 1412 and the side surfaces of the recesses 1428, 1430 and 1432 in the section 1416 of the holder member 1412. Similarly, a portion of the suture is firmly gripped between the projections 1434 and 1436 from the section 1416 and the side surfaces of the recesses 1438 and 1440 formed in the section 1414 of the holder member 1412.

A pair of connectors 1450 and 1452 (FIG. 56) are provided to interconnect the sections 1414 and 1416 of the holder member 1412. The connector 1450 includes a latch member 1456 which extends from the section 1416 into a recess 1458 formed in the section 1414. The latch member 1456 has a shoulder which abuts a surface of the recess 1458 to hold the section 1414 against movement relative to the section 1416.

Similarly, the connector 1452 includes a latch member 1462 which extends from the section 1414 into a recess 1464 formed in the section 1416. The latch member 1542 abuts a surface on the recess 1464 to hold the section 1414 against movement relative to the section 1416 of the holder member 1412.

Although one specific type of connector 1450 and 1452 has been illustrated schematically in FIG. 56 to interconnect the sections 1414 and 1416 of the holder member 1412, it should understood that other known types of connectors could be utilized if desired. For example, a circular band could be provided around the outside of the suture retainer 1410 to hold the two sections 1414 and 1416 against movement relative to each other.

When the suture retainer 1410 is to be used to secure the suture 1418 relative to body tissue, a predetermined force is applied to the suture 1418 to tension the suture. The two sections 1414 and 1416 of the holder member 1412 are pressed against body tissue with a predetermined force. The two sections 1414 and 1416 are moved to positions adjacent to opposite sides of the suture 1418 with the fingers 1422, 1424, and 1426 on the section 1414 aligned with the recesses 1428, 1430, and 1432 in the section 1416. In addition, the fingers 1434 and 1436 on the section 1416 are aligned with the recesses 1438 and 1440 in the section 1414. The two sections 1414 and 1416 are then pressed against each other to move the suture 1418 into the recesses 1428, 1430, 1432, 1438, and 1440 in the sections 1414 and 1416. As this occurs, the latch members 1456 and 1462 of the connectors 1450 and 1452 snap into the recesses 1458 and 1464 with a latching action to fixedly interconnect the two sections 1414 and 1416 of the holder member 1412.

The two sections 1414 and 1416 of the holder member 1412 may be formed of many different materials. However, it is believed that it will be preferred to form the sections 1414 and 1416 of a biodegradable polymer. One biodegradable polymer which may be utilized is polycaperlactone. Alternatively, the suture retainer 1410 could be formed of polyethylene oxide terephthalate or polybutylene terephthalate. It is also contemplated that other biodegradable or bioerodible polymers could be utilized if desired.

Although it is preferred to form the suture retainer 1410 of a biodegradable material, the suture retainer could be formed of a material which is not biodegradable. For example, the suture retainer could be formed of acetyl resin, such as "Delrin" (trademark). Alternatively, the suture retainer 1410 could be formed of a para-dimethylaminobenzenediazo sodium sulfonate, such as "Dexon" (trademark).

In order to obtain a firmer grip on the suture 1418 with the suture retainer 1410, the suture retainer may be plastically deformed after the two sections 1414 and 1416 of the suture retainer 1410 have been interconnected by the connectors 1450 and 1452 (FIG. 56). While the suture retainer 1410 is being pressed against the body tissue with a predetermined force and a predetermined tension is maintained in the portion of the suture 1418 between the anchor and the suture retainer, a pair of force application members are pressed against opposite sides of the suture retainer. The force applied against the suture retainer 1410 by the force application members plastically deforms the material of the suture retainer.

The plastic deformation of the suture retainer 1410 is effective to cause cold flowing of material of the suture retainer. Force is applied against the suture retainer 1410 at a temperature below a transition temperature range for the material of the suture retainer. The force application members which apply force against the suture retainer 1410 may have a configuration corresponding to the configuration of the force application members of FIG. 3 or the force application members of FIG. 18.

It is preferred to effect cold flowing of the material of the suture retainer 1410 without the addition of heat. However, it is contemplated that the suture retainer 1410 could be heated to a temperature which is somewhat above the temperature of the body tissue with which the suture retainer is associated. If desired, heat could be transmitted to the suture retainer 1410 through the force application members which effect plastic deformation of the suture retainer 1410. Although the suture retainer 1410 may be heated, the suture retainer 1410 would be maintained at a temperature below the transition temperature for the material of the suture retainer. However, if desired, the suture retainer could be heated to a temperature in the transition temperature range for the material of the suture retainer.

In the embodiment of the invention illustrated in FIGS. 55 and 56, a single section of the suture is gripped by the suture retainer 1410. However, it is contemplated that a plurality of sections of the suture 1418 could be gripped by the suture retainer 1410 if desired. For example, two sections of the suture 1418 could extend through the suture retainer 1410 in a side-by-side relationship. Alternatively, two separate sets of projections and recesses could be provided. If this was done, one section of the suture 1418 would extend along one set of projections and recesses and the second section of the suture would extend along the second set of projections and recesses.

Figure 57:
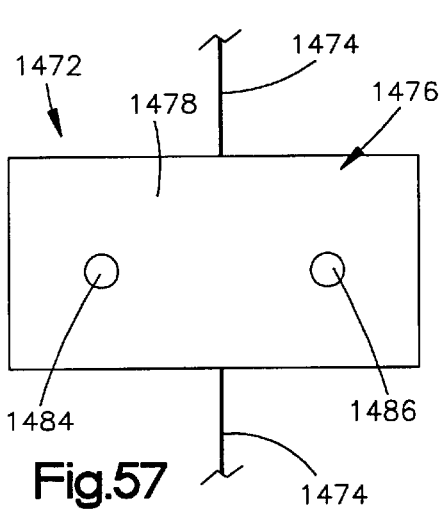
FIG. 57 is a plan view illustrating the manner in which a suture extends through another embodiment of the retainer.
Figure 58:
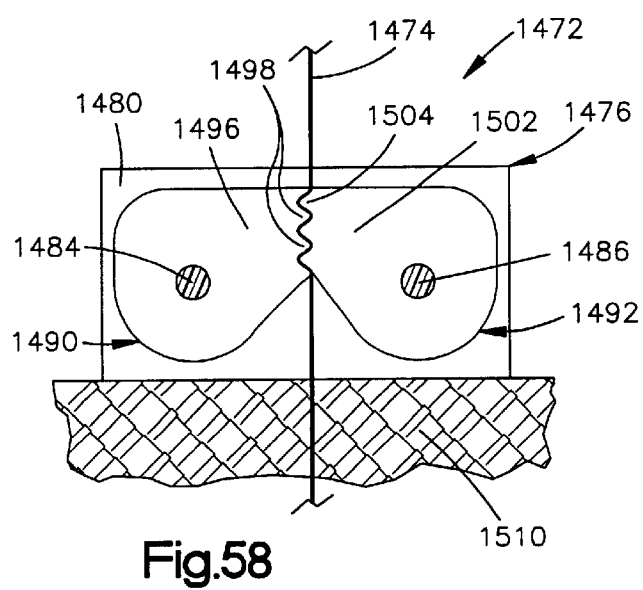
FIG. 58 is a schematic sectional view of the retainer of FIG. 57, illustrating the manner in which a pair of cam members cooperate to grip a suture.

Embodiment of FIGS. 57 and 58

In the embodiment of the invention illustrated in FIGS. 57 and 58, a pair of cam members are utilized to secure a suture relative to body tissue. Since the embodiment of the invention illustrated in FIGS. 57 and 58 is similar to the embodiments of the invention illustrated in FIGS. 1–56, similar terminology will be utilized to identify similar components. It should be understood that one or more of the features of the embodiments of the invention illustrated in FIGS. 1–56 may be used with the embodiment of the invention illustrated in FIGS. 57 and 58.

A suture retainer 1472 is utilized to secure a suture 1474 against movement relative to body tissue. The suture retainer 1472 includes a holder 1476 which encloses a portion of the suture 1474. A portion of the suture disposed between the suture retainer 1472 and an anchor embedded in the body tissue is tensioned with a predetermined force. In addition, a predetermined force is transmitted from the suture retainer 1472 to the body tissue.

The suture 1474 may have a distal end portion connected with a suture anchor embedded in body tissue, in the same manner as in which the suture 1192 of FIG. 45 is connected with the suture anchor 1198 embedded in the body tissue 1194. However, the suture 1474 (FIGS. 57 and 58) could be connected with body tissue in a different manner if desired. For example, the suture 1474 could be connected with body tissue in any one of the ways illustrated in FIGS. 1, 9, 26, 36, and 38 herein. Of course, the suture 1474 could be connected with body tissue in a different manner if desired.

The holder 1476 includes a front panel 1478 (FIG. 57) and a rear panel 1480 (FIG. 58). A pair of mounting pins or bearing sections 1484 and 1486 extend between the front and rear panels 1478 and 1480. The suture 1474 extends between the front and rear panels 1478 and 1480. The suture 1474 is disposed midway between the pins 1484 and 1486.

A left (as viewed in FIG. 58) cam member 1490 is mounted on the pin 1484. A right (as viewed in FIG. 58) cam member 1492 is mounted on the pin 1486. The cam members 1490 and 1492 are rotatable relative to the pins 1484 and 1486. A suitable spring (not shown) is provided to urge the cam member 1490 to rotate in a clockwise direction (as viewed in FIG. 58). Similarly, a suitable spring (not shown) is provided to urge the cam member 1492 to rotate in a counterclockwise direction (as viewed in FIG. 58).

The cam member 1490 has a nose portion 1496 with teeth 1498. Similarly, the cam member 1492 has a nose portion 1502 with teeth 1504. The teeth 1498 on the cam member 1490 mesh with the teeth 1504 on the cam member 1492. A portion of the suture 1474 is disposed in engagement with the teeth 1498 and the teeth 1504. The teeth 1498 and 1504 on the cam members 1490 and 1492 press against the suture 1474 to impart a serpentine configuration to the suture.

When the suture retainer 1492 is to be utilized to secure the suture 1474 against movement relative to body tissue 1510 (FIG. 58), the suture 1474 is positioned between the cam members 1490 and 1492, in the manner indicated schematically in FIG. 58. The suture retainer 1492 is then moved along the suture 1474 toward the body tissue 1510. At this time, the cam members 1490 and 1492 are loosely pressed against the suture 1474 by the biasing springs associated with the cam members. The holder 1476 is moved into engagement with the body tissue and pressed against the body tissue with a predetermined force. At the same time, the suture 1474 is tensioned with a predetermined force.

The suture 1474 is then released. The tension in the portion of the suture between the suture retainer 1472 and a suture anchor embedded in the body tissue 1510 causes the cam member 1490 to tend to rotate in a clockwise direction about the mounting pin 1484. Similarly, the force applied by the suture 1474 against the cam member 1492 tends to rotate the cam member in a counterclockwise direction about the mounting pin 1484. As this occurs, the teeth 1498 and 1504 on the nose portions 1496 and 1502 are pressed firmly against the suture 1474.

The suture retainer 1472 may be formed of many different materials. However, it is believed that it will be preferred to form the suture retainer 1472 of a biodegradable polymer. Thus, the holder 1476, cam members 1490 and 1492, and the biasing springs (not shown) for the cam members 1490 and 1492 are formed of a biodegradable polymer. One biodegradable polymer which may be utilized is polycaperlactone. Alternatively, the suture retainer 1492 could be formed of polyethylene oxide terephthalate or polybutylene terephthalate. It is also contemplated that other biodegradable or bioerodible copolymers could be utilized if desired.

Although it is preferred to form the suture retainer 1472 of a biodegradable material, the suture retainer could formed of a material which is not biodegradable. For example, the suture retainer could be formed of an acetyl resin, such as "Delrin" (trademark). Alternatively, the suture retainer 1472 could be formed of a para-dimethylamino-benzenediazo sodium sulfonate, such as "Dexon" (trademark).

The suture 1474 may be formed of natural or synthetic materials. The suture 1474 may be a monofilament or may be formed of a plurality of interconnected filaments. The suture 1474 may be biodegradable or non-biodegradable. It may be preferred to form the suture 1474 of the same material as the suture retainer 1472. However, the suture 1474 could be formed of a material which is different than the material of the suture retainer.

Once the suture retainer 1472 has gripped the suture 1474 while a predetermined force is being transmitted between the holder 1476 and the body tissue 1510 and while the portion of the suture disposed between the suture retainer 1472 and a suture anchor embedded in the body tissue is tensioned with a predetermined force, the suture retainer 1472 may be plastically deformed to increase the grip of the suture retainer on the suture. A pair of force application members are pressed against opposite sides of the suture retainer 1472 to plastically deform the material of the suture retainer. The force transmitting members may have the same construction as the force transmitting members illustrated in FIG. 3 herein.

The plastic deformation of the suture retainer 1472 is effective to cause cold flowing of material of the suture retainer. Thus, the force application members are effective to cause flowing of the material of the suture retainer 1472 at a temperature below a transition temperature range for the material of the suture retainer. The cold flowing of the material of the suture retainer 1472 enables the material of the suture retainer to bond to and obtain a firm grip on the suture in the manner illustrated schematically in FIG. 4. The cold flowing of the material of the suture retainer 1472 occurs at a temperature which is close to the temperature of the body tissue 1510 and below the transition temperature range of the material forming the suture retainer. However, if desired, the suture retainer 1472 could be heated into its transition temperature range before being plastically deformed.

Embodiment of FIG. 59

In the embodiments of the invention illustrated in FIGS. 1–58, various types of suture retainers for use in securing a suture relative to body tissue have been illustrated. The embodiment of the invention illustrated in FIG. 59 is not limited to any particular suture retainer construction. However, similar terminology will be utilized in describing the components of the embodiment of the invention illustrated in FIG. 59 as were previously utilized in connection with the embodiments of the invention illustrated in FIGS. 1–58.

In the embodiment of the invention illustrated in FIG. 59, a relatively thick layer of tissue, designated by the numeral 1520 is to be connected with a relatively thin layer of tissue, designated by the numeral 1522. A tissue fixation system 1524 is utilized to interconnect the thick and thin layers of tissue. The tissue fixation system 1524 is located a precise distance from an end 1526 of the thick layer of tissue 1520 and an end 1528 of the thin layer 1522 of tissue. In the illustrated embodiment of the invention, the tissue fixation system 1524 is located the same distance from the end 1526 of the thick layer of tissue as in which the tissue fixation system is located from the end 1528 of the thin layer of tissue. This results in the two layers of tissue growing together with a minimum of scarring. In addition, the tissue fixation system 1524 holds the thick layer 1520 and thin layer 1522 of tissue against shifting relative to each other.

If a staple or a loop-type suture was used to interconnect the thick layer 1520 and the thin layer 1522 of tissue, shifting would occur between the two layers of tissue. This shifting would occur inside of the loop formed by the suture or the staple. The shifting can result in excessive scarring and could result in a non-uniform repair of the tissue. The obtaining of a uniform repair of tissue is particularly important when interconnecting a conduit, such as a blood vessel, which has been severed. By using the tissue fixation system 1524, shifting movement can not occur between the two layers of tissue being interconnected. This prevents one of the layers of tissue from being deflected into the path of flow of material, such as blood, through the conduit in a manner which restricts the conduit and subsequently results in a blockage.

The specific tissue fixation system 1524 illustrated in FIG. 59 includes a suture anchor 1532 which is disposed in engagement with an outer side surface 1534 of the thin layer 1522 of tissue. A suture 1536 extends through both the thin layer 1522 of tissue and the thick layer 1520 of tissue. The suture 1536 is disposed the same distance from the end 1526 of the thick layer of tissue as it is located from the end 1528 of the thin layer 1522 of tissue. A suture retainer 1538 is connected with a portion of the suture 1536 opposite from the suture anchor 1532.

When the tissue fixation system 1524 is to be utilized to repair body tissue, the thick layer 1520 and thin layer 1522 of body tissue are positioned in abutting engagement with each other. At this time, the ends 1526 and 1528 of the thick and thin layers 1520 and 1522 of body tissue are disposed in precise alignment with each other. The suture anchor 1532, with the suture 1536 connected thereto, may then be inserted through both the thick layer 1520 of tissue and the thin layer 1522 of tissue. The suture anchor 1532 is positioned in engagement with the outer side surface 1534 of the thin layer of tissue 1522. Alternatively, the suture anchor 1532 could be embedded in the thin layer of tissue 1532.

It is contemplated that a suture anchor inserter having a construction similar to the construction disclosed in U.S. Pat. No. 5,948,002 will be utilized to move the suture anchor 1532 through the two layers of body tissue. The suture anchor may have the same construction and be positioned relative to the body tissue in the manner disclosed in U.S. Pat. Nos. 5,549,631 and/or 5,569,305. Of course other known suture anchor inserters could be used to position suture anchors having different constructions relative to the tissue 1520 and 1522 in a different manner if desired.

Once the suture 1536 has been inserted through the thick layer 1520 and thin layer 1522 of tissue, a suture retainer 1540 is moved along the suture 1536 into abutting engagement with an outer side surface 1542 of the thick layer 1520 of body tissue. The suture retainer 1540 may have the same construction as the suture retainer 50 of FIGS. 1–5. Alternatively, the suture retainer 1540 could have any one of the constructions illustrated in FIGS. 6–58. However, the suture retainer 1540 could have a different construction if desired. If desired, a force distribution member could be provided between the suture retainer 1540 and the thick layer 1520 of body tissue.

The suture 1536 is then tensioned with a predetermined force which is a function of the size of the suture 1536. The suture retainer 1540 is pressed against the thick layer 1520 of body tissue with a predetermined force while the predetermined tension is maintained in the portion of the suture 1536 disposed between the suture retainer 1540 and the suture anchor 1532. While this tension is maintained, the suture retainer 1540 is secured to the suture retainer 1536.

Once the suture retainer 1540 has been secured to the suture retainer 1536, it is contemplated that it may be desired to plastically deform the suture retainer 1540 to increase the grip of the suture retainer on the suture 1536. A pair of force application members may be pressed against opposite sides of the suture retainer 1540 to effect a cold flowing of material of the suture retainer. The cold flowing of the material of the suture retainer 1540 enables the material of the suture retainer 1540 to bond to and obtain a firm grip on the suture 1536. The cold flowing of the material of the suture retainer 1540 may occur at a temperature which is below the transition temperature of the material forming the suture retainer. Alternatively, the suture retainer 1540 may be heated to a temperature which is within its transition temperature range and then plastically deformed.

Since the suture 1536 extends along a straight line through the thick layer 1520 and thin layer 1522 of tissue, there is no tendency for the one of the layers of tissue to shift relative to the other layer of tissue. The straight line application of force through the suture 1536 makes certain that the suture remains at a precise distance from the ends 1526 and 1528 of the thick layer 1520 and thin layer 1522 of tissue.

It is contemplated that a plurality of suture fixation systems, having the same construction as the suture fixation system 1524, will be provided at uniformly spaced apart locations along the ends of the thick and thin layers of tissue. The tissue fixation systems will be positioned predetermined distances apart in an array which extends along the ends 1526 and 1528 of the thick and thin layers 1520 and 1522 of tissue. Each of the tissue fixation systems will be positioned the same distance from the ends 1526 and 1528 of the thick layer 1520 and thin layer 1522 of tissue.

For example, each of the tissue fixation systems 1524 could be positioned exactly five millimeters from the end 1526 of the thick layer of tissue and exactly five millimeters from the end 1528 of the thin layer 1522 of tissue. All of the tissue fixation systems 1524 in the array of tissue fixation systems would be spaced the same distance from the ends 1526 and 1528 of the thick layer 1520 and thin layer of tissue. Of course, the tissue fixation systems 1524 could all be positioned at a distance other than five millimeters from the ends of the thick and thin layers 1520 and 1522 of tissue.

In the embodiment of the invention illustrated in FIG. 59, the tissue fixation system 1524 includes a suture anchor 1532 and a suture retainer 1540. However, it is contemplated that a pair of suture retainers could be connected with opposite end portions of the suture 1536. Although it is believed that it will probably be preferred to provide suture retainers having the same construction at opposite end portions of the suture 1536, the suture retainers at opposite end portions of the suture 1536 could have different constructions.

When the array of tissue fixation systems 1524 have been positioned along the ends 1526 and 1528 of the thick and thin layers 1520 and 1522 of tissue, an inner side surface 1546 on the thick layer 1520 of tissue will be disposed in abutting engagement with an inner side surface 1548 on the thin layer 1522 of tissue. The inner side surfaces 1546 and 1548 on the thick layer 1520 and thin layer 1522 of tissue will be pressed together with the same force at each of the tissue fixation systems 1524 disposed in the linear array of tissue fixation systems.

It is contemplated that the thick layer 1520 of tissue may have a tubular configuration and that the thin layer 1522 of tissue may also have a tubular configuration. The end 1526 of the thick layer 1520 of tissue would have a circular configuration. Similarly, the end 1528 of the thin layer 1522 of tissue would have a circular configuration. The thick and thin layers 1520 and 1522 of tissue would flare or extend radially outward to form an annular flange in which the ends 1526 and 1528 of the thick and thin layers of tissue are held in precise alignment with each other by the circular array of tissue fixation systems 1524. It should be understood that the specific and presently preferred embodiments of the invention illustrated herein are only examples of many different embodiments of the invention which are possible. In describing the presently preferred embodiments of the invention, similar terminology has been used to designate components which are similar in structure and function. The specific features of any one embodiment of the invention may be utilized in association with any of the other embodiments of the invention. For example, it is contemplated that any one of the suture retainers of FIGS. 1–58 could be utilized in the tissue fixation system illustrated in FIG. 59.

Having described the invention, the following is claimed:

1. A method of securing a suture relative to body tissue, said method comprising the steps of positioning the suture in a linear passage in first member, moving the first member along the suture toward the body tissue, applying force to opposite ends of the first member to grip the suture with the first member by changing the configuration of the passage in the first member from a linear configuration to a nonlinear configuration, and retaining the passage in the first member in a nonlinear configuration by applying force against the first member.

2. A method as set forth in claim 1 wherein said step of changing the configuration of the passage in the first member from a linear configuration to a nonlinear configuration includes forming a plurality of bends in the passage in the first member.

3. A method as set forth in claim 1 wherein said step of changing the configuration of the passage in the first member from a linear configuration to a nonlinear configuration includes forming a single bend in the passage in the first member.

4. A method as set forth in claim 1 wherein said step of retaining the passage in the first member in a nonlinear configuration by applying force against the first member includes applying force against a first end portion of the first member with a first retainer section, applying force against a second end portion of the first member with a second retainer section, and latching the first and second retainer sections together.

5. A method as set forth in claim 1 wherein said step of retaining the passage in the first member in a nonlinear configuration includes applying force against opposite end portions of the first member with a retainer member.

6. A method as set forth in claim 1 wherein said step of retaining the passage in the first member in a nonlinear configuration by applying force against the first member includes cold flowing the material of the first member to plastically deform the material of the first member.

7. A method as set forth in claim 1 wherein said step of applying force against the first member includes engaging the opposite end portions of the first member with a second member.

8. A method as set forth in claim 1 wherein said step of retaining the passage in the first member in a nonlinear configuration by applying force against the first member includes inserting opposite end portions of the first member into a recess in a second member.

9. A method of securing a suture relative to body tissue, said method comprising the steps of providing a tubular member having a passage which extends between opposite end portions of the tubular member, moving the tubular member along the suture toward the body tissue with the suture extending through the passage in the tubular member, and, thereafter, gripping the suture with the tubular member by bending the tubular member at a location disposed between the opposite end portions of the tubular member, said step of gripping the suture with the tubular member by bending the tubular member includes forming a bend between a first outer surface area disposed on the outside of the tubular member and a second outer surface area disposed on the outside of the tubular member and moving the first and second outer surface areas on the tubular member into engagement with each other.

10. A method as set forth in claim 9 wherein said step of bending the tubular member includes decreasing a distance between the opposite end portions of the tubular member.

11. A method as set forth in claim 9 further including the step of applying force against portions of the tubular member disposed adjacent to opposite sides of the bend to maintain the tubular member in a bent condition after performing said step of bending the tubular member.

12. A method as set forth in claim 11 wherein said step of applying force against portions of the tubular member disposed adjacent to opposite sides of the bend includes applying force against the opposite end portions of the tubular member with a second member.

13. A method as set forth in claim 11 wherein said step of applying force against the portions of the tubular member disposed adjacent to opposite sides of the bend includes engaging opposite end portions of the tubular member with a retainer.

14. A method as set forth in claim 13 wherein the retainer has a generally C-shaped configuration, said step of engaging opposite end portions of the tubular member with a retainer is performed after performing said step of bending the tubular member.

15. A method as set forth in claim 13 wherein said step of engaging opposite end portions of the tubular member with a retainer includes positioning a band around opposite end portions of the tubular member.

16. A method as set forth in claim 9 wherein said step of bending the tubular member includes bending the tubular member at a notch disposed between the opposite end portions of the tubular member.

17. A method as set forth in claim 9 wherein said step of bending the tubular member includes reducing the size of a portion of the passage in the tubular member to press a portion of the suture firmly against a portion of an inner side surface of the passage in the tubular member.

18. A method as set forth in claim 9 wherein said step of gripping the suture with the tubular member by bending the tubular member includes bending the tubular member at a plurality of locations disposed between opposite end portions of the tubular member to reduce the size of the passage through the tubular member at a plurality of locations along the passage through the tubular member.

19. A method as set forth in claim 9 further including the step of plastically deforming material of the tubular member, said step of plastically deforming the material of the tubular member includes applying force against the material of the tubular member and cold flowing material of the tubular member under the influence of force applied against the tubular member.

20. A method as set forth in claim 9 further including the step of tensioning the suture and transmitting a predetermined force through the tubular member to the body tissue prior to performing said step of bending the tubular member.

21. A method as set forth in claim 9 wherein said step of bending the tubular member includes bending the tubular member at a plurality of locations between opposite end portions of the tubular member, said method further includes applying force against the tubular member with a retainer to hold the tubular member with a plurality of bends in the tubular member.

22. A method as set forth in claim 9 further including the step of holding the tubular member in a bent configuration with a retainer member having a generally C-shaped configuration by applying force against the tubular member with the retainer member.

23. A method as set forth in claim 9 wherein said step of bending the tubular member includes bending the tubular member at a plurality of locations disposed along the tubular member between opposite end portions of the tubular member.

24. A method as set forth in claim 9 further including the step of retaining the tubular member in the bent configuration by engaging the tubular member with a holder, said step of engaging the tubular member with a holder includes applying force against a first end portion of the tubular member with a holder having a generally cylindrical side wall and an end wall which cooperate to at least partially define a recess and applying force against a second end portion of the tubular member with a cover section which is connected with the holder and is movable relative to the holder.

25. A method of securing a suture relative to body tissue, said method comprising the steps of providing a tubular member having a passage which extends between opposite end portions of the tubular member, moving the tubular member along the suture toward the body tissue with the suture extending through the passage in the tubular member, and, thereafter, gripping the suture with the tubular member by bending the tubular member at a location disposed between the opposite end portions of the tubular member, said step of gripping the suture with the tubular member includes moving the opposite end portions of the tubular member into engagement with each other.

26. A method as set forth in claim 25 further including the step of applying force against the opposite end portions of the tubular member to maintain the tubular member in a bent condition after performing said step of bending the tubular member.

27. A method as set forth in claim 26 wherein said step of applying force against the tubular member includes applying force against the opposite end portions of the tubular member with a second member.

28. A method as set forth in claim 26 wherein said step of applying force against the tubular member includes engaging opposite end portions of the tubular member with a retainer.

29. A method as set forth in claim 28 wherein the retainer has a generally C-shaped configuration, said step of engaging opposite end portions of the tubular member with a retainer is performed after performing said step of bending the tubular member.

30. A method as set forth in claim 28 wherein said step of engaging opposite end portions of the tubular member with a retainer includes positioning a band around opposite end portions of the tubular member.

31. A method as set forth in claim 25 wherein said step of bending the tubular member includes bending the tubular member at a notch disposed between the opposite end portions of the tubular member.

32. A method as set forth in claim 25 wherein said step of bending the tubular member includes reducing the size of a portion of the passage in the tubular member to press a portion of the suture firmly against a portion of an inner side surface of the passage in the tubular member.

33. A method as set forth in claim 25 wherein said step of gripping the suture with the tubular member by bending the tubular member includes bending the tubular member at a plurality of locations disposed between opposite end portions of the tubular member to reduce the size of the passage through the tubular member at a plurality of locations along the passage through the tubular member.

34. A method as set forth in claim 25 wherein said step of gripping the suture with the tubular member by bending the tubular member includes forming a bend between a first outer surface area disposed on the outside of the tubular member and a second outer surface area disposed on the outside of the tubular member and moving the first and second outer surface areas on the tubular member into engagement with each other.

35. A method as set forth in claim 25 further including the step of plastically deforming material of the tubular member, said step of plastically deforming the material of the tubular member includes applying force against the material of the tubular member and cold flowing material of the tubular member under the influence of force applied against the tubular member.

36. A method as set forth in claim 25 further including the step of tensioning the suture and transmitting a predetermined force through the tubular member to the body tissue prior to performing said step of bending the tubular member.

37. A method as set forth in claim 25 wherein said step of bending the tubular member includes bending the tubular member at a plurality of locations between opposite end portions of the tubular member, said method further includes applying force against the tubular member with a retainer to hold the tubular member with a plurality of bends in the tubular member.

38. A method as set forth in claim 25 further including the step of holding the tubular member in a bent configuration with a retainer member having a generally C-shaped configuration by applying force against opposite end portions of the tubular member with the retainer member.

39. A method as set forth in claim 25 wherein said step of bending the tubular member includes bending the tubular member at a plurality of locations disposed along the tubular member between opposite end portions of the tubular member.

40. A method as set forth in claim 25 further including the step of retaining the tubular member in the bent configuration by engaging the tubular member with a holder, said step of engaging the tubular member with a holder includes applying force against a first end portion of the tubular member with a holder having a generally cylindrical side wall and an end wall which cooperate to at least partially define a recess and applying force against a second end portion of the tubular member with a cover section which is connected with the holder and is movable relative to the holder.

41. An apparatus for use in securing a suture relative to body tissue, said apparatus comprising a tubular member having a passage through which the suture extends, said tubular member having a bend along which the suture extends, said passage in said tubular member having a reduced cross sectional size at said bend to enable said tubular member to retain the suture against movement along said passage in said tubular member, and a holder which engages a first portion of said tubular member and a second portion of said tubular member, said bend in said tubular member being disposed between said first and second portions of said tubular member, said holder has a generally C-shaped configuration, said tubular member being at least partially disposed in an opening which is formed by said holder, said holder being effective to apply force to said first and second portions of said tubular member to maintain said bend in said tubular member.

42. An apparatus as set forth in claim 41 wherein said tubular member is resiliently bent from a first configuration to a second configuration to form the bend in said tubular member, said holder being effective to maintain said bend in said tubular member against the influence of a tendency of said tubular member to spring back from the second configuration toward the first configuration.

43. A method of securing a suture relative to body tissue, said method comprising the steps of enclosing a portion of the suture with a tubular member having a longitudinal central axis, deforming the tubular member to grip a portion of the suture which is enclosed by the tubular member, said step of deforming the tubular member includes changing the configuration of the longitudinal central axis of the tubular member from a first configuration to a second configuration, and retaining the longitudinal central axis of the tubular member in the second configuration by applying force against the tubular member with at least a second member.

44. A method as set forth in claim 43 further including the step of sliding the tubular member along the suture toward the body tissue while the suture is at least partially enclosed by the tubular member and while the longitudinal central axis of the tubular member has the first configuration.

45. A method as set forth in claim 43 wherein said step of deforming the tubular member includes bending the tubular member to change the configuration of the longitudinal central axis of the tubular member from the first configuration to the second configuration.

46. A method as set forth in claim 43 wherein said step of enclosing a portion of the suture with the tubular member includes moving a portion of the suture through a passage which extends along the longitudinal central axis of the tubular member while the longitudinal central axis of the tubular member has the first configuration.

47. A method as set forth in claim 43 wherein said step of retaining the longitudinal central axis of the tubular in the second configuration includes at least partially enclosing opposite end portions of the tubular member with the second member.

48. A method as set forth in claim 43 wherein said second member has a recess, said step of retaining the longitudinal central axis of the tubular member in the second configuration includes inserting one portion of the tubular member into the recess in the second member with another portion of the tubular member disposed outside of the recess in the second member.

49. A method as set forth in claim 43 wherein said step of retaining the longitudinal central axis of the tubular member in the second configuration includes moving opposite end portions of the tubular member into a recess in the second member with a portion of the tubular member being disposed between the opposite end portions of the tubular member being disposed outside of the recess.

50. A method as set forth in claim 49 wherein said step of moving opposite end portions of the tubular member into the recess in the second member includes sliding the tubular member along the suture.

51. A method as set forth in claim 43 wherein said step of deforming the tubular member includes bending the tubular member at a weakened location between opposite end portions of the tubular member to change the configuration of the longitudinal central axis of the tubular member from the first configuration to the second configuration.

52. A method as set forth in claim 43 wherein said tubular member has first and second end portions, said step of deforming the tubular member includes moving the first and second end portions of the tubular member toward each other by deforming a portion of the tubular member disposed between the first and second end portions of the tubular member.

53. A method as set forth in claim 43 further including the step of plastically deforming material of at least the tubular member while the longitudinal central axis of the tubular member has the second configuration and while the second member is applying force against the tubular member, said step of plastically deforming the material of the tubular member includes applying force against the tubular member and pressing material of the tubular member against the suture by cold flowing material of the tubular member under the influence of force applied against surface areas on the tubular member.

54. A method as set forth in claim 43 further including the steps of tensioning the suture and transmitting a predetermined force from the tubular member to the body tissue prior to performing said step of deforming the tubular member.

55. A method as set forth in claim 43 wherein the step of deforming the tubular member is performed with the tubular member at a temperature below a transition temperature of material forming the tubular member.

56. A method as set forth in claim 43 further including the step of plastically deforming material of the tubular member while the tubular member has the second configuration and while the second member is applying force against the tubular member by applying at least a predetermined minimum force against the tubular member for at least a predetermined minimum period of time.

57. A method as set forth in claim 43 wherein said step of deforming the tubular member includes bending the tubular member from the first configuration to the second configuration while the tubular member is disposed in engagement with the second member.

58. A method as set forth in claim 43 wherein the second member has a generally C-shaped configuration, said step of retaining the tubular member in the second configuration by applying force against the tubular member with the second member includes engaging opposite end portions of the tubular member with the second member.

59. A method as set forth in claim 43 wherein the second member has a generally cylindrical side wall and an end wall which cooperate to at least partially define a recess, said step of retaining the tubular member in the second configuration includes applying force against the tubular member with the end wall of the second member and with a cover section which is connected with the second member and is moveable relative to the second member.

60. A method as set forth in claim 43 where said step of deforming the tubular member includes forming a bend in the suture and gripping the suture with the tubular member at the location where the bend is formed in the suture.

61. A method as set forth in claim 43 wherein said step of deforming the tubular member includes cold flowing material of the tubular member with the suture disposed in the passage in the tubular member.

62. A method as set forth in claim 61 wherein said step of deforming the tubular member by cold flowing material of the tubular member is performed while the longitudinal central axis of the tubular member has the second configuration.

63. A method as set forth in claim 43 wherein the tubular member has an outer side surface with a cylindrical configuration, said step of deforming the tubular member includes changing the configuration of a portion of the outer side surface of the tubular member to a noncylindrical configuration.

64. A method as set forth in claim 43 wherein the tubular member has a central passage with a surface having a cylindrical configuration, said step of deforming the tubular member includes changing the configuration of a portion of the surface of the passage from a cylindrical configuration to noncylindrical configuration.

65. A method of securing a suture relative to body tissue, said method comprising the steps of providing a tubular member having a passage which extends between opposite end portions of the tubular member, moving the tubular member along the suture toward the body tissue with the suture extending through the passage in the tubular member, and, thereafter, bending the tubular member and gripping the suture at a location in the tubular member where a bend is formed in the tubular member, said step of bending the tubular member includes changing a configuration of the passage from a linear configuration to a nonlinear configuration.

66. A method as set forth in claim 65 wherein said step of bending the tubular member includes decreasing a distance between the opposite end portions of the tubular member.

67. A method as set forth in claim 65 further including the step of applying force against the tubular member to maintain the tubular member in a bent condition after performing said step of bending the tubular member.

68. A method as set forth in claim 67 wherein said step of applying force against the tubular member includes applying force against the opposite end portions of the tubular member with a second member.

69. A method as set forth in claim 67 wherein said step of applying force against the tubular member includes positioning the opposite end portions of the tubular member in a recess formed in a holder for the tubular member.

70. A method as set forth in claim 69 wherein the holder of for the tubular member has a generally C-shaped configuration, said step of positioning opposite end portions of the tubular member in the recess in the holder is performed after performing said step of bending the tubular member.

71. A method as set forth in claim 67 wherein said step of applying force against the tubular member includes positioning a band around opposite end portions of the tubular member.

72. A method as set forth in claim 65 wherein said step of bending the tubular member includes bending the tubular member at a notch disposed between and spaced from the opposite end portions of the tubular member.

73. A method as set forth in claim 65 wherein said step of bending the tubular member includes reducing the size of a portion of the passage in the tubular member at the location where the bend is formed in the tubular member to press a portion of the suture firmly against a portion of an inner side surface of the passage in the tubular member at the location where the bend is formed in the tubular member.

74. A method as set forth in claim 65 wherein said step of gripping the suture with the tubular member by bending the tubular member includes bending the tubular member at a plurality of locations disposed between opposite end portions of the tubular member to reduce the size of the passage through the tubular member at a plurality of locations along the passage through the tubular member.

75. A method as set forth in claim 65 further including the step of plastically deforming material of the tubular member, said step of plastically deforming the material of the tubular member includes applying force against the material of the tubular member and cold flowing material of the tubular member under the influence of force applied against the tubular member.

76. A method as set forth in claim 65 further including the step of tensioning the suture and transmitting a predetermined force through the tubular member to the body tissue prior to performing said step of bending the tubular member.

77. A method as set forth in claim 65 wherein said step of bending the tubular member includes bending the tubular member at a plurality of locations between opposite end portions of the tubular member, said method further includes applying force against the tubular member with a retainer to hold the tubular member with a plurality of bends in the tubular member.

78. A method as set forth in claim 65 further including the step of holding the tubular member in a bent configuration with a retainer member having a generally C-shaped configuration by applying force against opposite end portions of the tubular member with the retainer member.

79. A method as set forth in claim 65 wherein said step of bending the tubular member includes bending the tubular member at a plurality of locations disposed along the tubular member between opposite end portions of the tubular member.

80. A method as set forth in claim 65 further including the step of retaining the tubular member in the bent configuration by engaging the tubular member with a holder, said step of engaging the tubular member with a holder includes applying force against a first end portion of the tubular member with a holder having a generally cylindrical side wall and an end wall which cooperate to at least partially define a recess and applying force against a second end portion of the tubular member with a cover section which is connected with the holder and is movable relative to the holder.

81. A method as set forth in claim 65 wherein said step of bending the tubular member includes moving a surface area on one side of the passage in the tubular member toward a surface area on a side of the passage opposite from the one side at the location where the bend is formed in the tubular member.

82. A method as set forth in claim 65 wherein said step of bending the tubular member includes decreasing a cross sectional size of the passage in the tubular member at a location between opposite end portions of the passage while maintaining cross sectional sizes of the opposite end portions of the passage constant.

83. A method as set forth in claim 65 wherein said step of bending the tubular member includes decreasing a cross sectional size of the passage in the tubular member throughout an axial extent of the passage in the tubular member.

84. A method as set forth in claim 65 wherein the tubular member has an outer side surface with a cylindrical configuration, said step of bending the tubular member includes changing the configuration of a portion of the outer side surface of the tubular member to a noncylindrical configuration.

85. A method as set forth in claim 65 wherein the tubular member has a central passage with a surface having a cylindrical configuration, said step of bending the tubular member includes changing the configuration of a portion of the surface of the passage from a cylindrical configuration to a noncylindrical configuration.

86. A method of securing a suture relative to body tissue, said method comprising the steps of providing a tubular member formed of a polymeric material and having a passage which extends between opposite end portions of the tubular member, moving the tubular member along the suture toward the body tissue with the suture extending through the passage in the tubular member, and, thereafter, gripping the suture by decreasing a cross sectional size of a portion of the passage disposed between opposite end portions of the passage while maintaining cross sectional sizes of the opposite end portions of the passage constant.

87. A method as set forth in claim 86 wherein said step of decreasing a cross sectional size of a portion of the passage includes plastically deforming the polymeric material of the tubular member at a location between opposite end portions of the tubular member.

88. A method as set forth in claim 86 wherein said step of decreasing a cross sectional size of a portion of the passage includes bending the tubular member.

89. A method as set forth in claim 86 wherein said step of decreasing a cross sectional size of a portion of the passage includes changing a configuration of a longitudinal central axis of the tubular member from a first configuration to a second configuration.

90. A method as set forth in claim 89 further including the step of retaining the longitudinal central axis of the tubular member in the second configuration by applying force against the tubular member with a second member.

91. A method as set forth in claim 86 wherein said step of decreasing a cross sectional size of a portion of the passage includes changing a configuration of the portion of the passage from a first configuration to a second configuration.

92. A method as set forth in claim 86 wherein said step of decreasing a cross sectional size of a portion of the passage includes changing a configuration of the passage from a linear configuration to a nonlinear configuration.

93. A method as set forth in claim 86 wherein said step of decreasing a cross sectional size of a portion of the passage includes moving a surface area on one side of the passage in the tubular member toward a surface area on a side of the passage opposite from the one side.

94. A method of securing a suture relative to body tissue, said method comprising the steps of providing a tubular member formed of a polymeric material and having a passage which extends between opposite end portions of the tubular member, moving the tubular member along the suture toward the body tissue with the suture extending through the passage in the tubular member, and, thereafter, gripping the suture by deforming at least a portion of the polymeric material of the tubular member at a location disposed between opposite end portions of the tubular member without deforming the opposite end portions of the tubular member.

95. A method as set forth in claim 94 wherein said step of deforming a portion of the tubular member includes decreasing a cross sectional size of a portion of the passage disposed between opposite end portions of the passage while maintaining cross sectional sizes of the opposite end portions of the passage constant.

96. A method as set forth in claim 94 wherein said step of deforming a portion of the tubular member includes bending the tubular member at a location disposed between opposite end portions of the tubular member.

97. A method as set forth in claim 95 wherein said step of deforming a portion of the tubular member includes changing a configuration of a longitudinal central axis of the tubular member from a first configuration to a second configuration.

98. A method as set forth in claim 97 further including the step of retaining the longitudinal central axis or the tubular member in the second configuration by applying force against the tubular member with a second member.

99. A method as set forth in claim 94 wherein said step of deforming a portion of the tubular member includes changing a configuration of a portion of the passage from a first configuration to a second configuration.

100. A method as set forth in claim 94 wherein said step of deforming a portion of the tubular member includes changing a configuration of the passage from a linear configuration to a nonlinear configuration.

101. A method as set forth in claim 94 wherein said step of deforming a portion of the tubular member includes moving a surface area on one side of a passage in the tubular member toward a surface area on a side of the passage opposite from the one side.

102. An apparatus for use in securing a suture relative to body tissue, said apparatus comprising a tubular member having a passage through which the suture extends, said tubular member having a bend along which the suture extends, said passage in said tubular member having a first surface area which presses the suture against a second surface area of said passage at said bend to retain the suture against movement along said passage in said tubular member.

103. An apparatus as set forth in claim 102 wherein said tubular member is resiliently bent from a first configuration to a second configuration to form said bend in said tubular member, said apparatus further includes a holder which engages said tubular member to maintain said bend in said tubular member against the influence of a tendency of said tubular member to spring back from the second configuration toward the first configuration.

104. An apparatus as set forth in claim 103 wherein said holder includes a first portion which is connected to a first end of said tubular member, a second portion which is connected to a second end of said tubular member, and a connector which interconnects said first and second portions of said holder.

105. An apparatus for use in securing a suture relative to body tissue, said apparatus comprising a tubular member having a first linear end portion, a second linear end portion, and bend portion extending between said first and second linear end portions, said first linear end portion of said tubular member having a longitudinal central axis which extends transverse to a longitudinal central axis of said second linear end portion of said tubular member, said tubular member having a passage through which the suture extends, said bend portion of said tubular member being effective to grip the suture to hold the suture against movement relative to said tubular member.

106. An apparatus as set forth in claim 105 further including a holder which engages said first and second linear end portions of said tubular member and is spaced from said bend portion of said tubular member, said holder being effective to retain said first and second linear end portions of said tubular member against relative movement.

107. An apparatus as set forth in claim 106 wherein said passage has the same cross sectional area in said first and second linear end portions of said tubular member, said passage having a cross sectional area in said bend portion of said tubular member which is less than the cross sectional area of said passage in said first and second linear end portions of said tubular member.

108. An apparatus for use in securing a suture relative to body tissue, said apparatus comprising a tubular member having a passage which extends through said tubular member which extends between first and second end portions of said tubular member, said passage having a first end portion disposed in said first end portion of said tubular member, said passage having a second end portion disposed in said second end portion of said tubular member, said passage having a gripping portion which is disposed between said first and second end portions of said passage and is disposed in an intermediate portion of said tubular member located between said first and second end portions of said tubular member, said first and second end portions of said passage having the same cross sectional areas, said gripping portion of said passage having a cross sectional area which is less than the cross sectional areas of said first and second end portions of said passage.

109. An apparatus as set forth in claim 108 where said gripping portion of said passage engages opposite sides of the suture to hold the tubular member against movement along the suture.

110. A method of securing a suture relative to body tissue, said method comprising the steps of providing a member having a linear passage with linear longitudinal central axis which extends between opposite end portions of the member, bending the member to change the configuration of the passage to a nonlinear configuration and to change the configuration of the longitudinal central axis of the passage to a nonlinear configuration, collapsing at least a portion of the passage by deforming at least a portion of the member, and gripping the suture with surface areas disposed on opposite sides of the passage to retain the suture and member against relative movement.

111. A method as set forth in claim 110 further including the step of retaining the member in a configuration to which the member is bent by applying force against the member with a second member.

112. A method as set forth in claim 110 wherein said step of collapsing at least a portion of the passage includes plastically deforming material of the member under the influence of force applied against the member.

113. A method as set forth in claim 110 further including the steps of moving the member along the suture toward the body tissue and transmitting a predetermined force from the member to the body tissue prior to performing said steps of bending the member and collapsing the passage.

114. A method as set forth in claim 110 further including the steps of moving the member along the suture toward the body tissue and tensioning the suture with a predetermined force prior to performing said steps of bending the member and collapsing the passage.

115. A method as set forth in claim 110 wherein said step of collapsing the passage is performed after performing said step of bending the member.

116. A method as set forth in claim 110 wherein said step of collapsing the passage is performed contemporaneously with performance of said step of bending the member.

117. A method of securing a suture relative to body tissue, said method comprising the steps of providing a tubular member having a passage with a longitudinal central axis, moving the tubular member along the suture with the suture extending through the passage, bending the tubular member to change the configuration of the longitudinal central axis of the tubular member from a first configuration to a second configuration, and gripping the suture with the tubular member at a location in the tubular member where a bend is formed in the tubular member during performance of said step of bending the tubular member.

118. A method as set forth in claim 117 further including the step of maintaining the bend in the tubular member by holding the tubular member with at least a second member.

119. A method as set forth in claim 118 wherein said step of maintaining the bend in the tubular member by holding the tubular member with a second member includes engaging opposite end portions of the tubular member with the second member.

120. A method as set forth in claim 118 wherein said step of maintaining the bend in the tubular member by holding the tubular member with a second member includes holding the tubular member with a second member having a generally C-shaped configuration.

121. A method as set forth in claim 118 further including the step of deforming material of the at least the tubular member to press material of the tubular member against the suture while the tubular member is held by the second member.

122. A method as set forth in claim 118 wherein said step of holding the tubular member with a second member includes at least partially enclosing opposite end portions of the tubular member with the second member.

123. A method as s set forth in claim 117 wherein said step of bending the tubular member includes forming a plurality of bends in the tubular member at locations which spaced apart along the longitudinal central axis of the tubular member.

124. A method as set forth in claim 123 further including the step of maintaining the plurality of bends in the tubular member by holding the tubular member with at least a second member.

125. A method as set forth in claim 124 wherein said step of holding the tubular member with the second member includes engaging the tubular member with the second member at a location disposed between first and second bends of the plurality of bends.

126. A method as set forth in claim 124 wherein said step of holding the second member with a tubular member includes holding the tubular member with a second member having a generally C-shaped configuration.

127. A method as set forth in claim 123 further including the step of deforming material of the tubular member to press the material of the tubular member against the suture.

128. A method as set forth in claim 127 wherein said step of deforming material of the tubular member is performed after forming a plurality of bends in the tubular member.

129. A method as set forth in claim 117 further including the step of deforming material of the tubular member to press the material of the tubular member against the suture.

130. A method as set forth in claim 129 wherein said step of deforming material of the tubular member to press the material of the tubular member against the suture includes deforming material of the tubular member adjacent to opposite end portions of the tubular member.

131. A method as set forth in claim 129 wherein said step of deforming material of the tubular member to press the tubular member against the suture includes deforming material which forms a bend in the tubular member.

132. A method as set forth in claim 129 wherein said step of deforming material of the tubular member to press the material of the tubular member against the suture is performed contemporaneously with performance of said step of bending the tubular member.

133. A method as set forth in claim 117 wherein said step of bending the tubular member to change the configuration of the longitudinal central axis of the tubular member from the first configuration to the second configuration includes changing the configuration of the longitudinal central axis of the tubular member from a linear configuration to a nonlinear configuration.

134. A method of securing a suture relative to body tissue, said method comprising the steps of enclosing a portion of the suture with a tubular member, forming a bend in the portion of the suture enclosed by the tubular member by deforming the tubular member, and gripping the suture with the tubular member at the location where the bend is formed in the suture.

135. A method as set forth in claim 134 wherein said step of forming a bend in the portion of the suture enclosed by the tubular member includes changing a configuration of a longitudinal central axis of the tubular member from a first configuration to a second configuration.

136. A method as set forth in the claim 135 further including the step of retaining the longitudinal central axis of the tubular member in the second configuration by applying force against the tubular member with at least a second member.

137. A method as set forth in claim 136 wherein said step of applying force against the tubular member with a second member includes positioning a band around opposite end portions of the tubular member.

138. A method as set forth in claim 134 wherein said step of forming a bend in the portion of the suture enclosed by the tubular member includes bending the tubular member to move an outer side surface area on a first end portion of the tubular member into engagement with an outer side surface area on a second end portion of the tubular member, and retaining the outer side surface areas on the first and second end portions of the tubular member in engagement by positioning a band around the first and second end portions of the tubular member.

139. A method as set forth in claim 134 wherein said step of forming a bend in the portion of the suture enclosed by the tubular member by deforming the tubular member includes changing a configuration of a passage in the tubular member from a linear configuration to a nonlinear configuration with the portion of the suture enclosed by the tubular member disposed in the passage.

140. A method as set forth in claim 134 wherein said step of forming a bend in the portion of the suture enclosed by the tubular member by deforming the tubular member and gripping the suture with the tubular member include decreasing a cross sectional size of a portion of a passage in the tubular member while maintaining cross sectional sizes of opposite end portions of the passage constant with the portion of the suture enclosed by the tubular member disposed in the passage.

141. A method as set forth in claim 134 wherein said steps of forming a bend in the portion of the suture enclosed by the tubular member by deforming the tubular member and gripping the suture with the tubular member include deforming a portion of the tubular member disposed between opposite end portions of the tubular member without deforming opposite end portions of the tubular member.

142. A method as set forth in claim 134 wherein said steps of forming a bend in the portion of the suture enclosed by the tubular member by deforming the tubular member and gripping the suture with the tubular member include collapsing at least a portion of a passage in the tubular member with the portion of the suture enclosed by the tubular member disposed in the passage.

143. A method as set forth in claim 134 wherein said step of forming a bend in the portion of the suture enclosed by the tubular member includes forming a bend in the tubular member, said method further includes maintaining the bend in the tubular ember by holding the tubular member with at least a second member.

144. A method as set forth in claim 143 wherein said step of maintaining the bend in the tubular member by holding the tubular member with a second member includes engaging opposite end portions of the tubular member with the second member.

145. A method as set forth in claim 143 wherein said step of maintaining the bend in tubular member by holding the tubular member with a second member includes holding the tubular member with a second member having a generally C-shaped configuration.

146. A method as set forth in claim 143 wherein said step of holding the tubular member with a second member includes at least partially enclosing opposite end portions of the tubular member with the second member.

147. A method as set forth in claim 134 wherein said steps of forming a bend in the suture and gripping the suture with the tubular member include deforming material of the tubular member to press the material of the tubular member against the suture.

148. A method as set forth in claim 147 wherein said step of deforming material of the tubular member to press the material of the tubular member against the suture includes deforming material of the tubular member adjacent to opposite end portions of the tubular member.

149. A method as set forth in claim 147 wherein said step of deforming material of the tubular member to press the tubular member against the suture includes deforming material which forms a bend in the tubular member.

* * * * *